United States Patent

Janssens et al.

[11] Patent Number: 5,468,743
[45] Date of Patent: Nov. 21, 1995

[54] IMIDAZO[2,1-B]BENZAZEPINE DERIVATIVES, COMPOSITIONS AND METHOD OF USE

[75] Inventors: Frans E. Janssens, Bonheiden; Gaston S. M. Diels, Ravels; Joseph E. Leenaerts, Rijkevorsel, all of Belgium

[73] Assignee: Janssen Pharmaceutica N.V., Beerse, Belgium

[21] Appl. No.: 142,474

[22] PCT Filed: Jun. 9, 1992

[86] PCT No.: PCT/EP92/01330

§ 371 Date: Nov. 29, 1993

§ 102(e) Date: Nov. 29, 1993

[87] PCT Pub. No.: WO92/22551

PCT Pub. Date: Dec. 23, 1992

Related U.S. Application Data

[63] Continuation-in-part of Ser. No. 853,631, Mar. 18, 1992, abandoned, which is a continuation of Ser. No. 714,486, Jun. 13, 1991, abandoned.

[51] Int. Cl.⁶ .................. C07D 487/04; A61K 31/55
[52] U.S. Cl. ........................... 514/214; 540/579
[58] Field of Search ..................... 540/579; 514/214

[56] References Cited

U.S. PATENT DOCUMENTS

| | | | |
|---|---|---|---|
| 5,008,268 | 4/1991 | Janssens et al. | 514/272 |
| 5,393,753 | 2/1995 | Friary | 514/214 |

FOREIGN PATENT DOCUMENTS

| | | | |
|---|---|---|---|
| 0000716 | 2/1979 | European Pat. Off. | |
| WO92/6981 | 4/1992 | WIPO | 540/579 |

*Primary Examiner*—Philip I. Datlow
*Attorney, Agent, or Firm*—Charles J. Metz

[57] ABSTRACT

The present invention is concerned with novel imidazo[2,1-b][3]benzazepines of formula

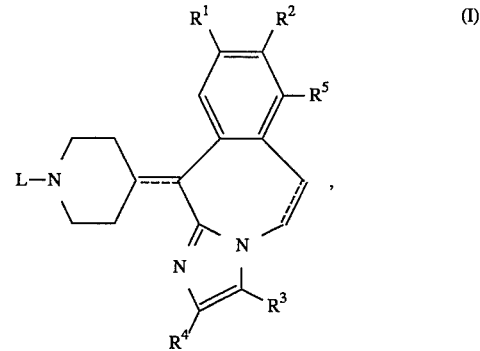

the pharmaceutically acceptable addition salts and stereochemically isomeric forms thereof, wherein each of the dotted lines independently represents an optional bond; $R^1$ represents hydrogen, halo, $C_{1-4}$alkyl or $C_{1-4}$alkyloxy; $R^2$ represents hydrogen, halo, $C_{1-4}$alkyl or $C_{1-4}$alkyloxy; $R^3$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl; $R^4$ represents hydrogen, $C_{1-4}$alkyl, hydroxy$C_{1-4}$alkyl, phenyl or halo; $R^5$ represents hydrogen, $C_{1-4}$alkyl or halo; L represents hydrogen; $C_{1-6}$alkyl; $C_{1-6}$alkyl substituted with one substituent selected from the group consisting of hydroxy, halo, $C_{1-4}$alkyloxy, hydroxycarbonyl, $C_{1-4}$alkyloxycarbonyl, $C_{1-4}$alkyloxycarbonyl-$C_{1-4}$alkyloxy, hydroxycarbonyl$C_{1-4}$alkyloxy, $C_{1-4}$alkyloxycarbonylamino, $C_{1-4}$alkylaminocarbonyl, $C_{1-4}$alkylaminocarbonylamino, $C_{1-4}$alkylaminothiocarbonylamino, aryl, aryloxy and arylcarbonyl; $C_{1-6}$alkyl substituted with both hydroxy and aryloxy; $C_{3-6}$alkenyl; $C_{3-6}$alkenyl substituted with aryl; or, L represents a radical of formula —Alk—Y—Het¹(a-1),—Alk—NH—CO—Het²(a-2)or —Alk—Het³(a-3); provided that 6,11-dihydro-11-(4-piperidinylidene)-5H-imidazo[2,1-b][3]benzazepine is excluded, which are useful antiallergic compounds.

Compositions comprising said compounds, methods of using and processes for preparing the same.

16 Claims, No Drawings

IMIDAZO[2,1-B]BENZAZEPINE DERIVATIVES, COMPOSITIONS AND METHOD OF USE

CROSS-REFERENCE TO RELATED APPLICATIONS

This application is a 35 U.S.C. 371 application based upon PCT Application No. PCT/EP 92/01330, filed Jun. 9, 1992, which is a continuation-in-part of U.S. applications Ser. No. 853,631, filed Mar. 18, 1992, now abandoned, which is a continuation of Ser. No. 714,486, filed Jun. 13, 1991, now abandoned.

BACKGROUND OF THE INVENTION

In WO 88/03138 there are described benzo[5,6]cycloheptapyridines which possess antiallergic and anti-inflammatory activity. In EP-A-0,339,978 there are described (benzo- or pyrido)cyclohepta heterocyclics which are useful as PAF antagonists, antihistaminics and/or anti-inflammatory agents.

In WO 92/06981 there are described 6,11-dihydro-11-(4-piperidinylidene)-5H-imidazo[ 2,1-b][3]benzazepine and 1-acetyl-4-(5,6-dihydro-11H-imidazol[ 1,2-b][3] -benzazepine-11-ylidene)piperidine, the latter of which is useful as a PAF antagonist.

In the J. Med. Chem., 26 (1983), 974–980 there are described some 1-methyl-4 -piperidinylidene-9-substituted pyrrolo[2,1-b][3]benzazepine derivatives having neuroleptic properties.

The compounds of the present invention differ structurally from the cited art-known compounds by the fact that the central 7-membered ring invariably contains a nitrogen atom of a fused imidazole ring, and by their favorable antiallergic activity.

DESCRIPTION OF THE INVENTION

The present invention is concerned with novel imidazo [2,1-b][3]benzazepines of formula

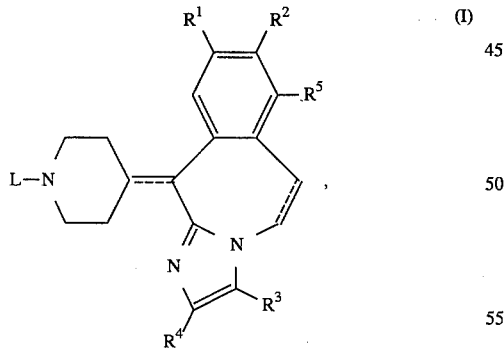

(I)

the pharmaceutically acceptable addition salts and stereochemically isomeric forms thereof, wherein each of the dotted lines independently represents an optional bond;

$R^1$ represents hydrogen, halo, $C_{1-4}$alkyl or $C_{1-4}$alkyloxy;

$R^2$ represents hydrogen, halo, $C_{1-4}$alkyl or $C_{1-4}$alkyloxy;

$R^3$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^4$ represents hydrogen, $C_{1-4}$alkyl, hydroxy$C_{1-4}$alkyl, phenyl or halo;

$R^5$ represents hydrogen, $C_{1-4}$alkyl or halo;

L represents hydrogen; $C_{1-6}$alkyl; $C_{1-6}$alkyl substituted with one substituent selected from the group consisting of hydroxy, halo, $C_{1-4}$alkyloxy, hydroxycarbonyl, $C_{1-4}$alkyloxycarbonyl, $C_{1-4}$alkyloxycarbonyl$C_{1-4}$alkyloxy, hydroxycarbonyl-$C_{1-4}$alkyloxy, $C_{1-4}$alkyloxycarbonylamino, $C_{1-4}$alkylaminocarbonyl, $C_{1-4}$alkylaminocarbonylamino, $C_{1-4}$alkylaminothiocarbonylamino, aryl, aryloxy and arylcarbonyl; $C_{1-6}$alkyl substituted with both hydroxy and aryloxy; $C_{3-6}$alkenyl; $C_{3-6}$alkenyl substituted with aryl;

wherein each aryl is phenyl or phenyl substituted with halo, cyano, hydroxy, $C_{1-4}$alkyl, $C_{1-4}$alkyloxy, aminocarbonyl or phenyl substituted with $C_{1-4}$alkyloxycarbonyl or hydroxycarbonyl; or, L represents a radical of formula $$\text{—Alk—Y—Het}^1 \qquad (a\text{-}1),$$

$$\text{—Alk—NH—CO—Het}^2 \qquad (a\text{-}2), \text{ or}$$

$$\text{—Alk—Y—Het}^3 \qquad (a\text{-}3); \text{ wherein}$$

Alk represents $C_{1-4}$alkanediyl;

Y represents O, S or NH;

$Het^1$, $Het^2$ and $Het^3$ each represent furanyl, thienyl, oxazolyl, thiazolyl or imidazolyl each optionally substituted with one or two $C_{1-4}$alkyl substituents; pyrrolyl or pyrazolyl optionally substituted with formyl, hydroxy$C_{1-4}$alkyl, hydroxycarbonyl, $C_{1-4}$alkyloxycarbonyl or one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; imidazo[4,5-c] pyridin-2-yl; and $Het^3$ may also represent 4,5-dihydro-5-oxo-1 H-tetrazolyl substituted with $C_{1-4}$alkyl, 2-oxo-3-oxazolidinyl, 2,3-dihydro-2-oxo-1H-benzimidazol-1-yl or a radical of formula

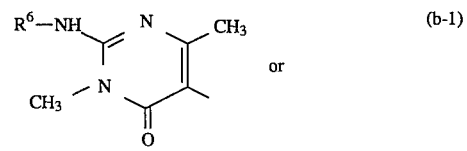

or

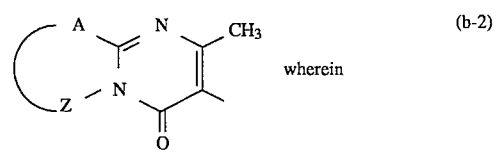

wherein $R^6$ represents hydrogen or $C_{1-4}$alkyl; and

A-Z represents —S—CH=CH—, —S—CH$_2$—CH$_2$—, —S—CH$_2$—CH$_2$—CH$_2$—, —CH=CH—CH=CH—, —CH$_2$—CH$_2$—CH$_2$—CH$_2$—, —N(CH$_3$)—C(CH$_3$)=CH— or —CH=C(CH$_3$)—O—;

provided that 6,11-dihydro-11-(4-piperidinylidene)-5 H-imidazo[2,1 -b][3]benzazepine is ecxluded.

As used in the foregoing definitions halo defines fluoro, chloro, bromo and iodo; $C_{1-4}$alkyl defines straight and branched chain saturated hydrocarbon radicals having from 1 to 4 carbon atoms such as, for example, methyl, ethyl, propyl, 1-methylethyl, butyl, 1-methylpropyl, 2-methylpropyl and 1,1-dimethylethyl; $C_{1-6}$alkyl defines $C_{1-4}$alkyl radicals as defined hereinbefore and the higher homologs thereof having from 5 to 6 carbon atoms such as, for example, pentyl and hexyl; $C_{3-6}$alkenyl defines straight and branched chain hydrocarbon radicals containing one double bond and having from 3 to 6 carbon atoms such as, for example, 2-propenyl, 2-butenyl, 3-butenyl, 2-methyl-2-propenyl, 2-pentenyl, 3-pentenyl, 3,3-dimethyl-2-propenyl, hexenyl and the like; $C_{1-4}$alkanediyl defines bivalent straight or branched chain hydrocarbon radicals containing from 1 to 4 carbon atoms such as, for example, methylene, 1,1-ethanediyl, 1,2-ethanediyl, 1,3-propanediyl, 1,4-butanediyl and the like.

The term pharmaceutically acceptable addition salt as used hereinbefore defines the nontoxic, therapeutically active addition salt forms which the compounds of formula (I) may form. The compounds of formula (I) having basic properties may be converted into the corresponding therapeutically active, non-toxic acid addition salt forms by treating the free base form with a suitable amount of an appropriate acid following conventional procedures. Examples of appropriate acids are for example, inorganic acids, for example, hydrohalic acid, e.g. hydrochloric, hydrobromic and the like acids, sulfuric acid, nitric acid, phosphoric acid and the like; or organic acids, such as, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids.

The compounds of formula (I) having acidic properties may be converted in a similar manner into the corresponding therapeutically active, non-toxic base addition salt forms. Examples of such base addition salt forms are, for example, the sodium, potassium, calcium salts, and also the salts with pharmaceutically acceptable amines such as, for example, ammonia, alkylamines, benzathine, $\underline{N}$-methyl-D-glucamine, hydrabamine, amino acids, e.g. arginine, lysine. The term pharmaceutically acceptable addition salts also comprises the solvates which the compounds of formula (I) may form, e.g. the hydrates, alcoholates and the like.

The term stereochemically isomeric forms as used hereinbefore defines the possible different isomeric as well as conformational forms which the compounds of formula (I) may possess. Unless otherwise mentioned or indicated, the chemical designation of compounds denotes the mixture of all possible stereochemically and conformationally isomeric forms, said mixtures containing all diastereomers, enantiomers and/or conformers of the basic molecular structure. All stereochemically isomeric forms of the compounds of formula (I) both in pure form or in admixture with each other are intended to be embraced within the scope of the present invention.

Some compounds of the present invention may exist in different tautomeric forms and all such tautomeric forms are intended to be included within the scope of the present invention.

Interesting compounds are those compounds of formula (I) wherein each of the dotted lines independently represents an optional bond;

$R^1$ represents hydrogen, halo or $C_{1-4}$alkyl;

$R^2$ represents hydrogen, halo, $C_{1-4}$alkyl or $C_{1-4}$alkyloxy;

$R^3$ represents hydrogen, $C_{1-4}$alkyl, hydroxy$C_{1-4}$alkyl, formyl or hydroxycarbonyl;

$R^4$ represents hydrogen, $C_{1-4}$alkyl, hydroxy$C_{1-4}$alkyl, phenyl or halo;

$R^5$ represents hydrogen;

L represents hydrogen; $C_{1-6}$alkyl; $C_{1-6}$alkyl substituted with hydroxy, $C_{1-4}$alkyloxy, $C_{1-4}$alkyloxycarbonylamino, $C_{1-4}$alkylaminocarbonyl, $C_{1-4}$alkylaminocarbonylamino, $C_{1-4}$alkylaminothiocarbonylamino, aryl or aryloxy; $C_{3-6}$alkenyl; $C_{3-6}$alkenyl substituted with aryl;

wherein each aryl is phenyl or phenyl substituted with halo, $C_{1-4}$alkyl or $C_{1-4}$alkyloxy; or, L represents a radical of formula —Alk—Y—Het$^1$ (a-1), —Alk—NH—CO—Het$^2$ (a-2), or —Alk—Y—Het$^3$ (a-3); wherein Alk represents $C_{1-4}$alkanediyl;

Y represents O, S or NH;

Het$^1$, Het$^2$ and Het$^3$ each represent furanyl, thienyl, pyrrolyl, oxazolyl, thiazolyl or imidazolyl each optionally substituted with one or two $C_{1-4}$alkyl substituents; thiadiazolyl or oxadiazolyl optionally substituted with amino or $C_{1-4}$alkyl; pyridinyl, pyrimidinyl, pyrazinyl or pyridazinyl each optionally substituted with $C_{1-4}$alkyl, $C_{1-4}$alkyloxy, amino, hydroxy or halo; imidazo[4,5-c]pyridin-2-yl; and Het$^3$ may also represent 4,5-dihydro-5-oxo-1$\underline{H}$-tetrazolyl substituted with $C_{1-4}$alkyl, 2-oxo-3-oxazolidinyl, 2,3-dihydro-2-oxo-1$\underline{H}$-benzimidazol-1-yl or a radical of formula

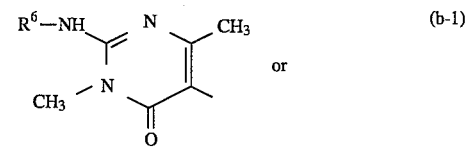 (b-1)

or

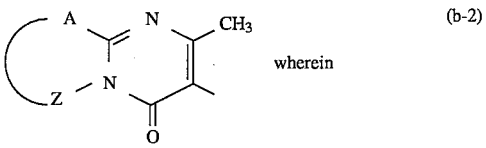 (b-2)

wherein $R^6$ represents hydrogen or $C_{1-4}$alkyl; and

A-Z represents —S—CH=CH—, —S—CH$_2$—CH$_2$—, —S—CH$_2$— CH$_2$—CH$_2$—, —CH=CH— CH=CH— or CH$_2$—CH$_2$—CH$_2$—CH$_2$;

provided that 6,11-dihydro-11-(4-piperidinylidene)-5$\underline{H}$-imidazo[2,1-b] [3]benzazepine is ecxluded.

Another group of interesting compounds comprises those compounds of formula (I) wherein L is $C_{1-4}$alkyl or $C_{1-4}$alkyl substituted with hydroxycarbonyl or $C_{1-4}$alkyloxycarbonyl.

Further interesting compounds are those compounds of formula (I) wherein $R^1$, $R^2$, $R^3$, $R^4$ and $R^5$ represent hydrogen.

Yet another group of interesting compounds of formula (I) are those of formula

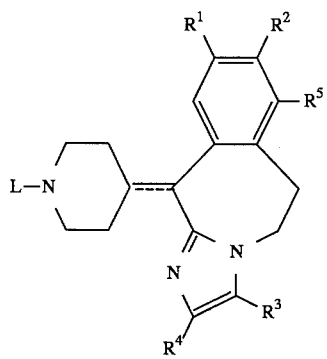

wherein $R^1$, $R^2$, $R^3$, $R^4$, $R^5$ and L are as defined under formula (I).

Preferred compounds are those compounds of formula (I) wherein $R^3$ represents hydrogen, $C_{1-4}$alkyl, formyl, hydroxy$C_{1-4}$alkyl or hydroxycarbonyl;

$R^4$ represents hydrogen, halo or hydroxy$C_{1-4}$alkyl; and

L represents hydrogen, $C_{1-4}$alkyl, halo$C_{1-4}$alkyl, hydroxycarbonyl$C_{1-4}$alkyl, $C_{1-4}$alkyloxycarbonyl$C_{1-4}$alkyl, $C_{1-4}$alkyloxycarbonylamino$C_{1-4}$alkyl, aryl-$C_{1-4}$alkyl, propenyl, or L is a radical of formula (a-1), (a-2) or (a-3), wherein $Het^1$, $Het^2$, and $Het^3$ each represent furanyl, oxazolyl or thiazolyl each optionally substituted with $C_{1-4}$alkyl; thiadiazolyl optionally substituted with amino, pyridinyl; or pyrimidinyl each optionally substituted with hydroxy; imidazo[4,5-c]pyridin-2-yl; and $Het^3$ may also represent a radical of formula (b-2).

More preferred compounds are those preferred compounds wherein $R^1$ represents hydrogen or halo;

$R^2$ represents hydrogen, halo or $C_{1-4}$alkyloxy; and

L represents hydrogen, $C_{1-4}$alkyl, halo$C_{1-4}$alkyl, hydroxycarbonyl$C_{1-4}$alkyl, $C_{1-4}$alkyloxycarbonyl$C_{1-4}$alkyl, or a radical of formula (a-1), wherein Y represents NH.

Still more preferred are those more preferred compounds wherein $R^4$ represents hydrogen or halo; and L represents hydrogen, $C_{1-4}$alkyl, hydroxycarbonyl$C_{1-4}$alkyl, $C_{1-4}$alkyloxycarbonyl$C_{1-4}$alkyl or a radical of formula (a-1), wherein $Het^1$ is thiazolyl, or imidazo[4,5-c]pyridin-2-yl.

The most preferred compounds are:

5,6-dihydro-11-(1-methyl-4-piperidinylidene )-11H-imidazo[2, 1-b][3]benzazepine; 9-fluoro-6,11-dihydro-11-(1-methyl-4-piperidinylidene)-5 H-imidazo[2,1-b][3]-benzazepine;

11-(1-methyl-4-piperidinylidene )-11H-imidazo[2, 1-b][3]benzazepine;

6,11-dihydro-11-(1-methyl-4-piperidinylidene)-5 H-imidazo[ 2,1-b][3]benzazepine-3methanol;

8-fluoro-6,11-dihydro-11-(1-methyl-4-piperidinylidene)-5H-imidazo[ 2,1-b][3]benzazepine;

6,11-dihydro-11-(1-methyl-4-piperidinylidene)-5 H-imidazo[ 2,1-b][3]benzazepine-3-carboxaldehyde;

6,11-dihydro-11-(1-methyl-4-piperidinylidene)-5 H-imidazo[ 2,1-b][3]benzazepine-3-carboxylic acid;

7-fluoro-6,11-dihydro-11-(1-methyl-4-piperidinylidene)-5H-imidazo[ 2,1-b][3]benzazepine;

4-(8-fluoro-5,6-dihydro-11 H-imidazo[2,1-b][3]benzazepin-11 -ylidene)-1-piperidinepropanoic acid dihydrate, the stereoisomers and the pharmaceutically acceptable acid-addition salts thereof.

In the following paragraphs there are described different ways of preparing the compounds of formula (I). In order to simplify the structural formulae of the compounds of formula (I) and the intermediates intervening in their preparation, the imidazo[2,1-b] [3]benzazepine moiety will be represented by the symbol T hereinafter.

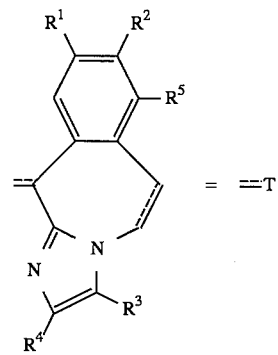

The compounds of formula (I) can be prepared by cyclizing an alcohol of formula (II) or a ketone of formula (III).

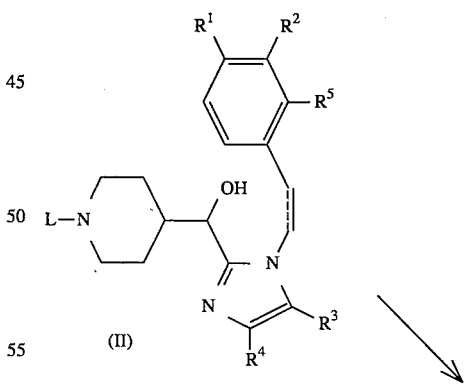

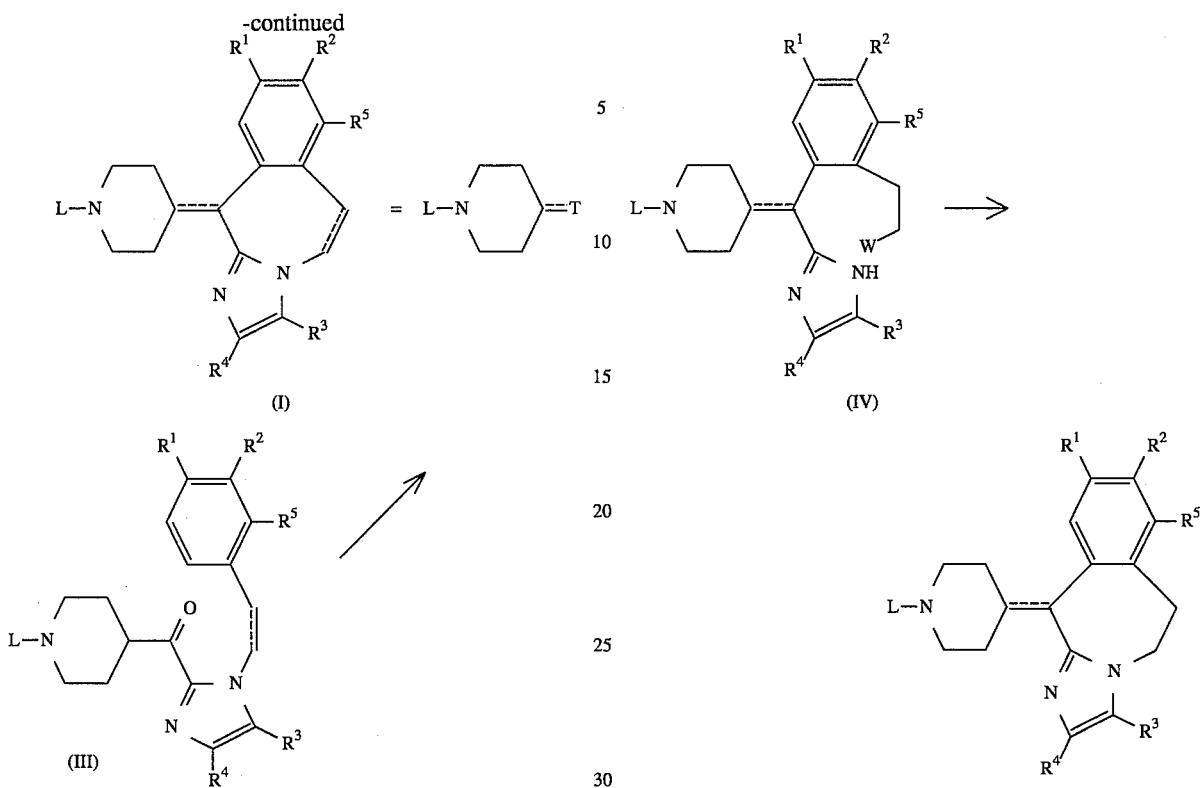

Said cyclization reaction is conveniently conducted by treating the intermediate of formula (II) or (III) with an appropriate acid, thus yielding a reactive intermediate which cyclizes to a compound of formula (I). Appropriate acids are, for example, strong acids, in particular superacid systems, e.g. methanesulfonic acid, trifluoromethanesulfonic acid, trifluoroacetic acid, methanesulfonic acid/boron trifluoride, hydrofluoric acid/boron trifluoride, or Lewis acids, e.g. aluminum chloride and the like. Obviously, only those compounds of formula (I) wherein L is stable under the given reaction conditions can be prepared according to the above reaction procedure. In case of superacids the reaction is preferably conducted in an excess of said acid; in case of solid Lewis acids, e.g. aluminum chloride, the reaction can be conducted by fusing the starting material and the reagent, preferably in the presence of an additional salt such as sodium chloride. The cyclodehydration reaction with trimethylsilyl iodide is conveniently conducted in a reaction-inert solvent such as, for example, a halogenated hydrocarbon, e.g. trichloromethane. Particularly noteworthy is the fact that the latter reaction also can be performed on intermediates of formula (II) or (III) wherein L represents $C_{1-4}$alkyloxycarbonyl; in this case—besides cyclodehydration—also cleavage of the carbamate is observed and a compound of formula (I) wherein L is hydrogen is obtained.

In the foregoing and following preparations, the reaction mixture is worked up following art-known methods and the reaction product is isolated and, if necessary, further purified.

The compounds of formula (I) wherein the central ring of the tricyclic moiety does not contain an optional bond may also be prepared by cyclizing an intermediate of formula (IV).

In formula (IV) and hereinafter W represents an appropriate leaving group such as, for example, halo, e.g. chloro, bromo and the like; or a sulfonyloxy group such as, for example, methansulfonyloxy, 4-methylbenzenesulfonyloxy and the like.

Said cyclization reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; a halogenated hydrocarbon, e.g. dichloromethane, 1,2-dichloroethane and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, NN-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction.

Alternatively, the compounds of formula (I) wherein a double bond exists between the piperidinyl and the imidazo [2,1-b][3]benzazepine moiety, said compounds being represented by formula (I-a), can be prepared by dehydrating an alcohol of formula (V) or (VI).

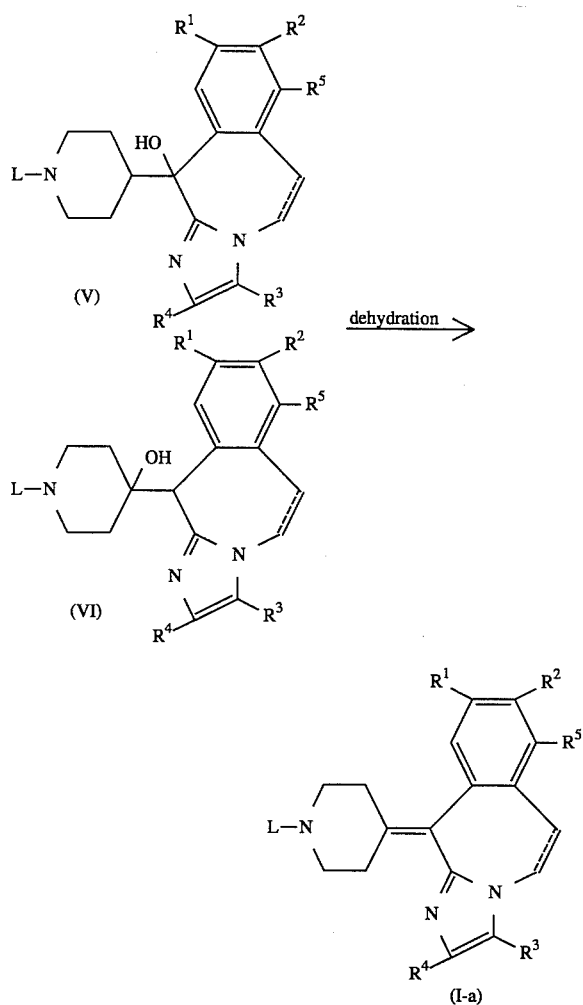

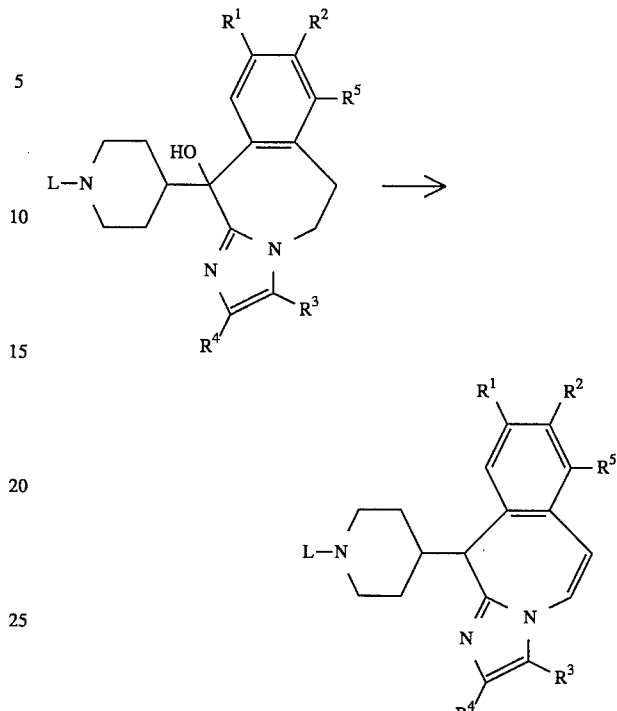

Said dehydration reaction can conveniently be conducted employing conventional dehydrating reagents following art-known methodologies. Appropriate dehydrating reagents are, for example, acids, e.g. sulfuric acid, phosphoric acid, hydrochloric acid, methanesulfonic acid, carboxylic acids, e.g. acetic acid, trifluoroacetic acid and mixtures thereof; anhydrides, e.g. acetic anhydride, phosphorus pentoxide and the like; other suitable reagents, e.g. zinc chloride, thionyl chloride, boron trifluoride etherate, phosphoryl chloride pyridine, potassium bisulfate, potassium hydroxide. In some instances said dehydration reaction may require heating the reaction mixture, more particularly up to the reflux temperature. Again, only those compounds of formula (I-a) wherein L is stable under the given reaction conditions can be prepared according to the above reaction procedure. Particularly noteworthy is the fact that the latter reaction when performed on intermediate (V) wherein the dotted line does not represent an optional bond, in some instances may also yield a compound of formula (I) with a double bond in the tricyclic moiety and a single bond bridging the tricyclic moiety and the piperidine:

The compounds of formula (I) wherein L is $C_{1-6}$alkyl, said compounds being represented by the formula (I-b) can be converted into the compounds of formula (I), wherein L is hydrogen, said compounds being represented by the formula (I-c) in a number of manners. A first method involves dealkylating-carbonylating the compounds of formula (I-b) with a $C_{1-4}$alkylchloroformate and subsequently hydrolyzing the thus obtained compound of formula (VII-a).

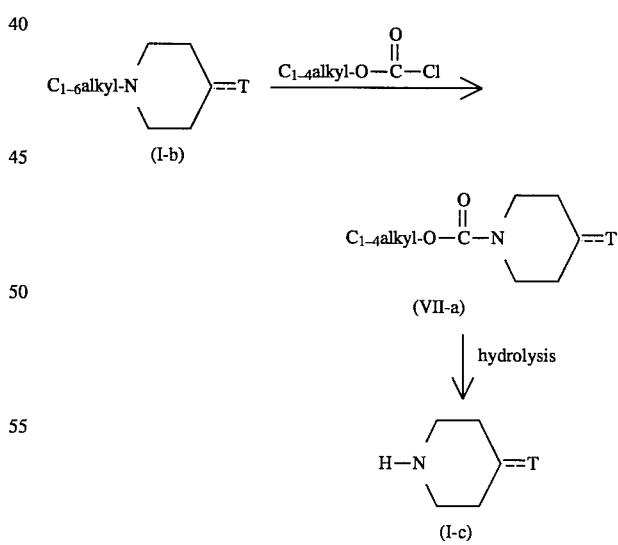

The reaction with the $C_{1-4}$alkylchloroformate is conveniently conducted by stirring and heating the starting material (I-b) with the reagent in an appropriate solvent and in the presence of a suitable base. Appropriate solvents are, for example, aromatic hydrocarbons, e.g. methylbenzene, dimethylbenzene, chlorobenzene; ethers, e.g. 1,2-dimethoxyethane, and the like solvents. Suitable bases are, for example, alkali or earth alkaline metal carbonates, hydrogen carbonates, hydroxides, or organic bases such as, N,N-diethylethanamine, N-(1-methylethyl)-2-propanamine, and the like.

The compounds of formula (VII-a) are hydrolyzed in acidic or basic media following conventional methods. For example, concentrated acids such as hydrobromic, hydrochloric acid or sulfuric acid can be used, or alternatively bases such as alkali metal or earth alkaline metal hydroxides in water, an alkanol or a mixture of water-alkanol may be used. Suitable alkanols are methanol, ethanol, 2-propanol and the like. In order to enhance the rate of the reaction it is advantageous to heat the reaction mixture, in particular up to the reflux temperature.

The compounds of formula (I-b) may also be converted directly into the compounds of formula (I-c) by stirring and heating them with an α-halo-$C_{1-4}$alkyl chloroformate in an appropriate solvent such as, for example, a halogenated hydrocarbon, e.g. dichloromethane, trichloromethane; an aromatic hydrocarbon, e.g. methylbenzene, dimethylbenzene; an ether, e.g. 1,2-dimethoxyethane; an alcohol, e.g. methanol, ethanol, 2-propanol, optionally in the presence of a base such as, for example, an alkali or earth alkaline metal carbonate, hydrogen carbonate, hydroxide or an amine, e.g. N,N-diethylethanamine, N-(1-methylethyl)-2-propanamine, and the like.

The compounds of formula (I-c) can also be prepared by debenzylating a compound of formula (I-d) by catalytic hydrogenation in the presence of hydrogen and an appropriate catalyst in a reaction-inert solvent.

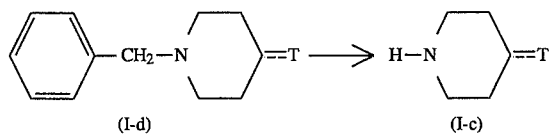

A suitable catalyst in the above reaction is, for example, platinum-on-charcoal, palladium-on-charcoal, and the like. An appropriate reaction-inert solvent for said debenzylation reaction is, for example, an alcohol, e.g. methanol, ethanol, 2-propanol and the like, an ester, e.g. ethylacetate and the like, an acid, e.g. acetic acid and the like.

The compounds of formula (I) wherein L is other than hydrogen, said compounds being represented by formula (I-e) and said L by $L^1$, can be prepared by N-alkylating the compounds of formula (I-c) with a reagent of formula $L^1$-W (VIII).

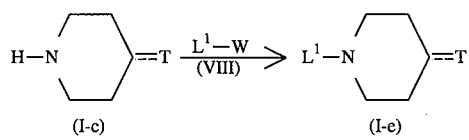

Said N-alkylation reaction can conveniently be conducted in a reaction-inert solvent such as, for example, an aromatic hydrocarbon, e.g., benzene, methylbenzene, dimethylbenzene and the like; an alkanol, e.g., methanol, ethanol, 1-butanol and the like; a ketone, e.g., 2-propanone, 4-methyl-2-pentanone and the like; an ether, e.g., tetrahydrofuran, 1,4-dioxane, 1,1'-oxybisethane and the like; a dipolar aprotic solvent, e.g., N,N-dimethylformamide, N,N-dimethylacetamide, dimethyl sulfoxide, nitrobenzene, 1-methyl-2-pyrrolidinone and the like; a halogenated hydrocarbon, e.g. dichloromethane, 1,2-dichloroethane and the like; or a mixture of such solvents. The addition of an appropriate base such as, for example, an alkali or an earth alkaline metal carbonate, hydrogen carbonate, alkoxide, hydride, amide, hydroxide or oxide, e.g., sodium carbonate, sodium hydrogen carbonate, potassium carbonate, sodium methoxide, sodium ethoxide, potassium tert. butoxide, sodium hydride, sodium amide, sodium hydroxide, calcium carbonate, calcium hydroxide, calcium oxide and the like; or an organic base, such as, for example, an amine, e.g., N,N-diethylethanamine, N-(1-methylethyl)-2-propanamine, 4-ethylmorpholine, pyridine and the like may be utilized to pick up the acid which is liberated during the course of the reaction. In some instances the addition of an iodide salt, preferably an alkali metal iodide, is appropriate. Somewhat elevated temperatures and stirring may enhance the rate of the reaction. Alternatively, said N-alkylation may be carried out by applying art-known conditions of phase transfer catalysis reactions.

The compounds of formula (I) wherein L is $C_{1-6}$alkyl or substituted $C_{1-6}$alkyl, said L being represented by the radical $L^2H$- and said compounds by formula (I-f), can also be prepared by reductive N-alkylation of the compounds of formula (I-c) with an appropriate ketone or aldehyde of formula $L^2$=O (IX). $L^2$=O represents an intermediate of formula $L^2H_2$ wherein two geminal hydrogen atoms have been replaced by oxygen (=O) and $L^2$ is a geminal bivalent $C_{1-6}$alkylidene radical which optionally may be substituted.

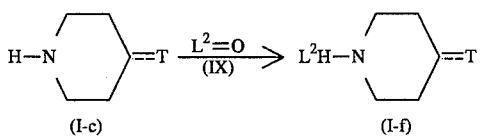

Said reductive N-alkylation reaction may conveniently be carried out by reducing a mixture of the reactants in a suitable reaction-inert solvent following art-known reductive N-alkylation procedures. In particular, the reaction mixture may be stirred and/or heated in order to enhance the reaction rate. Suitable solvents are, for example, water; $C_{1-6}$alkanols, e.g. methanol, ethanol, 2-propanol and the like; esters, e.g. ethyl acetate, γ-butyrolactone and the like; ethers, e.g. 1,4-dioxane, tetrahydrofuran, 1,1'-oxybisethane, 2-methoxyethanol and the like; halogenated hydrocarbons, e.g. dichloromethane, trichloromethane and the like; dipolar aprotic solvents, e.g. N,N-dimethylformamide, dimethyl sulfoxide and the like; carboxylic acids, e.g. acetic acid, propanoic acid and the like; or a mixture of such solvents. The term "art-known reductive N-alkylation procedures" means that the reaction is carried out either with sodium cyanoborohydride, sodium borohydride, formic acid or a salt thereof, e.g. ammonium formate and the like reducing agents, or alternatively under hydrogen atmosphere, optionally at an increased temperature and/or pressure, in the presence of an appropriate catalyst such as, for example, palladium-on-charcoal, platinum-on-charcoal and the like. In order to prevent the undesired further hydrogenation of certain functional groups in the reactants and the reaction products, it may be advantageous to add an appropriate catalyst-poison to the reaction mixture, e.g., thiophene, quinoline-sulphur and the like. In some instances it may also be advantageous to add an alkali metal salt to the reaction mixture such as, for example, potassium fluoride, potassium acetate and the like salts.

The compounds of formula (I) wherein L represents a radical $Het^3$-$C_{2-4}$alkyl, said compounds being represented by formula (I-g) can be prepared by the addition reaction of a compound of formula (I-c) to an appropriate alkene of formula (X).

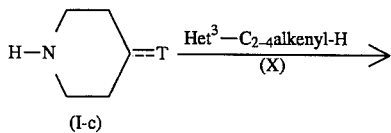

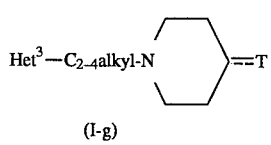

The compounds wherein L is 2-hydroxy-$C_{2-6}$alkyl, or aryloxy-2-hydroxy-$C_{2-6}$alkyl said compounds being represented by formula (I-h), can be prepared by reacting a compound of formula (I-c) with an epoxide (XI) wherein $R^7$ represents hydrogen, $C_{1-4}$alkyl or aryloxy$C_{1-4}$alkyl.

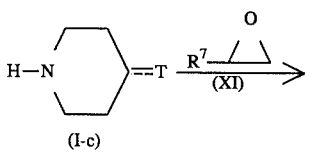

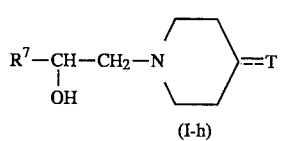

The reaction of (I-c) with respectively (X) or (XI) can be conducted by stirring and, if desired, heating the reactants in a reaction-inert solvent such as, for example, a ketone, e.g. 2-propanone, 4-methyl-2-pentanone; an ether, e.g. tetrahydrofuran; an alcohol, e.g. methanol, ethanol, 1-butanol; a dipolar aprotic solvent, e.g. N,N-dimethylformamide and the like.

The compounds of formula (VII-b) can be prepared from a compound of formula (I-i) wherein L represents P—NH—$C_{2-4}$alkyl and P is a protective group such as, for example, $C_{1-4}$alkyloxycarbonyl, following art-known deprotection methods.

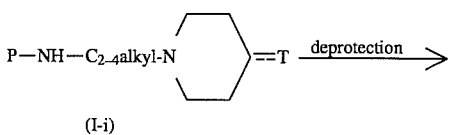

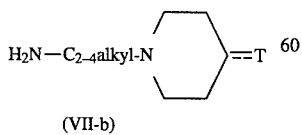

The compounds of formula (VII-b) can also be prepared by reducing a compound of formula (VII-c).

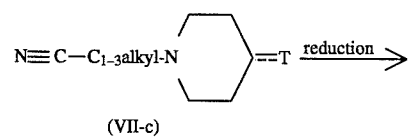

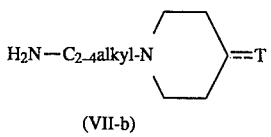

Said reduction can be conducted by stirring and, if desired, heating the starting material in a hydrogen containing medium in the presence of a catalyst, e.g. palladium-on-charcoal, platinum-on-charcoal, Raney Nickel and the like, in a suitable solvent, e.g. methanol, ethanol and the like, or by reduction with a metal hydride, e.g. lithium aluminum hydride in an ether, e.g. tetrahydrofuran.

The compounds of formula (I) wherein L is a radical of formula —Alk—Y-Het$^1$, said compounds being represented by formula (I-j), can be prepared by alkylating a compound of formula (I-k) with a reagent of formula (XII).

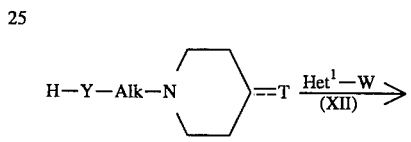

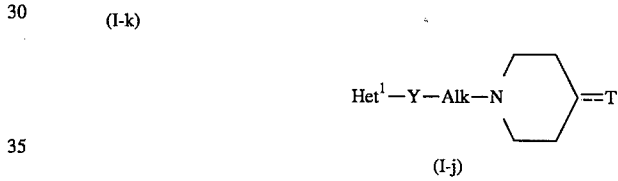

Alternatively, the compounds of formula (I-j) can also be prepared by reacting a compound of formula (VII-d) with a reagent of formula (XIII).

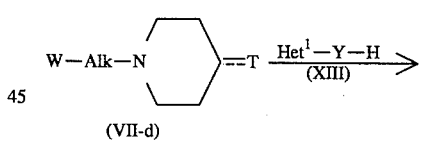

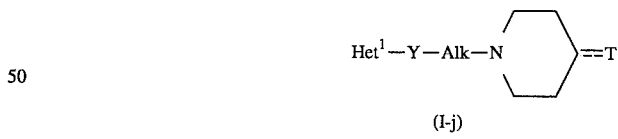

The above alkylation reactions may conveniently be conducted in a reaction-inert solvent, e.g. methylbenzene, dimethylbenzene, 2-propanone, 4-methyl-2-pentanone, 1,4-dioxane, tetrahydrofuran, N,N-dimethylformamide, N,N-dimethylacetamide, methanol, ethanol, 1-butanol and the like. The addition of an appropriate base, e.g. an alkali metal or earth alkaline metal carbonate or hydrogen carbonate, sodium hydride, N,N-diethylethanamine or N-(1-methylethyl)-2-propanamine may be used to pick up the acid liberated during the course of the reaction. In some instances the addition of an iodide salt, preferably an alkali metal iodide, is appropriate. In order to enhance the rate of the reaction the reaction mixture may be heated.

The compounds of formula (I) wherein L represents a radical of formula —Alk—NH—CO—Het², said compounds being represented by formula (I-1) can be prepared by N-acylating a compound of formula (VII-b) with a carboxylic acid of formula (XIV) or a reactive functional derivative thereof.

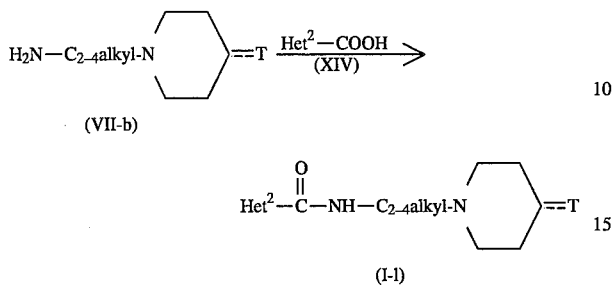

(I-1)

The reaction of (XIV) with (VII-b) may generally be conducted following art-known amidation reaction procedures. For example, the carboxylic acid may be converted into a reactive derivative, e.g. an anhydride or a carboxylic acid halide, which subsequently is reacted with (VII-b); or by reacting (XIV) and (VII-b) with a suitable reagent capable of forming amides, e.g., N,N-methanetetraylbis[cyclohexamine], 2-chloro-1-methylpyridinium iodide and the like. Said reactions are conveniently conducted in a suitable solvent such as, for example, an ether, e.g., tetrahydrofuran, a halogenated hydrocarbon, e.g., dichloromethane, trichloromethane, a dipolar aprotic solvent and the like. The addition of a base such as, for example, N,N-diethylethanamine and the like may be appropriate.

The compounds of formula (I) wherein L represents $C_{1-4}$alkylamino(thio)carbonylamino-$C_{1-4}$alkyl, said compounds being represented by the formula (I-m), can be prepared from the compounds of formula (VII-b) by reaction with a $C_{1-4}$alkyliso(thio)cyanate in a reaction-inert solvent such as, for example, an ether, e.g. tetrahydrofuran.

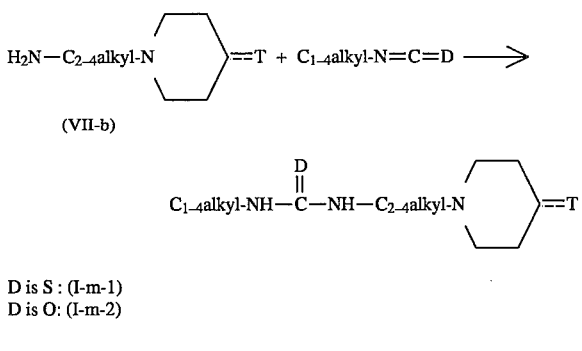

D is S : (I-m-1)
D is O: (I-m-2)

The compounds of formula (I) wherein Het¹ represents an imidazo[4,5-c]pyridin-2-yl radical and Y represents NH, said compounds being represented by formula (I-n) can be prepared from a compound of formula (VII-b) according to the following reaction scheme.

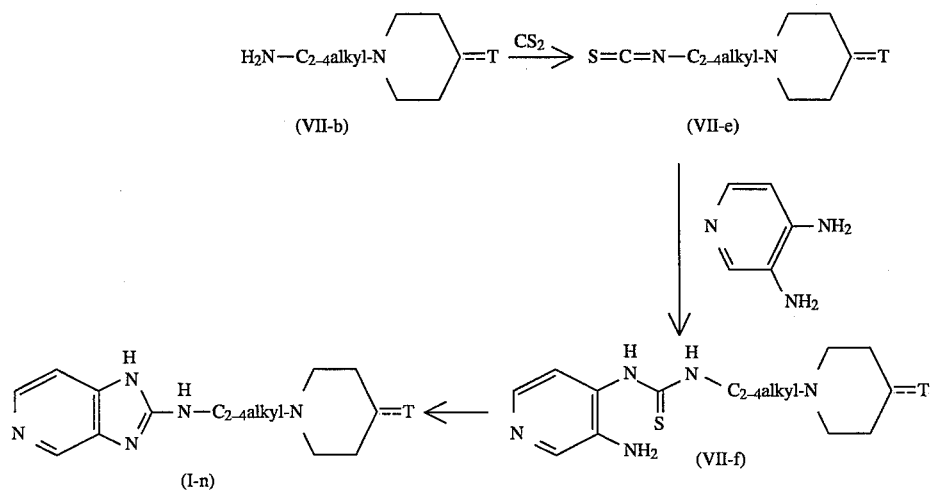

The isocyanate (VII-e) is prepared by reacting (VII-b) with carbon disulfide in the presence of a dehydrating reagent such as N,N-methanetetraylbis[cyclohexanamine] in a reaction-inert solvent such as an ether, e.g. tetrahydrofuran. The isothiocyanate is reacted with 3,4-diaminopyridine in a reaction-inert solvent such as an ether, e.g. tetrahydrofuran, and the resulting thiourea is cyclized by treatment with an appropriate metal oxide such as mercury(II)oxide. In certain instances if may be appropriate to supplement the reaction mixture with a small amount of sulfur.

The compound (VII-e) or the corresponding isocyanate can also be employed to prepare compounds of formula (I-m), by reacting (VII-e) or the corresponding isocyanate with a $C_{1-4}$alkylamine in a reaction-inert solvent such as an ether, e.g. tetrahydrofuran.

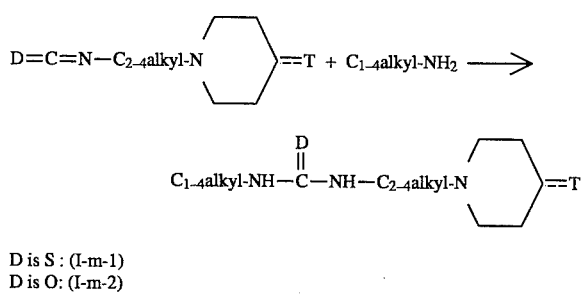

D is S : (I-m-1)
D is O : (I-m-2)

The compounds of formula (I) wherein Het¹ represents an imidazole and Y represents NH, said compounds being represented by formula (I-o) can be prepared from the compounds (VII-b) according to the following reaction scheme.

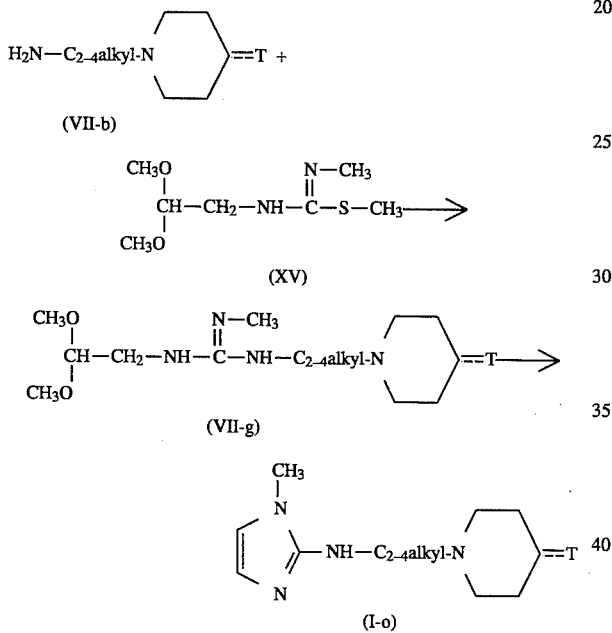

The compound (VII-b) is reacted with a reagent of formula (XV) in a reaction-inert solvent such as an alcohol, e.g. 2-propanol and the thus obtained intermediate (VII-g) is cyclized by treatment with an acidic aqueous solution, such as a hydrochloric acid aqueous solution.

The compounds of formula (I) wherein $R^3$ and/or $R^4$ represent hydroxymethyl can be prepared by formylating the compounds of formula (I), wherein $R^3$ and/or $R^4$ are hydrogen, said compounds being represented by the formula (I-p) with formaldehyde, optionally in the presence of an appropriate carboxylic acid-carboxylate mixture such as, for example, acetic acid-sodium acetate and the like. In order to enhance the rate of the reaction, the reaction mixture is advantageously heated up to the reflux temperature.

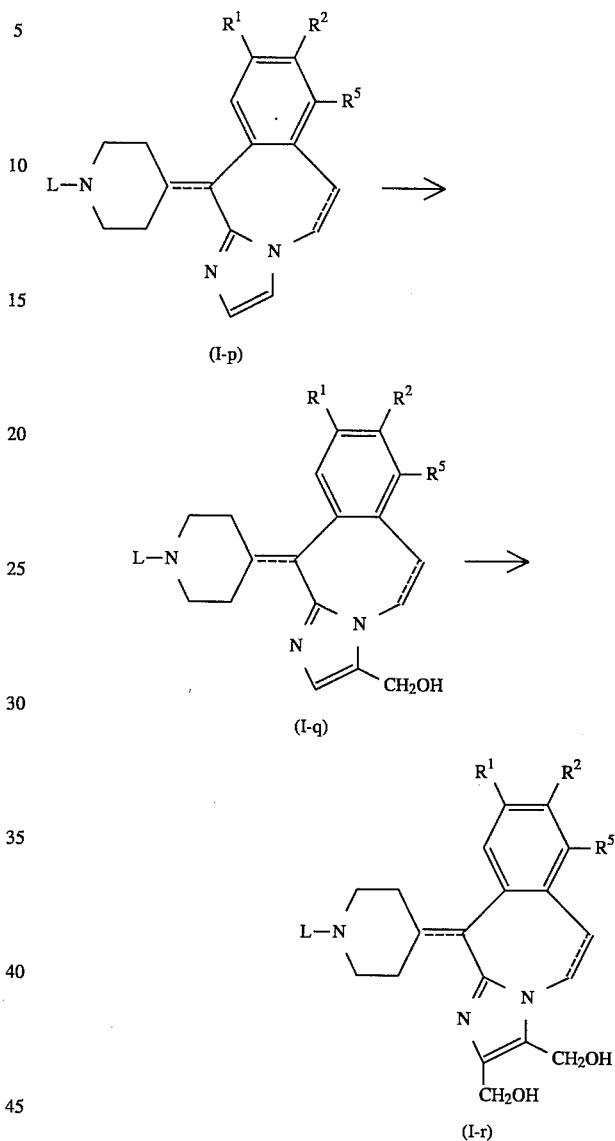

The thus obtained compounds (I-q) and (I-r) can be further oxidized to the corresponding aldehyde or carboxylic acid by reaction with suitable reagents such as, for example, manganese(IV)oxide, respectively, silver nitrate.

The compounds of formula (I) wherein $R^4$ is halo, said compounds being represented by formula (I-s), can be prepared by halogenating the compounds of formula (I), wherein $R^4$ is hydrogen, said compounds being represented by the formula (I-t).

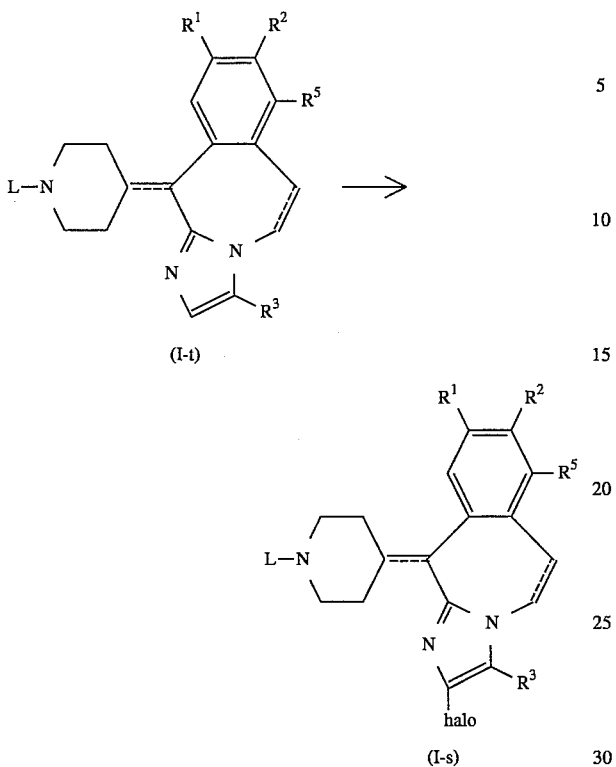

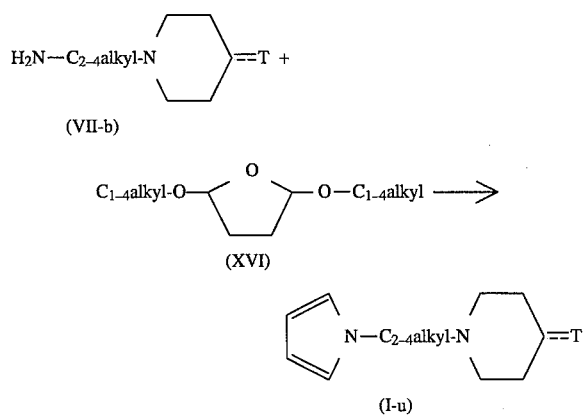

Said halogenation reaction can conveniently be conducted by treating the starting material with dihalide in an appropriate solvent such as, for example, a carboxylic acid, e.g. acetic acid, optionally in admixture with a carboxylate salt, e.g. sodium acetate. In order to enhance the rate of the reaction, the reaction mixture may be heated.

The compounds of formula (I) wherein $Het^3$ represents a pyrrolyl radical, said compounds being represented by the formula (I-u), can be prepared by reacting a compound of formula (VII-b) with a reagent of formula (XVI).

In a similar way, the compounds of formula (I) wherein $Het^3$ represents a 2-$C_{1-4}$alkyloxycarbonyl-1-pyrrolyl radical, said compounds being represented by the formula (I-v), can be prepared by reacting a compound of formula (VII-b) with a reagent of formula (XVII).

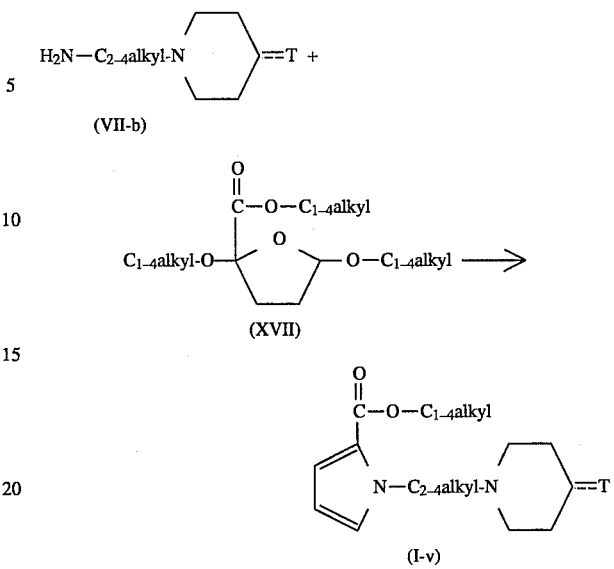

The above reactions of (VII-b) with (XVI) and (XVII), respectively, preferably are conducted in the presence of an acid, such as, for example, acetic acid.

Further, the compounds of formula (I-u) may be converted in the corresponding aldehyde and alcohol compounds, said compounds being represented by the formulae (I-w) and (I-x), respectively, by the following reaction sequence.

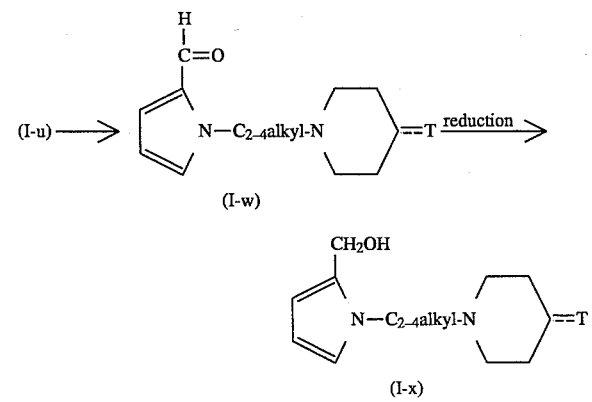

The formylation of (I-u) into (I-w) can conviently be conducted in a reaction-inert solvent such as, for example, a dipolar aprotic solvent, e.g. N,N-dimethylformamide, N,N-dimethylacetamide and the like, in the presence of a formylating reagent such as, for example, phosphoryl chloride, zinc cyanide and hydrochloric acid, trichloromethane and hydroxide ions, and the like. The compounds of formula (I-w) can be reduced into the compounds of formula (I-x) in a reaction-inert solvent, such as, for example, an alcohol, e.g. methanol, ethanol, 2-propanol and the like in the presence of an appropriate reductant, such as, for example, metallic hydrides, e.g. lithium aluminium hydride, sodium borohydride, sodium cyanoborohydride, and the like.

The compounds of formula (I-v) and (I-w), can be converted in the corresponding compounds of formula (I) wherein $Het^3$ is a 2-hydroxycarbonyl-1-pyrrolyl radical by the hydrolysis of (I-v) in the presence of an acid or a base, or oxidation of (I-w) in the presence of a suitable oxidizing reagent.

The compounds of formula (I) wherein $R^3$ is $C_{1-4}$alkyloxycarbonylethenyl, said compounds being represented by the formula (I-y), can be prepared by reacting a compound of formula (I) wherein $R^3$ is formyl, said compounds being represented by the formula (I-z) with a reagent of formula (XVIII) in the presence of a base e.g. piperidine, pyridine, and the like.

hydroxycarbonyl moiety in the presence of an acid or a base.

The compounds of formula (I) wherein L is $C_{1-4}$alkyloxyphenyl$C_{1-6}$alkyl can be converted into a compound of formula (I) wherein L is hydroxyphenyl$C_{1-6}$alkyl upon treatment with an acid, such as, for example, hydrobromic acid, hydroiodic acid or a Lewis acid, e.g. borontrifluoride, aluminiumtrichloride and the like.

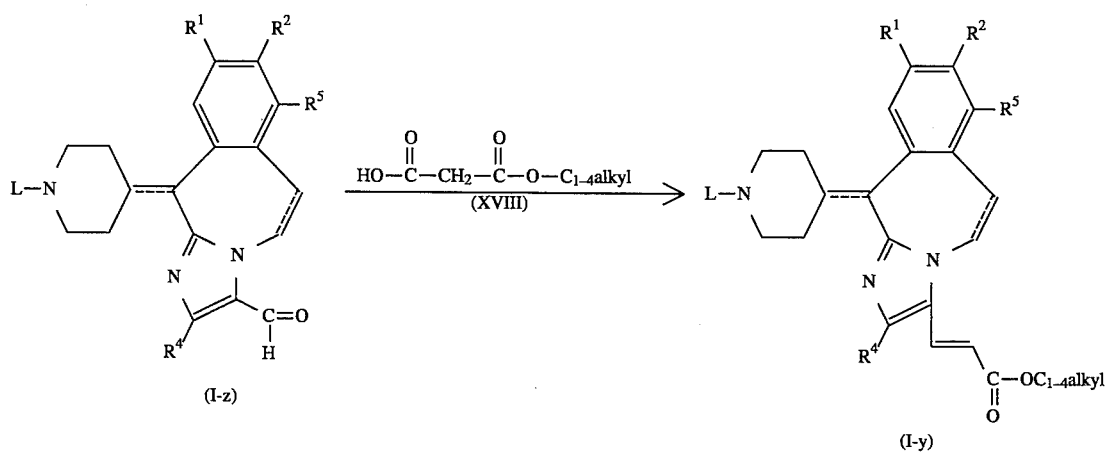

The compounds of formula (I-y) can be further hydrolyzed into a compound of formula (I) wherein $R^3$ is hydroxycarbonylethenyl, in the presence of an acid or a base. The compounds of formula (I) wherein $R^3$ is methoxycarbonylmethyl, said compounds being represented by the formula (I-aa), can be prepared by reacting a compound of formula (I-z) with a reagent of formula (XIX) in the presence of benzyltrimethyl ammonium hydroxide in a reaction-inert solvent e.g. tetrahydrofuran.

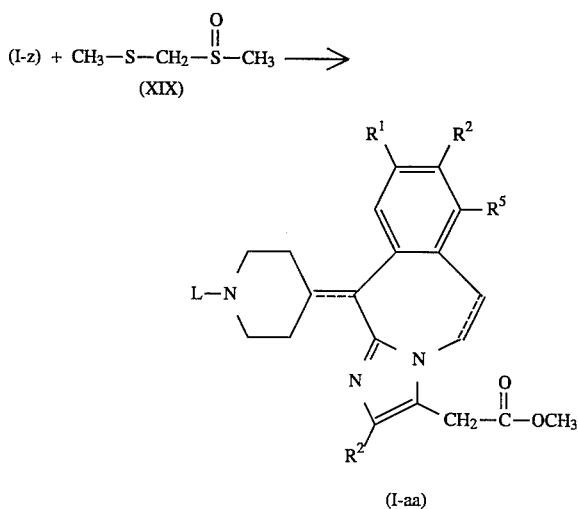

The compounds of formula (I-aa) can be further hydrolyzed into a compound of formula (I) wherein $R^3$ is hydroxycarbonylmethyl, in the presence of an acid or a base.

The compounds of formula (I) may further be converted into each other following art-known functional group transformation procedures.

For example, the compounds of formula (I) wherein L contains a $C_{1-4}$alkyloxycarbonyl moiety can be hydrolyzed into a compound of formula (I) wherein L contains a The compounds of formula (VII-a to VII-g) intervening in the preparations described hereinbefore are novel and have especially been developed for use as intermediates in said preparations. Consequently, the present invention also relates to novel compounds of formula

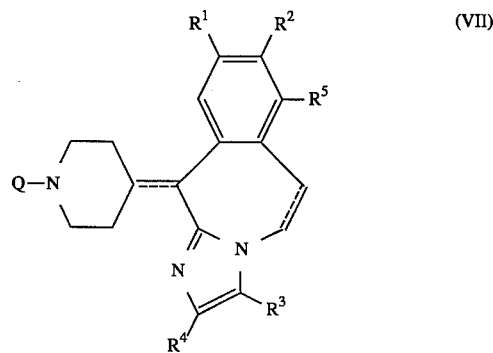

the addition salt forms thereof and the stereochemically isomeric forms thereof, wherein each of the dotted lines independently represents an optional bond, $R^1$, $R^2$, $R^3$, $R^4$ and $R^5$ are as defined under formula (I); and Q is ($C_{1-6}$alkyl or phenyl)oxycarbonyl, $C_{1-4}$alkylcarbonyl or $C_{1-6}$alkyl substituted with halo, cyano, amino, isothiocyanato, (4-amino-3-pyridinyl)aminothiocarbonylamino, $(CH_3O)_2CH—CH_2—NH—C(=NCH_3)—NH—$ or methylsulfonyloxy; provided that 1-acetyl-4-(5,6-dihydro-11H-imidazol[1,2-b][3]benzazepine-11-ylidene)piperidine is excluded.

Particularly interesting compounds of formula (VII) are those wherein Q represents ($C_{1-6}$alkyl or phenyl)oxycarbonyl, $C_{1-4}$alkylcarbonyl or $C_{1-6}$alkyl substituted with cyano or amino, the pharmaceutically acceptable acid addition salts thereof and the stereochemically isomeric forms thereof.

In the following paragraphs there are described several methods of preparing the starting materials employed in the foregoing preparations.

The intermediates of formula (II) can be prepared from the corresponding ketones of formula (III) by reduction.

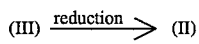

Said reduction can conveniently be conducted by reacting the starting ketone (III) with hydrogen in a solvent such as, for example, an alcohol, e.g. methanol, ethanol; an acid, e.g. acetic acid; an ester, e.g. ethyl acetate; in the presence of a hydrogenation catalyst, e.g. palladium-on-charcoal, platinum-on-charcoal, Raney Nickel.

In order to enhance the rate of the reaction, the reaction mixture may be heated and, if desired, the pressure of the hydrogen gas may be raised.

Alternatively, the alcohols of formula (II) can also be prepared by reducing the ketones (HI) with a reducing agent such as, for example, lithium aluminum hydride, sodium borohydride, sodium cyanoborohydride and the like in a suitable solvent such as, for example, an ether, e.g. 1,1'-oxybisethane, tetrahydrofuran and the like; an alcohol, e.g. methanol, ethanol and the like.

The ketones of formula (III) can be prepared by the addition of a compound of formula (XX) to a reagent of formula (XXI) under the reaction conditions described hereinbefore for the preparation of the compounds of formula (I-g) from the compounds of formula (I-c).

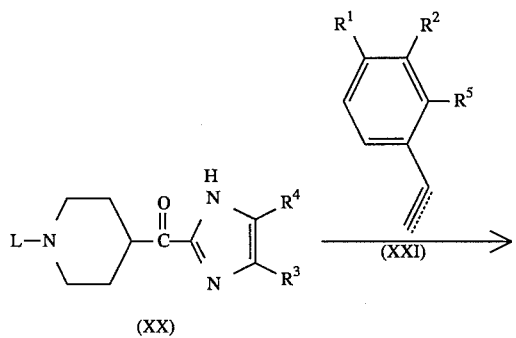

The ketones of formula (III) wherein the dotted line is not an optional bond can be prepared by N-alkylating an intermediate of formula (XX) with a reagent of formula (XXII) wherein W represents a reactive leaving group as defined hereinbefore.

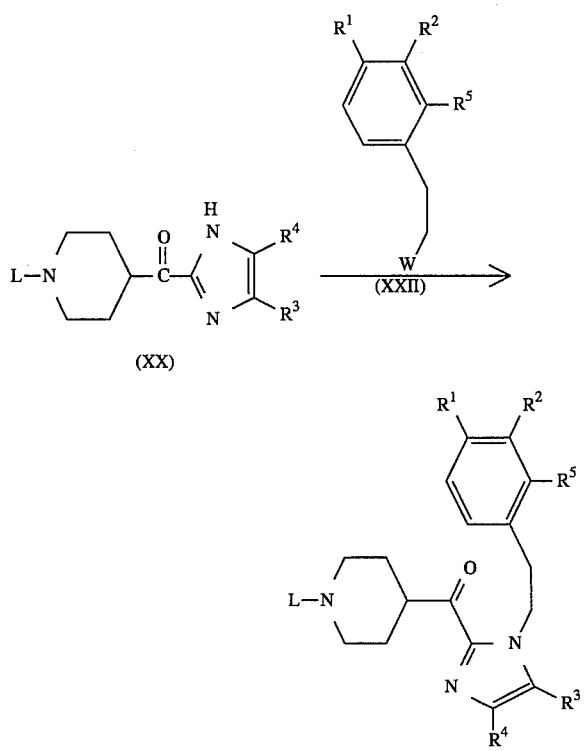

Said N-alkylation reaction can conveniently be conducted following the procedures employed in preparing the compounds of formula (I-e) from the compounds of formula (I-c).

Further, the ketones of formula (III) wherein the dotted line is not an optional bond may also be prepared by reductive N-alkylation of the compounds of formula (XX) under the reaction conditions described for the preparation of the compounds of formula (I-f) from the compounds of formula (I-c).

The intermediates of formula (XX) are conveniently prepared from an ester of formula (XXIII) by reaction with a protected imidazole derivative of formula (XXIV) by reaction with a strong base such as, for example, methyl lithium, butyl lithium, sodium amide, a dialkyl lithium amide, e.g. diisopropyl lithium amide, or a mixture thereof, in a reaction-inert solvent, e.g. tetrahydrofuran, hexane, methylbenzene and the like, or a mixture thereof.

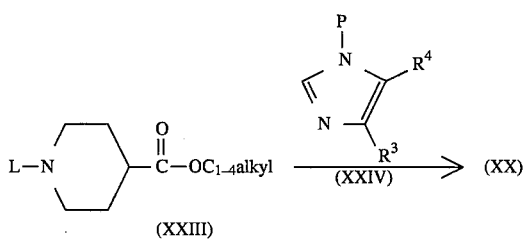

In (XXIV) P represents a protective group such as, for example, di($C_{1-4}$alkoxy)methyl, $C_{1-4}$alkoxymethyl, benzenesulfonyl, trimethylsilylethoxymethyl, N,N-dialkylaminomethyl which can be removed by acid hydrolysis. The reaction of (XXIII) and (XXIV) is conveniently conducted at low temperatures. For example, the reagent (XXIV) may be added at a temperature between about −80° C. to about −40° C. to the strong base. Subsequently, the ester (XXIII) is added and the reaction mixture is allowed to warm up gently to room temperature. The thus obtained product is converted into intermediate (XX) by very mild acid hydrolysis and isolated in a conventional manner.

The ketones of formula (III) wherein L represents methyl, can be prepared from the ketones wherein L represents hydrogen by reductive N-alkylation with formaldehyde following the methods described hereinbefore for the preparation of the compounds of formula (I-f) from the compounds of formula (I-c).

The ketones of formula (III) wherein L represents hydrogen are prepared by hydrolysis of a carbamate of formula (III-a) in acidic or basic media following conventional methods as described hereinbefore for the preparation of compounds of formula (I-c) from the compounds of formula (I-b).

The intermediates of formula (III-a) can be prepared by reacting an acid halide of formula (XXV) with an imidazole derivative of formula (XXVI).

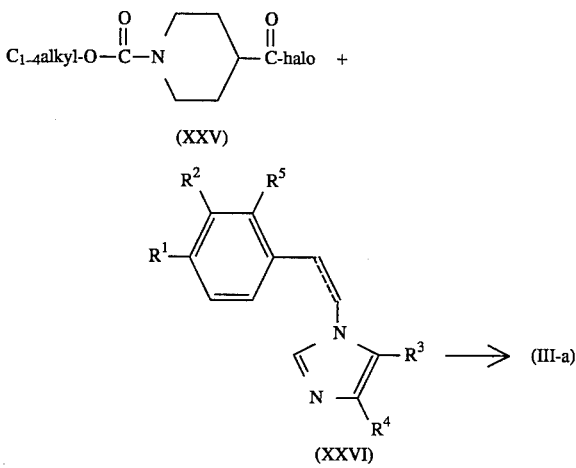

Said reaction is conveniently conducted by stirring and heating the reactants in the presence of a base such as, for example, an amine, e.g. N,N-diethylethanamine, N-methylmorpholine and the like, in a suitable solvent such as, for example, pyridine, acetonitrile or a mixture thereof.

The intermediates of formula (III-c) can also be prepared from an ester of formula (XXVII) by reaction with an imidazole of formula (XXVI) in the presence of a strong base such as, for example, methyl lithium, butyl lithium, sodium amide, a dialkyl lithium amide, e.g. diisopropyl lithium amide, or a mixture thereof, in a suitable reaction-inert solvent, e.g. tetrahydrofuran, hexane, methylbenzene and the like, or a mixture thereof.

Said reaction is conveniently conducted at low temperatures. For example the reagent (XVI) may be added at a temperature between about −80° C. to about −40° C. to the strong base. Subsequently the ester is added and the reaction mixture is allowed to warm up gently to room temperature.

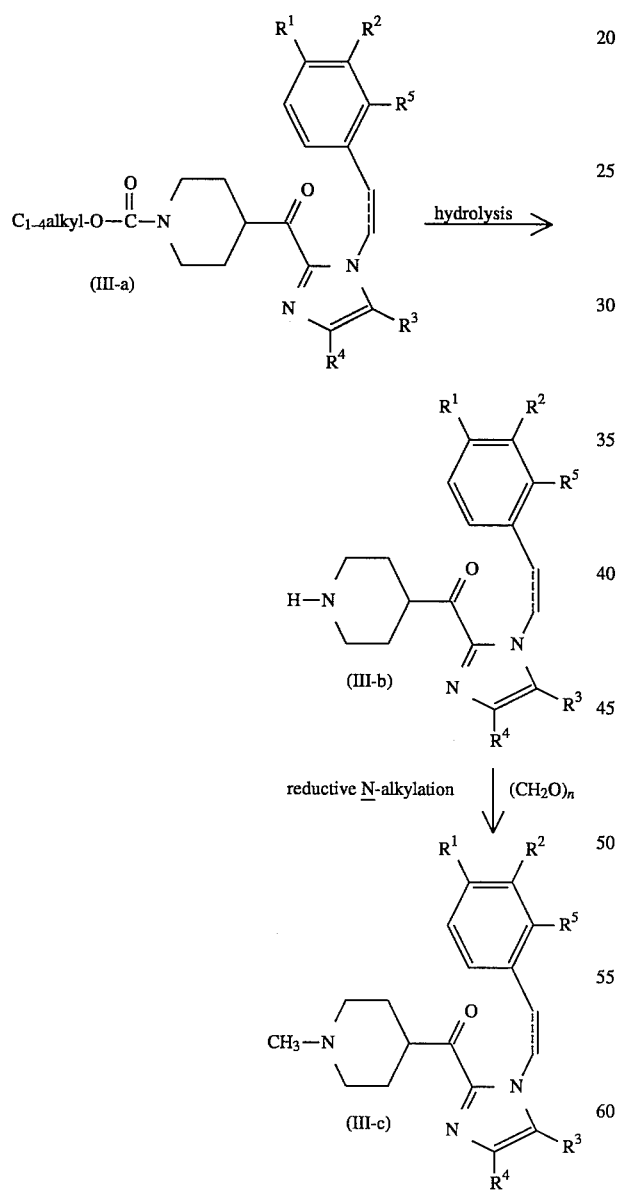

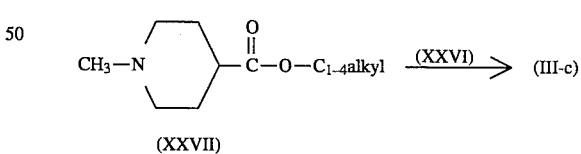

The intermediates of formula (V) can be prepared by addition of a Grignard reagent (XXVIII) to a ketone of formula (XXIX) in a reaction-inert solvent, e.g. tetrahydrofuran.

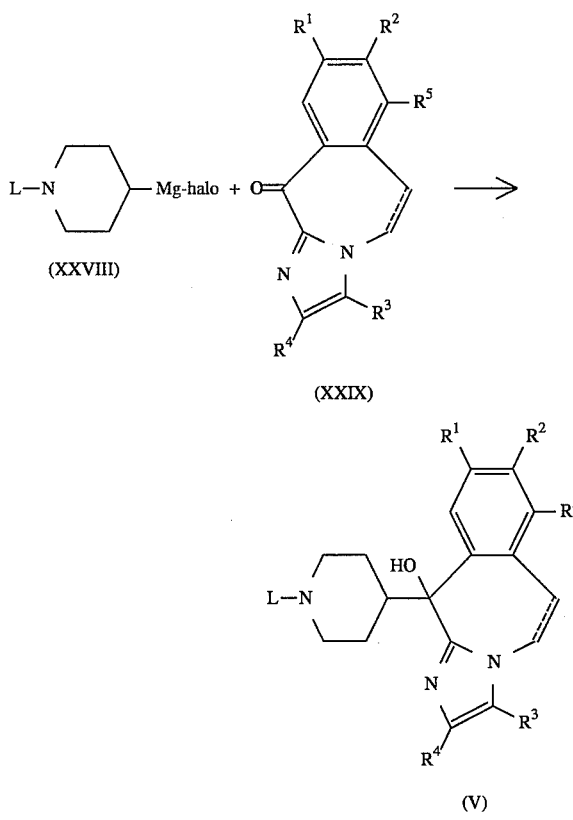

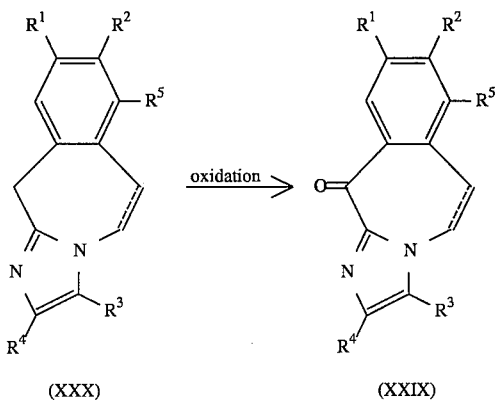

The tricyclic ketones of formula (XXIX) in turn are prepared from intermediates of formula (XXX) by oxidation with suitable oxidizing reagent in a reaction-inert solvent.

Suitable oxidizing reagents are, for example, manganese dioxide, selenium dioxide, ceric ammonium nitrate and the like. Reaction-inert solvents are, for example, halogenated hydrocarbons, e.g. dichloromethane, trichloromethane and the like.

The compounds of formula (XXX) wherein the dotted lines do not represent an optional bond, can be prepared from the corresponding compounds of formula (XXX) wherein said dotted lines do represent an optional bond, following art-known hydrogenation procedures, e.g. by reaction with hydrogen in the presence of a hydrogenation catalyst.

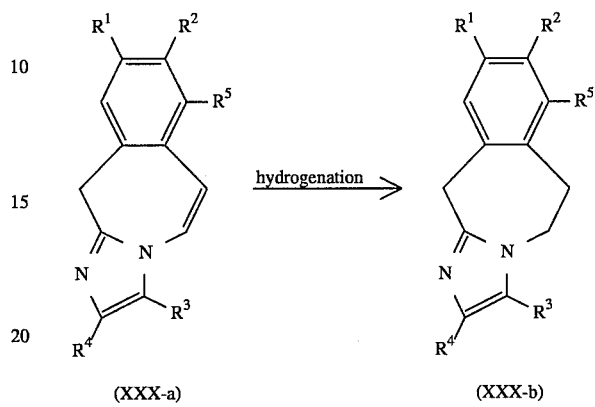

The intermediates of formula (XXX-a) can be prepared from a benzazepine of formula (XXXI) by reaction with a reagent of formula (XXXII) and cyclization of the thus obtained intermediate (XXXIII) in an acidic medium. In (XXXII) R represents $C_{1-4}$alkyl or both radicals R taken together represent $C_{2-6}$alkanediyl, e.g. 1,2-ethanediyl, 1,3-propanediyl, 2,2-dimethyl-1,3-propanediyl.

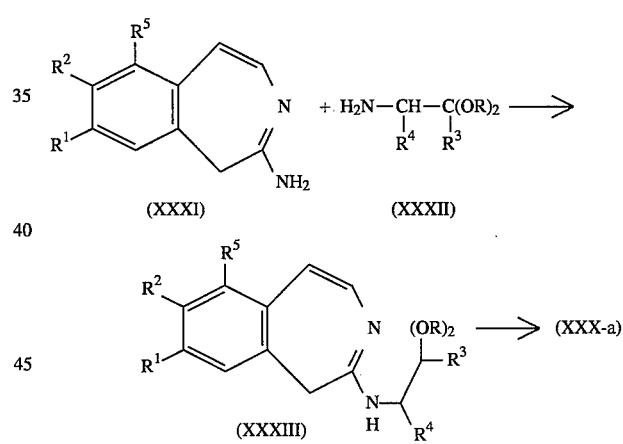

The preparation of (XXXIII) is conveniently conducted by stirring and heating the reactants in a reaction-inert solvent such as, for example, an alcohol, e.g. methanol, ethanol and the like.

The cyclization reaction to the intermediates of formula (XXX-a) is conducted by stirring and heating the starting material (XXXIII) in a carboxylic acid such as, for example, acetic acid, propanoic acid, optionally in admixture with a mineral acid such as, for example, hydrochloric acid.

The intermediates of formula (XXX) can also be prepared from cyclization of an intermediate of formula (XXXIV).

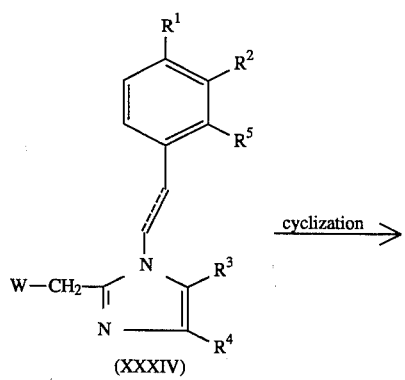

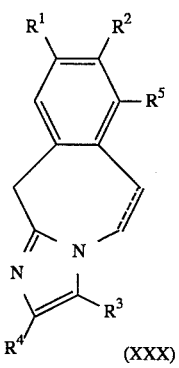

Said cyclization reaction is conveniently conducted in the presence of a Lewis acid, e.g. aluminium chloride, and the like. In some instances it may be appropriate to supplement the reaction mixture with a suitable amount of sodium chloride.

The intermediates of formula (V) can also be prepared from the cyclization of an intermediate of formula (III) in the presence of an acid in a reaction inert solvent.

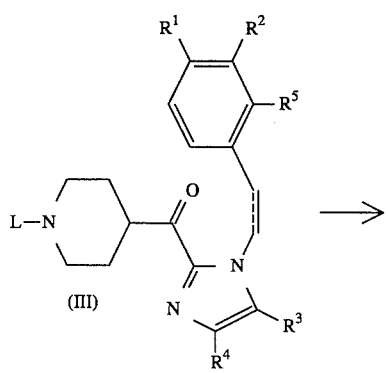

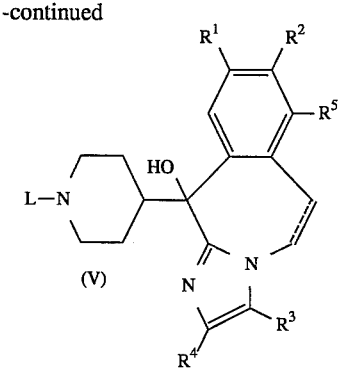

An appropriate acid in the above reaction is, for example, a Lewis acid, e.g. tin(IV)chloride and the like. A suitable reaction-inert solvent is, for example, a halogenated hydrocarbon, e.g. dichloromethane, 1,2-dichloroethane, and the like.

The intermediates of formula (VI) can be prepared by reaction of a ketone of formula (XXXV) with an intermediate of formula (XXX) in the precence of e.g. lithium diisopropylamide in a reaction-inert solvent, e.g. tetrahydrofuran.

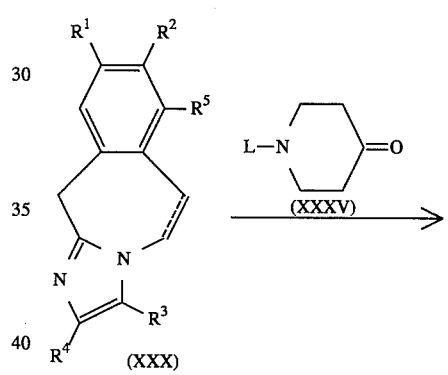

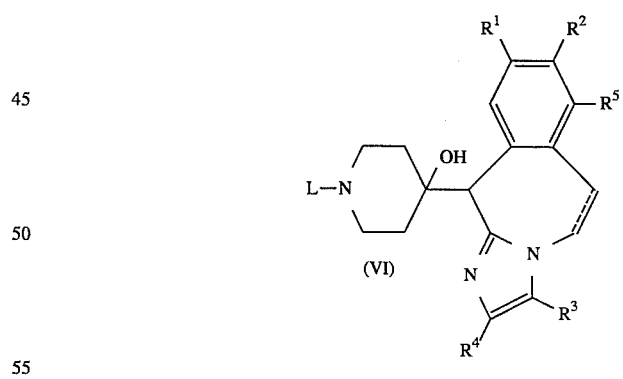

The intermediates of formula (VII-c) can be prepared by N-alkylating a compound of formula (I-c) with a reagent of formula (XXXVI) following the procedures described hereinbefore for the preparation of the compounds of formula (I-e).

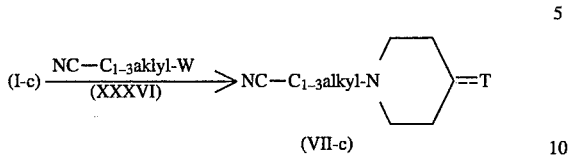

The intermediates of formula (VII-d) can be prepared from the compounds of formula (I-k) wherein Y is oxygen by reaction with a halogenating reagent such as, for example, thionyl chloride, phosphorous trichloride, phosphoryl chloride and the like, or by reaction with a sulfonating reagent such as, for example, methanesulfonyl chloride, 4-methylbenzenesulfonyl chloride and the like.

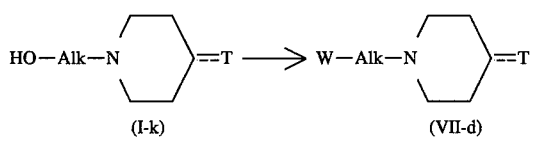

The intermediates of formula (XV) can be prepared by the following reaction sequence.

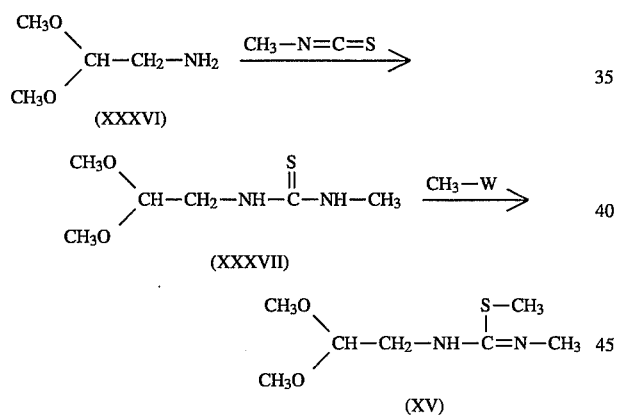

The reaction of (XXXVI) with the isothiocyanate reagent can conveniently be conducted in a reaction-inert solvent such as, for example, an ether, e.g. tetrahydrofuran and the like. The resulting intermediate of formula (XXXVII) is methylated in a reaction-inert solvent such as, for example, a ketone, e.g. 2-propanone and the like.

The compounds of formula (XXX) intervening in the preparations described hereinbefore are novel, except for 2-methylimidazo[2,1-b][3]benzazepine, 2-phenylimidazo[2,1-b][3]benzazepine and 8,9-dimethoxyimidazo[2,1-b][3]benzazepine and have especially been developed for use as intermediates in said preparations. Consequently, the present invention also relates to novel compounds of formula

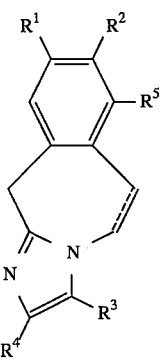

(XXX)

the addition salt forms thereof and the stereochemically isomeric forms thereof, wherein $R^1$, $R^2$, $R^3$, $R^4$, and $R^5$ are as defined under formula (I), 2-methylimidazo[ 2,1-b][3]benzazepine, 2-phenylimidazo[2,1-b][3]benzazepine and 8,9-dimethoxyimidazo[2,1-b][3]benzazepine being excluded.

The compounds of formula (I) and some of the compounds of formula (VII), in particular those wherein Q is ($C_{1-6}$alkyl or phenyl)oxycarbonyl, $C_{1-4}$alkylcarbonyl or $C_{1-6}$alkyl substituted with cyano or amino, the pharmaceutically acceptable acid addition salts and stereochemically isomeric forms thereof possess useful pharmacological properties. In particular they are active antiallergic agents, which activity can clearly be demonstrated by he test results obtained in a number of indicative tests.

Antihistaminic activity can be demonstrated in

'Protection of Rats from Compound 48/80—induced Lethality' test (Arch. Int. Pharmacodyn. Ther., 234, 164–176, 1978);

'Histamine—induced Lethality in Guinea Pigs' test (Arch. Int. Pharmacodyn. Ther., 251, 39–51,1981);

and the broad antiallergic activity can be demonstrated in

'Passive cutaneous anaphylaxis in Rats' test (Drug Dev. Res., 5, 137–145, 1985) (For some compounds this test has been modified by replacing compound 48/80 by Ascaris allergens) and the 'Ascaris Allergy in Dogs' test (Arch. Int. Pharmacodyn. Ther., 251, 39–51, 1981 and Drug Dev. Res., 8, 95–102, 1986).

The compounds of the present invention show a broad spectrum antiallergic profile as is evidenced by the results obtained in the diversity of test procedures cited hereinbefore.

A second advantageous feature of the compounds of the present invention resides in their excellent oral activity; the present compounds when administered orally have been found to be practically equipotent with the same being administered subcutaneously.

A particularly important asset of most of the present compounds is their lack of sedating properties at therapeutic dose levels, a troublesome side effect associated with many antihistaminic and antiallergic compounds. The non-sedating properties of the present compounds can be demonstrated, for example, by the results obtained in studying the sleep-wakefulness cycle of the rat (Psychopharmacology, 97, 436–442, (1989)).

Another interesting feature of the present compounds relates to their fast onset of action and the favorable duration of their action.

In view of their antiallergic properties, the compounds of formula (I) and (VII), wherein Q is ($C_{1-6}$alkyl or phenyl)oxycarbonyl, $C_{1-4}$alkylcarbonyl or $C_{1-6}$alkyl substituted with cyano or amino, and their acid addition salts are very useful in the treatment of broad range of allergic diseases such as, for example, allergic rhinitis, allergic conjunctivitis, chronic urticaria, allergic asthma and the like.

In view of their useful antiallergic properties the subject compounds may be formulated into various pharmaceutical forms for administration purposes. To prepare the antiallergic compositions of this invention, an effective amount of the particular compound, in base or acid addition salt form, as the active ingredient is combined in intimate admixture with a pharmaceutically acceptable carder, which carder may take a wide variety of forms depending on the form of preparation desired for administration. These pharmaceutical compositions are desirably in unitary dosage form suitable, preferably, for administration orally, rectally, percutaneously, or by parenteral injection. For example, in preparing the compositions in oral dosage form, any of the usual pharmaceutical media may be employed such as, for example, water, glycols, oils, alcohols and the like in the case of oral liquid preparations such as suspensions, syrups, elixirs and solutions: or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on or as an ointment. Acid addition salts of the subject compounds due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carder. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention also relates to a method of treating warm-blooded animals suffering from said allergic diseases by administering to said warm-blooded animals an effective antiallergic amount of a compound of formula (I) and (VII), wherein Q is ($C_{1-6}$alkyl or phenyl)oxycarbonyl, $C_{1-4}$alkylcarbonyl or $C_{1-6}$alkyl substituted with cyano or amino or a pharmaceutically acceptable acid addition salt form thereof.

In general it is contemplated that an effective antiallergic amount would be from about 0.001 mg/kg to about 20 mg/kg body weight, and more preferably from about 0.01 mg/kg to about 5 mg/kg body weight.

The following examples are intended to illustrate and not to limit the scope of the present invention in all its aspects.

EXPERIMENTAL PART

A. Preparation of the intermediates

Example 1 a) To a cooled mixture of 54.2 g of 1-(2-phenylethyl)-1 H-imidazole, 34.7 g of N,N-diethylethanamine and 50 ml of pyridine there were added dropwise 69.2 g of ethyl 4-chlorocarbonyl-1-piperidinecarboxylate- (temp.≦0.20° C.) and then 30 ml of acetonitrile. The whole was stirred for 2 hours at room temperature and for 4 hours at reflux temperature. After cooling, there were added 30 ml NaOH 50% and refluxing was continued for ½ hour. The cooled reaction mixture was evaporated and the residue was taken up in water. The product was extracted with dichloromethane and the extract was dried, filtered and evaporated. The residue was purified by column chromatography (silica gel; $CH_2Cl_2/CH_3OH$ 97:3). The eluent of the desired fraction was evaporated and the residue was dried, yielding 38 g (33.9%) of ethyl 4-[[1-(2-phenylethyl)-1H -imidazol-2-yl]carbonyl]-1-piperidinecarboxylate (interm. 1).

In a similar manner there was also prepared:
ethyl 4-[[1-[2-(2-chlorophenyl)ethyl]-1 H-imidazol-2-yl] carbonyl]-1-piperidinecarboxylate (interm. 37).

b) A mixture of 9 g of intermediate (1) and 50 ml of hydrobromic acid 48% was stirred for 5 hours at 80° C. The reaction mixture was evaporated and the residue was boiled in 2-propanol. After cooling, the precipitate was filtered off and dried, yielding 10.85 g (97.5%) of [1-(2-phenylethyl)-1 H-imidazol-2-yl](4-piperidinyl)methanone dihydrobromide; mp. 275.3° C. (interm. 2).

In a similar manner there was also prepared:
[1-[2-(2-methylphenyl)ethyl]-1H-imidazol-2-yl ](4-piperidinyl)methanone dihydrobromide hemihydrate; mp. 231.7° C. (interm. 38).

c) A mixture of 55 g of intermediate (2), 70 ml of formaldehyde and 70 ml of formic acid was stirred for 5 hours at reflux temperature. After cooling, the reaction mixture was diluted with Water and basified with NaOH(aq.). The product was extracted with dichloromethane and the extract was dried, filtered and evaporated. The residue was purified by column chromatography (silica gel; $CH_2Cl_2/CH_3OH$ 90:10). The eluent of the desired fraction was evaporated and the residue was dried, yielding 30 g (82.0%) of (1-methyl-4-piperidinyl) [1-(2-phenylethyl)-1 H-imidazol-2-yl]methanone (interm. 3).

In a similar manner there were also prepared:
[1-[2-(4-fluorophenyl)ethyl]-1 H-imidazol-2-yl](1-methyl-4 -piperidinyl)methanone (interm. 4); and

[1-[2-(2-chlorophenyl)ethyl]-1 H-imidazol-2-yl](1-methyl-4 -piperidinyl)methanone (interm. 39).

Example 2

A mixture of 70.6 g of intermediate (2) and 700 ml of methanol was hydrogenated at normal pressure and at room temperature in the presence of 2 g of platinum-on-charcoal catalyst 5%. After the calculated amount of hydrogen was taken up, the catalyst was filtered off and the filtrate was evaporated. The residue was crystallized from acetonitrile. The product was filtered off and dried, yielding 54 g (75.7 %) of α-[1-(2-phenylethyl)-1H-imidazol-2-yl]-4-piperidinemethanol; mp. 144.6° C. (interm. 5).

Example 3 a) A mixture of 28.9 g of 2-(4-methylphenyl)ethanol methanesulfonate, 18.6 g of 1H-imidazole, 22.7 g of potassium carbonate and 600 ml of tetrahydrofuran was stirred for 18 hours at reflux temperature. After cooling, the reaction mixture was evaporated and the residue was taken up in water and extracted with 4-methyl-2-pentanone. The extract was dried, filtered and evaporated and the residue was distilled (13.3 Pa; 120 ° C.), yielding 20.1 g (83.0%) of 1-[2-(4-methylphenyl)ethyl]-1H-imidazole (interm. 6).

In a similar manner there were also prepared:
1-[2-(3-methylphenyl)ethyl]-1H-imidazole; bp. 120° C. at 13.3 Pa (interm. 7), 1-[2-(4-bromophenyl)ethyl]-1H-imidazole (interm. 8), and 1-[2-(3-chlorophenyl)ethyl]-1H-imidazole; bp. 134° C. at 13.3 Pa (interm. 9).

b) A mixture of 67 g of 1-(2-chloroethyl)-3-methoxybenzene, 53.1 g of 1H-imidazole, 99 g of sodium carbonate, 500 ml of 4-methyl-2-pentanone and a few crystals of potassium iodide was stirred for 48 hours at reflux temperature. After cooling, the reaction mixture was diluted with water and extracted with 4-methyl-2-pentanone. The extract was dried, filtered and evaporated and the residue was distilled (13.3 Pa; 160° C.), yielding 49.5 g (62.8%) of 1-[2-(3-methoxyphenyl)ethyl]-1H-imidazole (interm. 10).

Example 4 a) To a stirred amount of 250 ml of N,N-dimethylformamide under nitrogen, there were added portionwise 6 g of a dispersion of sodium hydride in mineral oil and 82.1 g of 4-methylimidazole and then dropwise 132 g of phenylxirane. The whole was stirred for 50 hours and then diluted with 1000 ml of water. The precipitate was filtered off, washed with water and 2,2'-oxybispropane and recrystallized from a mixture of acetonitrile and ethanol. The product was filtered off and dried, yielding 58.1 parts (28.7%) of 5-methyl-α-phenyl-1H-imidazole-1-ethanol; mp. 192.7° C. (interm. 11).

b) A mixture of 57.1 g of intermediate (11), 130 ml of 2-propanol saturated with HCl and 500 ml of methanol was hydrogenated at normal pressure and at room temperature in the presence of 5 g of palladium-on-charcoal catalyst 10%. After the calculated amount of hydrogen was taken up, the catalyst was filtered off and the filtrate was evaporated. The residue was diluted with water and the whole was basified with NaOH(aq.). The product was extracted with dichloromethane and the extracted was dried, filtered and evaporated. The residue was co-evaporated with methylbenzene (3x), yielding 52.9 g (100%) of 5-methyl-1-(2-phenylethyl)-1H-imidazole (interm. 12).

In a similar manner there was also prepared:
1-[2-(2-methylphenyl)ethyl]-1H-imidazole (interm. 49).

Example 5 a) To a cooled mixture (ice-bath) of 10.1 g of intermediate (10), 12 g of N,N-diethylethanamine and 150 ml of acetonitrile there were added dropwise 21.95 g of ethyl 4-chlorocarbonyl-1-piperidinecarboxylate, keeping the temperature below 20° C. After stirring for 2 hours at room temperature and 4 hours at reflux temperature, there were added dropwise 10 ml NaOH. The whole was refluxed for ½ hour, cooled and evaporated. The residue was taken up in water and the product was extracted with dichloromethane. The extract was dried, filtered and evaporated, yielding 22 g (100%) of ethyl 4-[[1-[2-(3-methoxyphenyl)ethyl]-1H-imidazol-2-yl]-carbonyl] -1-piperidinecarboxylate (interm. 13).

In a similar manner there were also prepared:
ethyl 4-[[1-[2-(3-chlorophenyl)ethyl]-1H-imidazol-2-yl]carbonyl] -piperidinecarboxylate (interm. 14),
1-acetyl-4-[[1-[2-(4-methylphenyl)ethyl]-1H-imidazol-2-yl]carbonyl] piperidine (interm. 15),
ethyl 4-[[5-methyl-1-(2-phenylethyl)-1H-imidazol-2-yl]carbonyl]-1 -piperidinecarboxylate (interm. 16),
ethyl 4-[[1-[2-(3-methylphenyl)ethyl]-1H-imidazol-2-yl]carbonyl]-1 -piperidinecarboxylate (interm. 17),
ethyl 4-[[1-[2-(4-bromophenyl)ethyl]-1H-imidazol-2-yl]carbonyl] -1-piperidinecarboxylate (interm. 18), and
ethyl 4-[[1-[2-(2-methylphenyl)ethyl]-1H-imidazol-2-yl]carbonyl]-1 -piperidinecarboxylate (interm. 40).

b) A mixture of 4.4 g of intermediate (13) and 120 ml of hydrochloric acid 12N was stirred for 72 hours at reflux temperature. The reaction mixture was evaporated and the residue was taken up in water, basified with NaOH and extracted with dichloromethane. The extract was dried, filtered and evaporated. The residue was purified by column chromatography (silica gel; CH₂Cl₂/CH₃OH(NH₃) 90:10). The eluent of the desired fraction was evaporated, yielding 2.63 g (83.9 %) of [1-[2-(3-methoxyphenyl)ethyl]- 1H-imidazol-2-yl](4-piperidinyl)methanone (interm. 19).

In a similar manner there were also prepared:
1-[2-(4-methylphenyl)ethyl]-1H-imidazol-2-yl](4-piperidinyl)methanone dihydrochloride (interm. 20),
[1-[2-(3-chlorophenyl)ethyl]-1H-imidazol-2-yl](4-piperidinyl)methanone (interm. 21), and
[1-[2-(2-methylphenyl)ethyl]-1H-imidazol-2-yl](4-piperidinyl)methanone dihydrobromide; mp. 268.1° C. (interm. 41).

c) A mixture of 130 g of intermediate (16) and 1000 ml of hydrobromic acid 48% was stirred for 24 hours at 80° C. The reaction mixture was evaporated and the residue was recrystallized from 2-propanol. After cooling, the precipitate was filtered off and dried, yielding 124.2 g (95.6%) of [5-methyl-1-(2-phenylethyl)-1H-imidazol-2 -yl](4-piperidinyl dihydrobromide (interm. 22).

In a similar manner there were also prepared:
[1-[2-(3-methylphenyl)ethyl]-1

H-imidazol-2-yl](4-piperidinyl)methanone dihydrobromide (interm. 23), and

[1-[2-(4-bromophenyl)ethyl]-1 H-imidazol-2-yl](4-piperidinyl)methanone dihydrobromide hemihydrate (interm. 24).

Example 6

A mixture of 5.24 g of intermediate (24), 2 g of polyoxymethylene, 3 g of potassium acetate, 2 ml of a solution of thiophene in methanol 4% and 150 ml of methanol was hydrogenated at normal pressure and at room temperature in the presence of 2 g of platinum-on-charcoal catalyst 5%. After the calculated amount of hydrogen was taken up, the catalyst was filtered off and the filtrate was evaporated. The residue was taken up in water and the whole was basified with $K_2CO_3$. The product was extracted with dichloromethane and the extract was dried, filtered and evaporated, yielding 3.2 g (85.0%) of [1-[2-(4-bromophenyl)ethyl]-1 H-imidazol-2-yl](1-methyl-4 -piperidinyl) (interm. 25).

In a similar manner there were also prepared:
[1-[2-(3-chlorophenyl)ethyl]-1 H-imidazol-2-yl](1-methyl-4 -piperidinyl)methanone (interm. 26), and

[1-[2-(3-methoxyphenyl)ethyl]-1 H-imidazol-2-yl](1-methyl-4 -piperidinyl)methanone (interm. 27).

Example 7 a) A mixture of 3.16 g of 1H-3-benzazepin-2-amine, 4.17 g of 2,2-dimethoxyethanamine and 50 ml of methanol was stirred for 16 hours at reflux temperature. The reaction mixture was evaporated and the residue was purified by column chromatography (silica gel; $CH_2Cl_2/CH_3OH$ 95:5). The eluent of the desired fraction was evaporated and the residue was stirred in hexane. The precipitate was filtered off, yielding 4.9 g (100% ) of N-(2,2-dimethoxyethyl)-1 H-3-benzazepin-2-amine (interm. 28).

b) A mixture of 4.9 g of intermediate (28), 70 ml of acetic acid and 9 ml of hydrochloric acid 36% was stirred for 18 hours at 70° C. The reaction mixture was evaporated and the residue was taken up in water. The whole was basified with NaOH(aq.) and extracted with dichloromethane. The extract was dried, filtered and evaporated and the residue was purified by column chromatography (silica gel; $CH_2Cl_2/CH_3OH$ 95:5). The eluent of the desired fraction was evaporated and the residue was treated with active charcoal in 1,1'-oxybisethane. The whole was filtered and the filtrate was evaporated. The residue was triturated in hexane. The product was filtered off and dried, yielding 1.04 g (28.5%) of 11 H-imidazo[2,1-b][3]benzazepine; mp. 85.5° C. (interm. 29).

c) A mixture of 5 g of intermediate (29), 20 g of manganese dioxide and 150 ml of trichloromethane was stirred for 50 hours at reflux temperature. The whole was filtered over diatomaceous earth, 20 g of manganese dioxide were added and refluxing was continued for 48 hours (2x). The reaction mixture was filtered and the filtrate was evaporated. The residue was purified by column chromatography (silica gel; $CH_2Cl_2/CH_3OH$ 95:5). The eluent of the desired fraction was evaporated and the residue was triturated in 1,1'-oxybisethane and then boiled in acetonitrile. After cooling, the product was filtered off and dried, yielding 2.61 g (53.2%) of 11 H-imidazo-[2,1-b][ 3]benzazepin- 11-one; mp. 218.9° C. (interm. 30).

d) A mixture of 10 ml of tetrahydrofuran and 1.24 g of magnesium was stirred under a nitrogen atmosphere. 1 Crystal of iodine and then dropwise 1.2 g of bromoethane were added and at reflux temperature there was added a solution of 6.7 g of 4-chloro-1-methylpiperidine in 25 ml of tetrahydrofuran. After refluxing for 1 hour, the reaction mixture was cooled (0° C.). Then there were added 25 ml of tetrahydrofuran and portionwise 9.8 parts of intermediate (30), keeping the temperature below 10° C. The whole was stirred for 1 hour at room temperature and decomposed with $NH_4Cl$ (aq.). The product was extracted with trichloromethane and the extract was dried, filtered and evaporated. The residue was purified by column chromatography (silica gel; $CH_2Cl_2/CH_3OH$ ($NH_3$) 95:5). The eluent of the second fraction was evaporated and the residue was crystallized from acetonitrile in 2 fractions, yielding 4.76 parts (32.2%) of 11-(1-methyl-4-piperidinyl)-11 H-imidazo[2,1-b][3]benzazepin-11-ol; mp. 155.2° C. (interm. 31).

Example 8

Following the procedure of example 10 (c) and (d) 2-phenyl-11H-imidazo[2,1-b][3] benzazepine-11-one was converted into 11-(1-methyl-4-piperidinyl)-2-phenyl-11 H-imidazo[ 2,1-b][3]benzazepin-11-ol; mp. 239.8° C. (interm. 32).

A mixture of 6 g of intermediate (32) and 300 ml of methanol was hydrogenated at normal pressure and at room temperature in the presence of 3 g of palladium-on-charcoal catalyst 10%. After the calculated amount of hydrogen was taken up, the catalyst was filtered off and the filtrate was evaporated. The residue was purified by column chromatography (silica gel; $CH_2Cl_2/CH_3OH$ 95:5→$CH_2Cl_2/CH_3OH(NH_3)$ 95:5). The eluent of the desired fraction was evaporated and the residue was crystallized from acetonitrile. The product was filtered off and dried, yielding 3.2 g (53.5%) of 6,11-dihydro-11-(1-methyl-4-piperidinyl)-2-phenyl-5H-imidazo[2,1-b] [3]benzazepin- 11-ol; mp. 225.3° C. (interm. 33).

Example 9 a) To a cooled (0° C.) mixture of 46.2 g of 3-fluorobenzenethanol, 40 ml of N,N-diethylethanamine and 500 ml of dichloromethane, there were added dropwise 41.2 g of methanesulfonyl chloride, keeping the temperature below 5° C. After stirring for 18 hours at room temperature, the reaction mixture was diluted with water and extracted with dichloromethane. The extract was dried, filtered and evaporated, yielding 81 g (100%) of 2-(3-fluorophenyl)ethanol methanesulfonate (ester) (interm. 34).

b) A mixture of 72 g of intermediate (34), 45 g of 1 H-imidazole, 55.5 g of potassium carbonate and 1000 ml of tetrahydrofuran was stirred over weekend at reflux temperature. The reaction mixture was filtered over diatomaceous earth and the filtrate was evaporated. The residue was taken up in water and the product was extracted with dichloromethane. The extract was dried, filtered and evaporated. The residue was purified by column chromatography (silica gel; $CH_2Cl_2/CH_3OH$ 95:5). The eluent of the desired fraction was evaporated and the residue was distilled (53.2 Pa; 130° C.), yielding 37.8 parts (60.2%) of 1-[2-(3-fluorophenyl)ethyl]-1H-imidazole (interm. 35).

c) To a cooled (−70° C.) mixture of 5.5 g of 2-methyl-N-(1-methylethyl)ethanamine and 100 ml of tetrahydrofuran under a nitrogen atmosphere there were added dropwise 22 ml of butyllithium and after stirring for 15 min. at −40° C., 9.5 g of intermediate (35) at −70° C. Stirring at −70° C. was continued for 1 hour and then there were added 9.4 g of ethyl 1-methyl-4-piperidinecarboxylate. The whole was stirred for 18 hours at room temperature, decomposed with water and evaporated. The residue was taken up in water and the product was extracted with dichloromethane. The extract was dried, filtered and evaporated. The residue was purified by column chromatography (silica gel; $CH_2Cl_2/CH_3OH$ 95:5→ $CH_2Cl_2/CH_3OH$ 80:20). The eluent of the desired fraction was evaporated, yielding 8 g (50.7%) of [1-[2-(3-fluorophenyl)ethyl]-1H-imidazol-2-yl] (1-methyl-4-piperidinyl)methanone (interm. 36).

Example 10 a) To a stirred and cooled (−70° C.) mixture of 18.8 g of N-(1-methylethyl)-2-propanamine in 200 ml of tetrahydrofuran (under nitrogen atmosphere) were added portionwise 42 ml of butyllithium 2.5M in hexane. The mixture was brought to −40° C. and stirred at this temperature for 15 minutes. The mixture was cooled again to −70° C. and a solution of 17 g of 1-(diethoxymethyl)-1H-imidazole in tetrahydrofuran was added dropwise at this temperature. Stirring was continued for 1 hour and a solution of 18.8 g of ethyl 1-methyl-4-piperidinecarboxylate in 200 ml of tetrahydrofuran was added. After stirring for 1 hour at −70° C. and for another hour at room temperature, the mixture was decomposed with water, acidified with HCl and evaporated. The residue was taken up in water, alkalized with potassium carbonate and extracted with a mixture of dichloromethane and methanol. The extract was dried, filtered and evaporated. The residue was purified on silica (eluent: $CH_2Cl_2/(CH_3OH/NH_3)$95/5). The pure fractions were collected and the eluent was evaporated. The residue was crystallized from acetonitrile. The product was filtered off and dried, yielding: 2.75 g of (1H-imidazol-2-yl)(1-methyl-4-piperidinyl)methanone (12.9%); mp. 143.6° C. (interm. 42).

b) To 200 ml of N,N-dimethylformamide were added portionwise 13.2 g of a sodium hydride dispersion 50% in mineral oil and then 48.3 g of intermediate (42) under nitrogen atmosphere while stirring. After stirring for 1.5 hours at room temperature, a solution of 65 g of 2-fluorobenzeneethanol methanesulfonate (ester) in N,N-dimethylormamide was added dropwise to the reaction mixture. The reaction mixture was stirred for 18 hours at 60° C., cooled and decomposed with water. The product was extracted with dichloromethane. The extract was dried, filtered and evaporated. The residue was taken up in water, acidified with hydrochloric acid, washed twice with 2,2'-oxybispropane, treated with potassium carbonate and extracted again with dichloromethane. The extract was dried, filtered and evaporated. The residue was converted into the (E)-2-butenedioate salt in ethanol. The salt was filtered off and dried, yielding 61.9 g (50.6%) of [1-[2-(2-fluorophenyl)ethyl]-1 H-imidazol-2-yl](1-methyl- 4-piperidinyl)methanone (E)-2-butenedioate (2:3); mp. 131.7° C. (interm. 43).

Example 11

22.3 g of methyl 4'-methyl-(1,1'biphenyl)-2-carboxylate were dissolved in 900 ml of tetrachloromethane under a nitrogen flow. Then there were added 17.8 g of 1-bromo-2,5-pyrrolidinedione and a catalytic amount of dibenzoyl peroxide. After stirring for 2.5 hours at reflux temperature under a nitrogen atmosphere, the reaction mixture was cooled and filtered. The filtrate was evaporated, yielding >30 g (100% ) of methyl 4'-(bromomethyl)[ 1,1'-biphenyl]-2-carboxylate as a crude residue (interm. 44).

Example 12 a) To a freshly prepared sodium methoxide solution, prepared in the usual manner starting from 23 g of sodium and 350 ml of methanol was added a solution of 68 g of 1H-imidazole in 100 ml of methanol. The solvent was evaporated and the residue was taken up in 320 ml of N,N-dimethylformamide. The solvent was removed again till the temperature rose to 125° C. After cooling to 30° C., 185 g of (2-bromoethyl)benzene were added to the residue and the whole was stirred overnight. The reaction mixture was diluted with 1500 ml of water and 230 ml of benzene. The separated aqueous layer was extracted twice with benzene. The combined organic layers were treated with 750 ml of a hydrochloric acid solution 4N and than basified. The product was extracted with benzene. The extract was dried, filtered and evaporated. The oily residue was distilled in vacuo, yielding 55 g of 1-(2-phenylethyl)-1 H-imidazole; bp. 140°–145° C. at 23.3 Pa (interm. 45).

b) A mixture of 34.5 g of intermediate (45) and 200 ml of formaldehyde 37% in water was stirred and refluxed for 48 hours. After evaporation, the residue was taken up in water and treated with a diluted ammonium hydroxide solution while cooling. The whole was stirred for 30 minutes and extracted with methylbenzene. The extract was dried, filtered and evaporated. The residue was purified by column chromatography (eluent: $CH_2Cl_2/CH_3OH$ 95:5). The eluent of the desired fraction was evaporated and the residue was stirred in 2,2'-oxybispropane. The precipitated product was filtered off and dried in vacuo, yielding 29.9 g (73.8%) of 1-(2-phenylethyl)-1 H-imidazole-2-methanol; mp. 75.4° C. (interm. 46).

c) To 50 ml of thionyl chloride were added portionwise 4 g of intermediate (46). The reaction mixture was stirred and refluxed for 30 minutes. The reaction mixture was evaporated and the residue was stirred in 2,2'-oxybispropane. The precipitated product was filtered off and dried, yielding 4.61 g (89.6%) of 2-(chloromethyl)-1-(2 -phenylethyl)-1H-imidazole monohydrochloride; mp. 240.2° C. (interm. 47).

d) A mixture of 19.6 g of intermediate 47, 59 g of aluminium chloride and 25.5 g of sodium chloride was stirred for 30 minutes at 100° C. After cooling, the reaction mixture was poured into ice water and treated with sodium hydroxide. The product was extracted with methylbenzene. The extract was dried, filtered and evaporated, yielding 13.1 g (93.5%) of 6,11-dihydro-5 H-imidazo[2,1-b][3]benzazepine (interm. 48).

B. Preparation of the final compounds

Example 13

A mixture of 2.5 g of intermediate (26) and 10 ml of trifluoromethanesulfonic acid was stirred for 72 hours at 110° C. under nitrogen. After cooling, the reaction mixture was poured into ice-water and the whole was basified with NaOH (aq.). The product was extracted with dichloromethane and the extract was dried, filtered and evaporated. The residue was purified by column chromatography (silica gel; CH$_2$Cl$_2$/CH$_3$OH (NH$_3$) 95:5). The eluent of the desired fraction was evaporated and the residue was crystallized from acetonitrile. The product was filtered off and dried, yielding 0.95 g (40.4%) of 8-chloro-6,11-dihydro-11-(1-methyl-4-piperidinylidene)-5H-imidazo[2,1-b][3 ]-benzazepine; mp. 186.6° C. (comp. 3.10).

Example 14

A mixture of 2 g of intermediate (27) and 10 ml of methanesulfonic acid was stirred for 1 hour at 100° C. The reaction mixture was poured into ice-water and the whole was basified with NaOH (aq.). The product was extracted with dichloromethane and the extract was dried, filtered and evaporated. The residue was purified by column chromatography (silica gel; CH$_2$Cl$_2$/CH$_3$OH(NH$_3$) 95:5). The eluent of the desired fraction was evaporated and the residue was converted into the (Z)-2-butenedioate (1:2) salt in 2-propanone. The salt was filtered off and dried, yielding 1 g (30.8%) of 6,11-dihydro- 8-methoxy-11-(1-methyl-4-piperidinylidene)-5H-imidazo[2,1-b][3]-benzazepine (Z)-2-butenedioate(1:2); mp. 190.3° C. (comp. 3.01).

Example 15

A mixture of 8 g of intermediate (36), 24 g of aluminum chloride and 10.3 g of sodium chloride was stirred at 140° C. until the whole was melted. Stirring was continued for 1 hour at 120° C. The reaction mixture was poured into ice-water and the whole was basified with NaOH (aq.). The product was extracted with dichloromethane and the extract was dried, filtered and evaporated. The residue was purified by column chromatography (silica gel; CH$_2$Cl$_2$/CH$_3$OH 95:5→CH$_2$Cl$_2$/CH$_3$OH(NH$_3$) 90:10). The eluent of the desired fraction was evaporated and the residue was triturated in 2,2'-oxybispropane and recrystallized from 4-methyl-2-pentanone. The product was filtered off and dried, yielding 0.58 g (10.8%) of 8-fluoro-6,11-dihydro-11-(1-methyl- 4-piperidinylidene)-5H-imidazo[2,1-b][3]benzazepine; mp. 152.4° C. (comp. 3.15).

Example 16

A mixture of 3.5 g of intermediate (5) and 10 ml of trifluoromethanesulfonic acid was stirred for 18 hours at 110° C. The reaction mixture was poured into ice-water and the whole was basified with NaOH (aq.). The product was extracted with dichloromethane and the extract was washed with water, dried, filtered and evaporated. The residue was converted into the (E)-2-butenedioate (1:2) salt in ethanol. The salt was recrystallized from ethanol, yielding 0.8 g (13.3%) of 6,11-dihydro-11-(4-piperidinyl)-5H-imidazo-[2,1-b][3]benzazepine (E)-2-butenedioate (1:2); mp. 220.2° C. (comp. 5.01).

Example 17

A mixture of 2.2 g of intermediate (33), 10 ml of sulfuric acid and 10 ml of methanesulfonic acid was stirred for 2 hours at 70° C. The reaction mixture was poured into ice-water and the whole was basified with NaOH (aq.). The product was extracted with dichloromethane and the extract was dried, filtered and evaporated. The residue-was purified by column chromatography (silica gel; CH$_2$Cl$_2$/CH$_3$OH 95:5→CH$_2$Cl$_2$/CH$_3$OH(NH$_3$) 90:10). The eluent of the desired fraction was evaporated and the residue was crystallized from acetonitrile. The product was filtered off and dried, yielding 0.73 g (34.2%) of 6,11-dihydro-11-(1-methyl-4-piperidinylidene)-2-phenyl-5H-imidazo-[ 2,1-b][3]benzazepine; mp. 171.5° C. (comp. 4.01).

Example 18

A mixture of 14.7 g of intermediate (31) and 150 ml of acetic anhydride was stirred for 2 hours at reflux temperature. The reaction mixture was evaporated and the residue was taken up in water. The whole was basified with NaOH (aq.) and then extracted with dichloromethane. The extract was dried, filtered and evaporated and the residue was purified by column chromatography (silica gel; CH$_2$Cl$_2$/CH$_3$OH 95:5→CH$_2$Cl$_2$/CH$_3$OH(NH$_3$) 95:5). The eluent of the first fraction was evaporated and the residue was taken up in 1,1'-oxybisethane. The whole was filtered and the filtrate was treated with activated charcoal. After filtration, the solution was evaporated and the residue was triturated in 2,2'-oxybispropane. The product was filtered off and dried, yielding 1.6 g (11.5%) of product. The second fraction was also evaporated and the residue taken up in 1,1'-oxybisethane. The whole was filtered and the filtrate was combined with the 2,2'-oxybispropane-filtrate of the first fraction, and evaporated, yielding an additional 8.2 g (59.1%) of product. Total yield: 9.8 g (70.6%) of 11-(1-methyl-4 -piperidinylidene)-11 H-imidazo[2,1-b][3]benzazepine; mp. 135.8° C. (comp. 6.01).

Example 19

To a stirred and refluxing mixture of 7.2 g of compound (3.10), 4.6 g of N,N-diethylethanamine and 200 ml of methylbenzene there were added dropwise 12.5 g of ethyl chloroformate. After refluxing for 1 hour and subsequent cooling, the reaction mixture was diluted with water. The whole was basified with K$_2$CO$_3$ and then extracted with methylbenzene. The extract was dried, filtered and evaporated and the residue was purified by column chromatography (silica gel; CH$_2$Cl$_2$/CH$_3$OH 95:5). The eluent of the desired fraction was evaporated and the residue was stirred in 1,1'-oxybisethane. The product was filtered off and dried, yielding 6.62 g (77.4%) of ethyl 4-(8-chloro- 5,6-dihydro-11 H-imidazo[2,1-b][3]benzazepin-11-ylidene)-1-piperidinecarboxylate; mp. 140.3° C. (comp. 3.11).

Example 20 a) A mixture of 2.5 g of compound (1.03) and 50 ml of formaldehyde 40% was stirred for 1 week at reflux temperature. The reaction mixture was evaporated and the residue was taken up in water. The whole was basified with NH$_4$OH, stirred for ½ hour and extracted with dichloromethane. The extract was dried, filtered and evaporated and the residue was purified by column chromatography (silica gel; CH$_2$Cl$_2$/CH$_3$OH 95:5). The eluent of the desired fraction was evaporated and the residue was crystallized from acetonitrile. The product was filtered off and dried, yielding 0.45 g (16.3%) of ethyl 4-[5,6-dihydro-3-(hydroxymethyl)-11H-imidazo[2,1-b][ 3]benzazepin-11-ylidene]-1-piperidinecarboxylate; mp. 191.9° C. (comp. 4.11).

b) A mixture of 20 g of compound (1.03) and 400 ml of formaldehyde 40% was stirred for 2 weeks at reflux temperature. The reaction mixture was evaporated and the residue was taken up in water. After basifying with NH$_4$OH, the product was extracted with dichloromethane. The extract was dried, filtered and evaporated and the residue was purified by column chromatography (silica gel; CH$_2$Cl$_2$/CH$_3$OH 95:5→CH$_2$Cl$_2$/CH$_3$OH(NH$_3$) 95:5). The eluent of the third fraction was evaporated, yielding 4.1 g (17.2%) of ethyl 4-[5,6-dihydro-2,3-bis(hydroxymethyl)-l 1H-imidazo-[2,1-b][3 -benzazepin-11-ylidene]-1-piperidinecarboxylate (comp. 4.18).

Example 21

A mixture of 13 g of compound (1.03), 13 g of potassium hydroxide and 100 ml of 2-propanol was stirred for 6 hours at reflux temperature. The reaction mixture was evaporated and the residue was taken up in water. The product was extracted with dichloromethane and the extract was dried, filtered and evaporated. The residue was purified by column chromatography (silica gel; CH$_2$Cl$_2$/CH$_3$OH(NH$_3$) 90:10). The eluent of the desired fraction was evaporated and the residue was converted into the (E)-2-butenedioate (1:2) salt in ethanol. The salt was filtered off and dried, yielding 3.52 g (18.3%) of 6,11-dihydro-11-(4-piperidinylidene)-5H-imidazo[2,1-b][3]benzazepine (E)-2-butenedioate (1:2) hemihydrate; mp. 192.5° C. (comp. 1.04).

Example 22

A mixture of 60 g of compound (6.02) and 500 ml of hydrobromic acid 48% was stirred for 5 hours at reflux temperature. The reaction mixture was evaporated and the residue was taken up in water. After basifying with NaOH (aq.), the product was extracted with dichloromethane. The extract was dried, filtered and evaporated and the residue was purified by column chromatography (silica gel; CH$_2$Cl$_2$/CH$_3$OH(NH$_3$)95:5→CH$_2$Cl$_2$/CH$_3$OH(NH$_3$) 90:10). The eluent of the first fraction was evaporated and the residue was converted into the dihydrobromide salt in ethanol. The salt was filtered off and dried, yielding 27.3 g (37.7%) of 11-(4-piperidinylidene)-11H-imidazo[2,1-b][3]benzazepine dihydrobromide hemihydrate; mp. 246.9° C. (comp. 6.03).

Example 23

A mixture of 6.1 g of compound (3.11) and 100 ml of hydrochloric acid 12N was stirred for 18 hours at reflux temperature. The reaction mixture was evaporated and the residue was boiled in 2-propanol. After cooling, the precipitate was filtered off and taken up in water. The whole was basified with NaOH (aq.) and then extracted with dichloromethane. The extract was dried, filtered and evaporated and the residue was boiled in acetonitrile. After cooling, the product was filtered off and dried, yielding 2.9 g (59.0%) of 8-chloro-6,11-dihydro-11-(4-piperidinylidene)-5H-imidazo[2,1-b]-[3]benzazepine; mp. 197.1° C. (comp. 3.12).

Example 24

To a stirred and cooled (ice-bath) mixture of 5.6 g of compound (2.12), 50 ml of dichloromethane and 2.5 g of N,N-diethylethanamine there was added dropwise a solution of 2.38 g of ethyl chloroformate in 20 ml of dichloromethane. Stirring was continued for 1 hour at room temperature. The reaction mixture was diluted with water and extracted with dichloromethane. The extract was dried, filtered and evaporated. The residue was purified by column chromatography (silica gel; CH$_2$Cl$_2$/CH$_3$OH 95:5). The eluent of the desired fraction was evaporated and the residue was stirred in 1,1'-oxybisethane. The product was filtered off and dried, yielding 2.85 g (40.5%) of ethyl 4-(5,6-dihydro-9-methyl-11H-imidazo[2,1-b][3]benzazepin-11-ylidene)-1-piperidinecarboxylate; mp. 156.5° C. (comp. 2.13).

Example 25

A mixture of 1.79 g of 3-(2-chloroethyl)-2-oxazolidinone, 2.65 g of compound (1.04), 1.3 g of sodium carbonate, 150 ml of 4-methyl-2-pentanone and 1 g of potassium iodide was stirred for 18 hours at reflux temperature. After cooling, the reaction mixture was diluted with water. The aqueous layer was separated and extracted with dichloromethane. The combined organic layers were dried, filtered and evaporated. The residue was purified by column chromatography (silica gel; CH$_2$Cl$_2$/CH$_3$OH(NH$_3$) 95:5). The eluent of the desired fraction was evaporated and the residue was converted into the (E)-2-butenedioate (2:3) salt in ethanol. The salt was filtered off and dried, yielding 3.4 g (61.5%) of 3-[2-[4-[5,6-dihydro-11H-imidazo[2,1-b][3]benzazepin-11-ylidene]-1-piperidinyl] ethyl]-2-oxazolidinone (E)-2-butenedioate (2:3); mp. 188.8° C. (comp. 1.20).

Example 26

A mixture of 2.3 g of 6-(2-chloroethyl)-7-methylthiazolo[3,2-a]pyrimidin-5-one, 2.65 g of compound (1.04), 1.3 g of sodium carbonate and 100 ml of 4-methyl-2-pentanone was stirred for 24 hours at reflux temperature. After cooling, the reaction mixture was diluted with water. The product was extracted with 4-methyl-2-pentanone and the extract was dried, filtered and evaporated. The residue was purified by column chromatography (silica gel; CH$_2$Cl$_2$/CH$_3$OH(NH$_3$) 95:5). The eluent of the desired fraction was evaporated and the residue was crystallized from 2-propanone. The product was filtered off and dried, yielding 1.89 g (41.3%) of 6-[2-[4-(5,6-dihydro-11H-imidazo[2,1-b][3]benzazepin-11-ylidene)-1-piperidinyl]ethyl]-7-methyl-5H-thiazolo[3,2-a]pyrimidin-5-one; mp. 181.8° C. (comp. 1.13).

Example 27

A mixture of 0.83 g of chloroacetonitrile, 2.65 g of compound (1.04), 1.1 g of N,N-diethylethanamine and 80 ml of N,N-dimethylacetamide was stirred for 18 hours at room temperature. The reaction mixture was poured into water and the product was extracted with dichloromethane. The extract was dried, filtered and evaporated and the residue was crystallized from acetonitrile. The product was filtered off and dried, yielding 2.0 g (65.7%) of 4-(5,6-dihydro-11H-imidazo[2,1-b][3]-benzazepin-11-ylidene)-1-piperidineacetonitrile; mp. 220.4° C. (comp. 1.26).

Example 28

A mixture of 1.0 g of 3-chloro-2-methyl-1-propene, 2.6 g of compound (1.04), 1.6 g of sodium carbonate and 50 ml of N,N-dimethylacetamide was stirred for 20 hours at 50° C. After cooling, there were added 100 ml of ethyl acetate. The whole was washed with water (3x), dried, filtered and evaporated. The residue was purified by column chromatography (silica gel; CH$_2$Cl$_2$/CH$_3$OH 95:5). The eluent of the desired fraction was evaporated and the residue was converted into the (E)-2-butene-dioate (2:3) salt in 2-propanol. The salt was filtered off and dried, yielding 2.8 g (56.7%) of 6,11-dihydro-11-[1-(2-methyl-2-propenyl)-4-piperidinylidene]-5H-imidazo[2,1-b][3]benzazepine (E)-2-butenedioate (2:3); mp. 179.5° C. (comp. 1.08).

Example 29

A mixture of 1.57 g of 4-chloro-2-methyl-2-butene (dissolved in N,N-dimethylformamide), 2.65 g of compound (1.04), 1.1 g of sodium carbonate, 0.01 g of potassium iodide and 100 ml of N,N-dimethylacetamide was stirred for 18 hours at room temperature. The reaction mixture was poured into water and the product was extracted with dichloromethane. The extract was dried, filtered and evaporated. The residue was purified twice by column chromatography (silica gel; CH$_2$Cl$_2$/CH$_3$OH/CH$_3$OH(NH$_3$) 90:10:1; HPLC; Lichroprep RP18; CH$_3$COONH$_4$ in H$_2$O 0.5% /CH$_3$OH /CH$_3$CN 40:55:5). The eluent of the desired fraction was evaporated and the residue was crystallized from 2,2'-oxybispropane. The product was filtered off and dried, yielding 0.25 g (7.5%) of 6,11-dihydro-11-[1-(3-methyl-2-butenyl)-4-piperidinylidene]-5H-imidazo[2,1-b][3]benzazepine; mp. 127.2° C. (comp. 1.09).

Example 30

A mixture of 19 g of compound (2.03), 6 g of chloroacetonitrile, 8 g of N,N-diethylethanamine and 100 ml of N,N-dimethylformamide was stirred for 18 hours at room temperature. The reaction mixture was evaporated and the residue was taken up in water. The product was extracted with dichloromethane and the extract was dried, filtered and evaporated. The residue was purified by column chromatography (silica gel; CH$_2$Cl$_2$/CH$_3$OH 95:5). The eluent of the desired fraction was evaporated and the residue was crystallized from acetonitrile. The product was filtered off and dried, yielding 4.15 g (19.2%) of 4-(9-fluoro-5,6-dihydro-11H-imidazo[2,1-b][3]-benzazepin- 11-ylidene)-1-piperidineacetonitrile; mp. 198.3° C. (comp. 2.08).

Example 31

To a stirred mixture of 2.83 g of compound (2.03), 2.12 g of sodium carbonate, 50 ml of N,N-dimethylformamide and 1 g of potassium iodide there were added dropwise 25.4 g of 4-chloro-2-methyl-2-butene (dissolved in N,N-dimethyl-formamide). Stirring at room temperature was continued for 50 hours. The reaction mixture was diluted with water and extracted with 4-methyl-2-pentanone. The extract was dried, filtered and evaporated and the residue was purified by column chromatography (silica gel; CH$_2$Cl$_2$/CH$_3$OH(NH$_3$) 95:5). The eluent of the desired fraction was evaporated and the residue was converted into the (Z)-2-butenedioate (1:2) salt in 2-propanone. The salt was filtered off and dried, yielding 2.65 g (45.4%) of 9-fluoro-6,11-dihydro-11-[1-(3-methyl-2-butenyl)-4-piperidinylidene]-5H-imidazo-[2,1-b][3]benzazepine (Z)-2-butenedioate (1:2); mp. 203.4° C. (comp. 2.04).

Example 32

A mixture of 1.5 g of 3-bromo-1-propene, 2.65 g of compound (1.04), 1.0 g of sodium hydrogen carbonate and 100 ml of ethanol was stirred for 5 hours at reflux temperature. The reaction mixture was evaporated and the residue was taken up in water. The product was extracted with 4-methyl-2-pentanone and the extract was dried, filtered and evaporated. The residue was purified by column chromatography (silica gel; CH$_2$Cl$_2$/CH$_3$OH/CH$_3$OH(NH$_3$) 90:10:0→90:10:1). The eluent of the desired fraction was evaporated and the residue was converted into the (Z)-2-butene-dioate (1:2) salt in 2-propanone. The salt was filtered off and dried for 2 hours in vacuo at 100° C., yielding 1.1 g (20.5%) of 6,11-dihydro-11-[1-(2-propenyl)-4-piperidinylidene]-5H-imidazo-[2,1-b][3]benzazepine (Z)-2-butenedioate (1:2); mp. 160.8° C. (comp. 1.07).

Example 33

A mixture of 2.7 g of compound (3.04), 1 g of polyoxymethylene, 2 ml of a solution of thiophene in methanol 4% and 150 ml of methanol was hydrogenated at normal pressure and 50° C. in the presence of 1 g of palladium-on-charcoal catalyst 10%. After the calculated amount of hydrogen was taken up, the catalyst was filtered off and the filtrate was evaporated. The residue was purified by column chromatography (silica gel; CH$_2$Cl$_2$/CH$_3$OH(NH$_3$) 95:5). The eluent of the desired fraction was evaporated and the residue was converted into the (E)-2-butenedioate (1:2) salt in 2-propanol. The salt was filtered off and dried, yielding 3.1 g (59.0%) of 6,11-dihydro-8-methyl-11 -(1-methyl-4-piperidinylidene )-5H-imidazo[2,1-b][3]benzazepine (E)-2-butenedioate (1:2); mp. 211.0° C. (comp. 3.05).

Example 34

A mixture of 2.7 g of compound (5.01), 2 g of polyoxymethylene, 2 ml of a solution of thiophene in methanol 4% and 150 ml of methanol was hydrogenated at normal pressure and room temperature in the presence of 2 g of platinum-on-charcoal catalyst 5%. After the calculated amount of hydrogen was taken up, the catalyst was filtered off and the filtrate was evaporated. The residue was partitioned between dichloromethane and NH$_4$OH. The aqueous layer was separated and re-extracted with dichloromethane. The combined organic layers were dried, filtered and evaporated. The residue was crystallized from a mixture of 2,2'-oxybispropane and acetonitrile (2x). The product was filtered off and dried, yielding 0.76 g (26.2%) of 6,11-dihydro-11-(1-methyl-4-piperidinyl)- 5H-imidazo-[2,1-b][3]benzazepine hemihydrate; mp. 117.8° C. (comp. 5.02).

Example 35

A mixture of 2.65 g of compound (1.04), 20 ml of acetic acid and 15 ml of 2-propanone was stirred for 2 hours at room temperature under nitrogen. There were added portionwise 1.5 g of sodium tetrahydroborate and stirring was continued for 18 hours. The reaction mixture was diluted with water and basified with NaOH 15%. The product was extracted with dichloromethane and the extract was dried, filtered and evaporated. The residue was purified by column chromatography (silica gel; CH$_2$Cl$_2$/CH$_3$OH/CH$_3$OH(NH$_3$) 90:10:1). The eluent of the desired fraction was evaporated and the residue was converted into the (Z)-2-butenedioate (1:2) salt in 2-propanone. The salt was filtered off and dried, yielding 2.5 g (46.3%) of 6,11-dihydro-11-[1-(1-methylethyl)-4 -piperidinylidene]- 5H-imidazo[2,1-b][3]benzazepine (Z)-2-butenedioate (1:2); mp. 183.6° C. (comp. 1.06).

Example 36

A mixture of 4 g of compound (4.03), 2 ml of acetic acid, 3 g of sodium acetate and 20 ml of formaldehyde 37% was stirred for 50 hours at reflux temperature. The reaction mixture was evaporated and the residue was taken up in water. The whole was basified with NaOH (aq.) and extracted with a mixture of dichloromethane and methanol. The extract was dried, filtered and evaporated and the residue was purified by column chromatography (silica gel; CH$_2$Cl$_2$/CH$_3$OH 95:5→CH$_2$Cl$_2$/CH$_3$OH(NH$_3$) 90:10). The eluent of the desired fraction was evaporated and the residue was crystallized from a mixture of acetonitrile and 2,2'-oxybispropane. The product was filtered off and dried, yielding 0.4 g (9.2%) of 6,11-dihydro-3-methyl-11-(1-methyl-4-piperidinylidene)- 5H-imidazo-[2,1-b][3]benzazepine-2-methanol; mp. 166.8° C. (comp. 4.21).

Example 37

A mixture of 1.6 g of (2-pyridinyl)ethene, 2.7 g of compound (5.01) and 100 ml of 1-butanol was stirred for 18 hours at reflux temperature. The reaction mixture was evaporated and the residue was purified by column chromatography (silica gel; CH$_2$Cl$_2$/CH$_3$OH/CH$_3$OH:NH$_3$ 90:10:1). The eluent of the desired fraction was evaporated and the residue was crystallized from acetonitrile. The product was filtered off and dried, yielding 1.7 g (45.6%) of 6,11-dihydro-11-[1-[2-(2-pyridinyl)ethyl]- 4-piperidinyl]- 5H-imidazo-[2,1-b][3]benzazepine; mp. 170.3° C. (comp. 5.04).

Example 38

Through a stirred mixture of 32 g of compound (1.04) and 300 ml of methanol was bubbled gaseous oxirane for 1 hour at room temperature. After stirring for 3 hours at room temperature, the mixture was purified by column chromatography (silica gel; CH$_2$Cl$_2$/CH$_3$OH/CH$_3$OH:NH$_3$ 90:10:0→90:10:5). The eluent of the desired fraction was evaporated and the residue was converted into the (Z)-2-butenedioate salt in acetonitrile. The salt was filtered off and dried, yielding 15 g (23.1%) of 4-(5,6-dihydro-11H-imidazo[2,1-b][3]benzazepin-11-ylidene)-1-piperidineethanol (Z)-2-butenedioate(1:2); mp. 145.7° C. (comp. 1.30).

Example 39

A solution of 9.6 g of compound (4.08) in 300 ml of methanol/NH$_3$ was hydrogenated in the presence of 3 g of Raney Nickel catalyst. After complete reaction, the catalyst was filtered off and the filtrate was evaporated, yielding 12.5 g (100%) of 4-(5,6-dihydro-3-methyl-11H-imidazo[2,1-b][3]benzazepin-11-ylidene)-1-piperidineethanamine (comp. 4.09).

Example 40

0.57 g of lithium aluminum hydride were added portionwise to 100 ml of tetrahydrofuran under nitrogen. A solution of 2.3 g of compound (1.26) in tetrahydrofuran was added dropwise and the reaction mixture was stirred for 3 hours at reflux temperature. The mixture was decomposed with 2 ml of water, 2 ml of a sodium hydroxide solution 15%. After filtration over diatomaceous earth, the filtrate was evaporated, yielding 2.3 g (97.5%) of 4-(5,6-dihydro-11H-imidazo[2,1-b][3]benzazepin-11-yl)-1-piperidineethanamine (comp. 5.07).

Example 41

A solution of 3.1 g of compound (1.30) in N,N-dimethylacetamide was added dropwise to a mixture of 0.7 g of a sodium hydride dispersion 50% and 200 ml of N,N-dimethylacetamide under nitrogen and at room temperature. After stirring for 1 hour, 1.1 g of 2-chloropyrimidine were added and the whole was stirred for 16 hours at room temperature. The reaction mixture was decomposed with water and the product was extracted with dichloromethane. The extract was dried, filtered and evaporated. The residue was purified by column chromatography (silica gel; $CH_2Cl_2/CH_3OH$ 90:10). The eluent of the desired fraction was evaporated and the residue was converted into the (Z)-2-butenedioate salt in 2-propanone. The salt was filtered off and dried, yielding 1.4 g (22.6%) of 6,11-dihydro-11-[1-[2-(2-pyrimidinyloxy)ethyl]-4-piperidinylidene]-5H-imidazo[2,1-b][3]benzazepine (Z)-2-butenedioate(1:2); mp. 172.6° C. (comp. 1.31).

Example 42

A mixture of 3.3 g of 2-chloropyrimidine, 3.2 g of compound (4.09), 1.26 g of sodium hydrogen carbonate and 200 ml of ethanol was stirred for 18 hours at reflux temperature. The reaction mixture was evaporated and the residue was taken up in water. The product was extracted with dichloromethane. The extract was dried, filtered and evaporated. The residue was purified by column chromatography (silica gel; $CH_2Cl_2/CH_3OH$ 95:5→90:10). The eluent of the desired fraction was evaporated and the residue was crystallized from acetonitrile. The product was filtered off and dried, yielding 2.56 g (63.9%) of N-[2-[4-(5,6-dihydro-3-methyl-11H-imidazo[2,1-b][3]benzazepin-11-ylidene)-1-piperidinyl]ethyl]-2-pyrimidinamine; mp. 17 1.3° C. (comp. 4.10).

Example 43

A mixture of 2.0 g of 5-bromo-1,3,4-thiadiazole-2-amine, 3.42 g of compound (1.27), 1.2 g of sodium carbonate, 0.01 g of potassium iodide and 200 ml of N,N-dimethylacetamide was stirred for 4 hours at 120° C. The reaction mixture was evaporated and the residue was stirred in dichloromethane. The organic layer was dried, filtered and evaporated. The residue was purified by column chromatography (silica gel; $CH_2Cl_2/CH_3OH/$ $CH_3OH:NH_3$ 90:10:1→90:7:3). The eluent of the desired fraction was evaporated and the residue was crystallized from a mixture of acetonitrile and ethanol. The product was filtered off and dried, yielding 1.62 g (36.2%) of $N^2$-[2-[4-(5,6-dihydro-11H-imidazo[2,1-b][3]benzazepin-11-ylidene)-1-piperidinyl]ethyl]-1,3,4-thiadiazole-2,5-diamine; mp. 251.4° C. (comp. 1.33).

Example 44

To a stirred mixture of 1.1 g of 3-furancarboxylic acid, 1.9 g of N,N-diethylethanamine and 200 ml of dichloromethane were added portionwise 2.4 g of 2-chloro-1-methylpyridinium iodide. After stirring for 1 hour at room temperature, a solution of 2.9 parts of compound (1.27) in dichloromethane was added dropwise. Upon completion, the reaction mixture was stirred for 18 hours at room temperature. The reaction mixture was basified with $K_2CO_3$(aq.) and extracted with dichloromethane. The extract was dried, filtered and evaporated. The residue was purified by column chromatography (silica gel; $CH_2Cl_2/CH_3OH$ 94:6→90:10). The eluent of the desired fraction was evaporated and the residue was converted into the (Z)-2-butenedioate salt in 2-propanone. The salt was filtered off and dried, yielding 1.88 g (31.5%) of N-[2-[4-(5,6-dihydro-11H-imidazo-[2,1-b][3]benzazepin-11-ylidene)-1-piperidinyl]-ethyl]-3-furancarboxamide (Z)-2-butenedioate(1:2); mp. 202.9° C. (comp. 1.35).

Example 45

A mixture of 0.6 g of isocyanatomethane, 3.1 g of compound (1.27) and 100 ml of tetrahydrofuran was stirred for 18 hours at room temperature. The reaction mixture was evaporated and the residue was crystallized from acetonitrile. The precipitated product was filtered off and dried, yielding 2.0 g (54.7%) of N-[2-[4-(5,6-dihydro-11H-imidazo-[2,1-b][3]benzazepin-11-ylidene)-1-piperidinyl]-ethyl]-N'-methylurea; mp. 178.1° C. (comp. 1.36).

Example 46 a) To a stirred and cooled (−10° C.) mixture of 18 g of carbon disulfide, 7.22 g of N,N'-methanetetraylbis[cyclohexanamine]and 150 ml of tetrahydrofuran was added dropwise a solution of 10.8 g of compound (1.27) in tetrahydrofuran. After stirring for 1 hour at room temperature, the reaction mixture was evaporated, yielding 12 g (97.5%) of 6,11-dihydro-11-[1-(2-isothiocyanatoethyl)-4-piperidinylidene]-5H-imidazo[2,1-b]-3]benzazepine (comp. 1.37).

b) A mixture of 2.7 g of 3,4-pyridinediamine, 8.8 g of compound (1.37) and 150 ml of tetrahydrofuran was stirred for 18 hours at reflux temperature, yielding 11.5 g (100%) of N-(4-amino-3-pyridinyl)-N'-[2-[4-(5,6-dihydro-11H-imidazo[2,1-b][3]benzazepin-11-ylidene)-1-piperidinyl]ethyl]thiourea (comp. 1.38).

c) A mixture of 11.5 g of compound (1.38), 7.6 g of mercury(II)oxide, 0.01 g of sulfur and 150 ml of tetrahydrofuran was refluxed for 5 hours. The reaction mixture was filtered while hot over diatomaceous earth and the filtrate was evaporated. The residue was purified by column chromatography (silica gel; $CH_2Cl_2/CH_3OH/CH_3OH:NH_3$ 90:5:5). The eluent of the desired fraction was evaporated and the residue was converted into the (E)-2-butenedioate salt in methanol. The salt was filtered off and dried, yielding 1.65 g (14.4%) of N-[2-[4-(5,6-dihydro-11H-imidazo[2,1-b][3]benzazepin-11-ylidene)-1-piperidinyl]ethyl]-1H-imidazo[4,5-c]pyridin-2-amine (E)-2-butenedioate(1:3) hemihydrate; mp. 203.0° C. (comp. 1.39).

Example 47

1 g of gaseous methanamine was bubbled through 100 ml of tetrahydrofuran. A solution of 3.5 g of compound (1.37) in tetrahydrofuran was added and the reaction mixture was stirred for 2 hours at room temperature. After evaporation, the residue was purified by column chromatography (silica gel; CH$_2$Cl$_2$/CH$_3$OH/CH$_3$OH:NH$_3$ 90:10:0→90:10:1). The eluent of the desired fraction was evaporated and the residue was crystallized from 2,2'-oxybispropane. The crystallized product was filtered off and dried, yielding 0.9 g (23.0%) of N-[2-[4-(5,6-dihydro-11H-imidazo[ 2,1-b][3]benzazepin-11-ylidene)-1-piperidinyl]ethyl]-N'-methylthiourea hemihydrate; mp. 155.2° C. (comp. 1.40).

Example 48 a) A mixture of 7.6 g of compound (1.30) and 100 ml of thionyl chloride was stirred for 2 hours at reflux temperature. The reaction mixture was evaporated and the residue was stirred in methylbenzene (2x). The obtained residue was dissolved in water and treated with sodium carbonate. The product was extracted with dichloromethane. The extract was dried, filtered and evaporated. The residue was purified by column chromatography (silica gel; CH$_2$Cl$_2$/CH$_3$OH95:5). The eluent of the desired fraction was evaporated and the residue was converted into the (Z)-2-butenedioate salt in 2-propanone. The salt was filtered off and dried, yielding 0.7 g (5%) of 11-[1-(2-chloroethyl)-4-piperidinylidene]-6,11-dihydro-5 H-imidazo[ 2,1-b][3]-benzazepine (Z)-2-butenedioate(1:2); mp. 169.9° C. (comp. 1.41).

b) A mixture of 2.8 g of 1-methyl-1 H-imidazol-2-thiol, 6.5 g of compound (1.41), 8.3 g of potassium carbonate and 200 ml of 2-propanone was stirred for 18 hours at reflux temperature. The reaction mixture was evaporated, the residue was taken up in dichloromethane, washed with water, dried, filtered and evaporated. The residue was purified by column chromatography (silica gel; CH$_2$Cl$_2$/CH$_3$OH90:10). The eluent of the desired fraction was evaporated and the residue was taken up in methylbenzene and treated with activated charcoal. The whole was filtered while hot, the filtrate was allowed to cool and was then evaporated. The residue was converted into the cyclohexanesulfamate salt in 2-propanone and ethanol. The salt was filtered off and dried, yielding 1.6 g (10.5%) of 6,11-dihydro-11-[1-[2-[(1-methyl-1H-imidazol-2 -yl)thio]-ethyl]- 4-piperidinylidene]-5 H-imidazo[2,1-b][3]benzazepine cyclohexanesulfamate (1:2); mp. 265.4° C. (decomp.) (comp. 1.42).

Example 49 a) A mixture of 9.6 g of methyl N-(2,2'-dimethoxyethyl)-N'-methylcarbamimidothioate hydroiodide, 9.3 g of compound (1.27) and 200 ml of 2-propanol was stirred for 18 hours at reflux temperature. The reaction mixture was evaporated, yielding 17.4 g (100%) of N-[2-[4-(5,6-dihydro-11H-imidazo[2,1-b]-[3] benzazepin-11-ylidene)-1-piperidinyl]ethyl]-N'-(2,2-dimethoxyethyl)-N"-methylguanidine monohydroiodide (comp. 1.43).

b) A mixture of 9.3 g of compound (1.43) and 200 ml of a hydrochloric acid solution was stirred for 18 hours at room temperature. The whole was treated with potassium carbonate and the product was extracted with dichloromethane. The extract was dried, filtered and evaporated. The residue was purified by column chromatography HPLC (silica gel; CHCl$_3$/CH$_3$OH98:2). The eluent of the desired fraction was evaporated and the residue was converted into the cyclohexanesulfamate salt in 2-propanone and ethanol. The salt was filtered off and dried, yielding 0.71 g (3%) of 4-(5,6-dihydro- 11 H-imidazo[2,1-b][3]benzazepin-11-ylidene)-N-(1-methyl-1H -imidazol-2-yl)-1 -piperidine-ethanamine cyclohexanesulfamate (1:3) dihydrate; mp. 153.9° C. (comp. 1.44).

Example 50

A mixture of 1.42 g of 2-mercapto-4-pyrimidinone, 3.1 g of compound (1.27) and 1 ml of N,N-dimethylacetamide was stirred for 4 hours at 140° C. After cooling, the mixture was purified by column chromatography (silica gel; CHCl$_3$/CH$_3$OH95:5). The eluent of the desired fraction was evaporated and the residue was converted into the hydrochloride salt in 2-propanone. The salt was filtered off and dried in vacuo, yielding 1.8 g (32.9%) of 2-[[2-[4-(5,6-dihydro-11 H-imidazo-[ 2,1-b][3]-benzazepin-11-ylidene)-1-piperidinyl]ethyl]amino]-4(1H)-pyrimidinone trihydrochloride dihydrate; mp. 234.8° C. (comp. 1.45).

Example 51

A mixture of 1 g of compound (4.11), 5 g of manganese(IV)oxide and 100 ml of trichloromethane was stirred for 2 hours at reflux temperature. The reaction mixture was filtered while hot over diatomaceous earth. After evaporation, the residue was purified by column chromatography (silica gel; CH$_2$Cl$_2$/CH$_3$OH95:5). The eluent of the desired fraction was evaporated and the residue was crystallized from 1,1'-oxybisethane. The product was filtered off and dried, yielding 0.48 g (48.6%) of ethyl 4-(3-formyl-5,6-dihydro-11H-imidazo[2,1-b][3]benzazepin-11-ylidene)-1-piperidine mp. 138.2° C. (comp. 4.15).

Example 52

To a stirred solution of 9.7 g of compound (4.15) in 100 ml of water was added dropwise a solution of 13.7 g of AgNO$_3$ in 50 ml of water and then a solution of 13.3 g of potassium hydroxide in 50 ml of water. After stirring for 18 hours, the reaction mixture was filtered and the filtrate acidified with hydrochloric acid. After evaporation, the residue was stirred in methanol, the precipitate was filtered off and the filtrate was evaporated. The residue was purified by column chromatography (silica gel; NH$_4$OAc/H$_2$O/CH$_3$OH55:0.5:45). The eluent of the desired fraction was evaporated and the residue was stirred in 2-propanone and activated charcoal. The precipitate was filtered off and the filtrate was evaporated. The residue was crystallized first from 2,2'-oxybispropane and then from acetonitrile. The product was filtered off and dried, yielding 0.3 g (3%) of 11-[1-(ethoxycarbonyl)-4-piperidinylidene]-6,11-dihydro- 5 H-imidazo[2,1-b][ 3]benzazepine-3-carboxylic acid; mp. 182.2° C. (comp. 4.17).

Example 53

To a stirred mixture of 2.93 g of compound (4.03), 1.3 g of sodium acetate and 30 ml of acetic acid was added dropwise a solution of 1.6 g of bromine in 20 ml of acetic acid. After stirring for 1 hour at 30° C., the mixture was evaporated and the residue was taken up in water. The aqueous solution was treated with sodium hydroxide and the product was extracted with dichloromethane. The extract was dried, filtered and evaporated. The residue was purified by column chromatography (silica gel; CH$_2$Cl$_2$/CH$_3$OH95:5→CH$_2$Cl$_2$/CH$_3$OH/CH$_3$OH:NH$_3$90:8:2). The eluent of the desired fraction was evaporated and the residue was boiled in acetonitrile. After cooling, the precipitated product was filtered off and dried, yielding 0.96 g (25.8%) of 2-bromo-6,11-dihydro-3 -methyl-11-(1-methyl-4-piperidinylidene)-5H-imidazo-[2,1-b][3]benzazepine; mp.

116.0° C. (comp. 4.22).

Example 54 a) A mixture of 6.1 g of 6,11-dihydro-11-(1-methyl-4-piperidinylidene)-5H-imidazo-[ 2,1-b][3]benzazepine-3-carboxaldehyde and 5.3 g of monoethyl ester propanedioic acid in 1 ml of piperidine and 50 ml of pyridine was stirred and refluxed for 4 hours. The reaction mixture was evaporated and the residue was taken up in water. The product was extracted with dichloromethane, dried, filtered and evaporated, yielding 13 g (100% ) of ethyl 3-[5,6-dihydro-11-(1-methyl-4-piperidinylidene )- 11H-imidazo[2,1-b][3]benzazepin-3-yl]-2-propenoate (comp. 4.27).

b) A solution of 1.12 g of potassium hydroxide in 40 ml of water was added dropwise to a stirred mixture of 13 g of compound (4.27) in 20 ml of tetrahydrofuran. The mixture was stirred overnight, acidified with HCl and evaporated. The residue was purified by HPLC Lichroprep 18 25 μm (eluent: NH$_4$OAc/H$_2$O/ CH$_3$CN 0.5/89.5/10 H$_2$OCH$_3$CN90/10). The eluent of the desired fraction was evaporated and the residue was stirred in 500 ml of 2-propanone, decolourized with activated charcoal and filtered over diatomaceous earth. The filtrate was evaporated and the residue was stirred in 1,1'-oxybisethane. The product was filtered off and dried, yielding 0.9 g (11.9%) of ethyl (E)-3-[5,6-dihydro-11-(1-methyl-4-piperidinylidene)-11H-imidazo[2,1-b][ 3]benzazepin-3-yl]-2-propenoic acid sesquihydrate; mp. 207.3° C. (comp. 4.28).

Example 55 a) A mixture of 2.64 g of 2,5-dimethoxytetrahydrofuran, 3.1 g of compound (1.27), 30 ml of water and 10 ml of acetic acid was stirred for 1.5 hours at 50° C. The mixture was basified with NaOH(aq.) and the product was extracted with dichloromethane. The extract was dried, filtered and evaporated. The residue was purified by column chromatography (silica gel; CH$_2$Cl$_2$/CH$_3$OH 95:5). The eluent of the desired fraction was evaporated and the residue was crystallized from acetonitrile, yielding 1.17 g (33%) of 6,11-dihydro-11-[1-[2-(1H-pyrrol-1-yl)ethyl]-4-piperidinylidene]-5H-imidazo-[ 2,1-b][3]benzazepine; mp. 165.5° C. (comp. 1.55).

b) To 60 ml of N,N-dimethylformamide were added dropwise 5.9 g of phosphoryl chloride. After stirring for 30 minutes at room temperature, there was added a solution of 13.7 g of compound (1.55) in N,N-dimethylformamide and stirring at room temperature was continued for 1 hour. The reaction mixture was poured into a mixture of ice, water and potassium carbonate and the product was extracted with dichloromethane. The extract was dried, filtered and evaporated. The residue was purified by column chromatography (silica gel; CH$_2$Cl$_2$/CH$_3$OH 96:4). The eluent of the desired fraction was evaporated and the residue was crystallized from acetonitrile, yielding 6.4 g (43% ) of 1-[2-[4-(5,6-dihydro-11H-imidazo[2,1-b][ 3]benzazepin-11-ylidene)-1-piperidinyl] ethyl]-1H-pyrrole-2-carboxaldehyde; mp. 158.5° C. (comp. 1.56).

c) To a cooled mixture (ice-bath) of 4.4 g of compound (1.56) and 100 ml of methanol was added portionwise over 15 minutes 1.1 g of sodium tetrahydroborate. After stirring for 1 hour at room temperature, the reaction mixture was evaporated and the residue was taken up in water. The product was extracted with dichloromethane and the extract was dried, filtered and evaporated. The residue was purified by column chromatography (silica gel; CH$_2$Cl$_2$/CH$_3$OH 97:3 to 93:7). The eluent of the desired fraction was evaporated and the residue was crystallized from acetonitrile, yielding 2.74 g (62%) of 1-[2-[4-(5,6-dihydro-11H-imidazo[2,1-b][3]benzazepin-11-ylidene)-1-piperidinyl]-ethyl] -1H-pyrrole-2-methanol; mp. 147.4° C. (comp. 1.57).

Example 56 a) A mixture of 4.3 g of compound (1.27), 5.2 g of ethyl 2,5-diethoxy-tetrahydofuran- 2-carboxylate and 100 ml of acetic acid was stirred for 2 hours at 80° C. The mixture was evaporated and the residue was taken up in water. The whole was basified with potassium carbonate and the product extracted with dichloromethane. The extract was dried, filtered and evaporated. The residue was purified by column chromatography (silica gel; CH$_2$Cl$_2$/CH$_3$OH 96:4→90:10). The eluent of the desired fraction was evaporated and the residue was crystallized from acetontrile, yielding 4.3 g (70%) of ethyl 1-[2-[4-(5,6-dihydro-11H-imidazo[2,1-b][3] benzazepin-11-ylidene)-1-piperidinyl] ethyl]-1H-pyrrole-2-carboxylate; mp. 158.5° C. (comp. 1.58).

b) A mixture of 3.2 g of compound (1.58), 40 ml of sodium hydroxide (1N), 50 ml of tetrahydrofuran and 100 ml of water was stirred for 48 hours at reflux temperature. The reaction mixture was evaporated and the residue was washed with dichloromethane. The whole was neutralized with HCl (1N) and the product was extracted with dichloromethane. The organic layer was dried, filtered and evaporated. The product was crystallized successively from 2-propanone and acetonitrile, yielding 1.06 g (36%) of 1-[2-[4-(5,6-dihydro-11H-imidazo[2,1-b][3] benzazepin-11-ylidene)-1-piperidinyl]-ethyl] -1H-pyrrole-2-carboxylic acid hemihydrate; mp. 166.2° C. (comp. 1.59).

Example 57

To a mixture of 3 g of compound (3.23) and 10 ml of tetrahydrofuran was added dropwise a solution of 0.45 g of potassium hydroxide in 20 ml of water. After stirring overnight at room temperature, the reaction mixture was evaporated and the aqueous layer was washed three times with dichloromethane. The aqueous layer was discoloured with activated charcoal, filtered over diatomaceous earth and concentrated. The aqueous layer was neutralized with HCl till pH=7. The precipitate was filtered off, washed with water and dried, yielding 1.26 g (40%) of 4-(8-fluoro-5,6-dihydro-11 H-imidazo[2,1-b][ 3]benzazepin-11-ylidene)-1-piperidinepropanoic acid dihydrate; mp. 136.1° C. (comp. 3.31).

Example 58

A mixture of 1.9 g of compound (3.28) and 50 ml of hydrobromic acid 48% (aq.) was stirred for 2 hours at reflux temperature. The reaction mixture was evaporated and the residue was taken up in water and basified with potassium carbonate. The product was extracted with dichloromethane and the extract was dried, filtered and evaporated. The residue was purified by column chromatography (silica gel; CH$_2$Cl$_2$/CH$_3$OH 94:6→90:10). The eluent of the desired fraction was evaporated and the residue was converted into the (E)-2-butenedioate salt (2:3) in 2-propanol; yielding 1.15 g (42%) of 4-[2-4-( 5,6-dihydro-8-methyl-11 H-imidazo[2,1-b][3]benzazepin-11-ylidene)-1-piperidinyl]

-ethyl] phenol hemiethanolate hemihydrate (E)-2-butenedioate(2:3); mp. 176.0° C. (comp. 3.30).

Example 59 a) A mixture of 4.3 g of compound (4.16), 9 g of methyl (methylthio)methanesulfoxide 97%, 50 ml of tetrahydrofuran and 20 ml of a solution of benzyltrimethylammonium hydroxide in methanol 40% was stirred for 18 hours at reflux temperature. The reaction mixture was evaporated and the residue was taken up in water. The product was extracted with dichloromethane and the extract was dried, filtered and evaporated. The residue was co-evaporated with methylbenzene (2x) and then taken up in 50 ml of methanol. This solution was cooled on ice and gasueous hydrochloride was bubbled through for ½ hour. After stirring overnight, the whole was evaporated. The residue was taken up in water and basified with potassium carbonate. The product was extracted with dichloromethane and further purified by column chromatography (silica gel; $CH_2Cl_2/C_2H_5OH(NH_3)$ 97:3). The desired fraction was evaporated, yielding 3.15 g (29.9%) of methyl [5,6-dihydro-11-(1-methyl-4-piperidinylidene)-11H-imidazo-[2,1-b][3]benzazepin-3-yl]acetate (comp. 4.30).

b) To a stirred mixture of 3.15 g of compound (4.30) and 10 ml of tetrahydrofuran there was added dropwise a solution of 0.56 g of potassium hydroxide in 20 ml of water. Stirring was continued overnight. The organic solvent was evaporated and the remaining aqueous layer was successively washed with dichloromethane (3x) and stirred with activated charcoal. After filtration, the whole was concentrated and then neutralized to pH 7. The product was filtered off and purified by column chromatography (RP 18; $CH_3COONH_4$(0.5% in $H_2O$)/$CH_3CN$ 90:10). The eluent of the desired fraction was evaporated and the residue was recrystallized from acetonitrile, yielding 1.39 g (45.9%) of [5,6-dihydro-11-(1-methyl-4-piperidinylidene)-11H-imidazo[2,1-b] [3]benzazepin-3-yl] acetic acid (comp. 4.31).

All compounds listed in Tables 1–7 were prepared following methods of preparation described in examples 13–59, as is indicated in the column Ex. No.

TABLE 1

| Co. No. | Ex. No. | L— | Physical data |
|---|---|---|---|
| 1.01 | 13 | $CH_3$— | mp. 209.3° C./$CF_3SO_3H$ |
| 1.02 | 13 | $CH_3$— | mp. 154.5° C. |
| 1.03 | 19 | $H_5C_2OOC$— | mp. 170.6° C. |
| 1.04 | 21 | H— | mp. 192.5° C./½$H_2O$.2(E)* |
| 1.05 | 34 | $C_2H_5$— | mp. 184.2° C./2(Z)* |
| 1.06 | 35 | $CH_3CH(CH_3)$— | mp. 183.6° C./2(Z)* |
| 1.07 | 32 | $CH_2$=CH—$CH_2$— | mp. 160.8° C./2(Z)* |
| 1.08 | 28 | $CH_2$=C($CH_3$)—$CH_2$— | mp. 179.5° C./3/2(E)* |
| 1.09 | 29 | $CH_3$—C($CH_3$)=CH—$CH_2$— | mp. 127.2° C. |
| 1.10 | 25 | $C_6H_5$—CH=CH—$CH_2$— | mp. 172.2° C./(E) |
| 1.11 | 33 | $C_6H_5$—$CH_2$— | mp. 207.2° C. |
| 1.12 | 26 | $CH_3O$—C_6H_4—$(CH_2)_2$— | mp. 180.5° C./2(COOH)_2 |
| 1.13 | 26 | 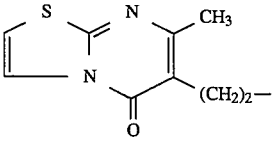 | mp. 181.8° C. |
| 1.14 | 25 | 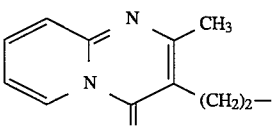 | mp. 197.8° C./$H_2O$.3(E)* |

TABLE 1-continued

| Co. No. | Ex. No. | L— | Physical data |
|---|---|---|---|
| 1.15 | 37 | 2-pyridyl-(CH₂)₂— | mp. 163.8° C. |
| 1.16 | 28 | (5-methyl-1H-imidazol-4-yl)-CH₂— | mp. 199.0° C. |
| 1.17 | 25 | (2-amino-1,6-dimethyl-6-oxo-pyrimidin-5-yl)-(CH₂)₂— | mp. 257.4° C. |
| 1.18 | 34 | furan-2-yl-CH₂— | mp. 160.3° C. |
| 1.19 | 26 | (2-methyl-oxazol-4-yl)-CH₂— | mp. 162.1° C./H₂O.2(E)* |
| 1.20 | 25 | (2-oxo-1,3-oxazolidin-3-yl)-(CH₂)₂— | mp. 188.8° C./½(E)* |
| 1.21 | 25 | (1-ethyl-5-oxo-1,2,3,4-tetrazol-4-yl) $H_5C_2-N$... $N-(CH_2)_2-$ | mp. 170.7° C./2(Z)* |
| 1.22 | 25 | (2-oxo-2,3-dihydro-1H-benzimidazol-1-yl)-(CH₂)₃— | mp. 194.7° C. |
| 1.23 | 25 | $C_2H_5-O-(CH_2)_2-$ | mp. 176.5° C./2(Z)* |
| 1.24 | 25 | $CH_3-HC(CH_3)-NH-C(=O)-(CH_2)_2-$ | mp. 165.5° C. |
| 1.25 | 25 | $H_5C_2OOC-NH-(CH_2)_2-$ | mp. 167.2° C./2(E)* |
| 1.26 | 27 | $NC-CH_2-$ | mp. 220.4° C. |
| 1.27 | 21 | $H_2N-(CH_2)_2-$ | — |

TABLE 1-continued

| Co. No. | Ex. No. | L— | Physical data |
|---|---|---|---|
| 1.28 | 39 | H$_2$N—(CH$_2$)$_2$— | mp. 186.6° C./½H$_2$O.3(E)* |
| 1.29 | 38 | HO—(CH$_2$)$_2$— | mp. 225.1° C./CF$_3$SO$_3$H |
| 1.30 | 38 | HO—(CH$_2$)$_2$— | mp. 145.7° C./2(Z)* |
| 1.31 | 41 | pyrimidin-2-yl—O—(CH$_2$)$_2$— | mp. 172.6° C./2(Z)* |
| 1.32 | 42 | pyrimidin-2-yl—NH—(CH$_2$)$_2$— | mp. 165.1° C. |
| 1.33 | 43 | 5-amino-1,3,4-thiadiazol-2-yl—NH—(CH$_2$)$_2$— | mp. 251.4° C. |
| 1.34 | 43 | thiazol-2-yl—NH—(CH$_2$)$_2$— | mp. 205.5° C./½H$_2$O/4** |
| 1.35 | 44 | furan-2-yl—C(O)—NH—(CH$_2$)$_2$— | mp. 202.9° C./2(Z)* |
| 1.36 | 45 | CH$_3$—NH—C(O)—NH—(CH$_2$)$_2$— | mp. 178.1° C. |
| 1.37 | 46a | SCN—(CH$_2$)$_2$— | — |
| 1.38 | 46b | (4-amino-pyridin-3-yl)—NH—C(S)—NH—(CH$_2$)$_2$— | — |
| 1.39 | 46c | imidazo[4,5-b]pyridin-2-yl—NH—(CH$_2$)$_2$— | mp. 203.0° C./½H$_2$O.3(E)* |
| 1.40 | 47 | CH$_3$—NH—C(S)—NH—(CH$_2$)$_2$— | mp. 155.2° C./½H$_2$O |
| 1.41 | 48 | Cl—(CH$_2$)$_2$— | mp. 169.9° C./2(Z)* |
| 1.42 | 48 | (1-methyl-imidazol-2-yl)—S—(CH$_2$)$_2$— | mp. 265.4° C. (dec.)/2** |

TABLE 1-continued

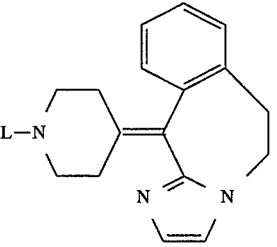

| Co. No. | Ex. No. | L— | Physical data |
|---|---|---|---|
| 1.43 | 49a | CH₃O—CH(OCH₃)—CH₂—NH—C(=N—CH₃)—NH—(CH₂)₂— | HI |
| 1.44 | 49b | 1-methyl-imidazol-2-yl-NH—(CH₂)₂— | mp. 153.9° C./2H₂O.3** |
| 1.45 | 50 | 4-oxo-1H-pyrimidin-2-yl-NH—(CH₂)₂— | mp. 234.8° C./2H₂O. 3HCl |
| 1.46 | 26 | 4-F-C₆H₄—C(=O)—(CH₂)₃— | mp. 161.0° C. |
| 1.47 | 38 | C₆H₅—O—CH₂—CH(OH)—CH₂— | 2-(E)*/mp. 156.4° C. |
| 1.48 | 28 | H₅C₂—O—CO—(CH₂)₂— | — |
| 1.49 | 27 | 2-(methoxycarbonyl)-biphenyl-4′-yl-CH₂— | mp. 131.5° C. |
| 1.50 | 27 | 4-CH₃O—C₆H₄—(CH₂)₂— | (E)*.½H₂O.½ethanolate/ mp. 127.4° C. |
| 1.51 | 25 | 4-F-C₆H₄—O—(CH₂)₃— | mp. 130.3° C. |
| 1.52 | 25 | (1,4,6-trimethyl-2-oxo-1,2-dihydropyrimidin-... derivative)—(CH₂)₂— | mp. 195.9° C. |

TABLE 1-continued
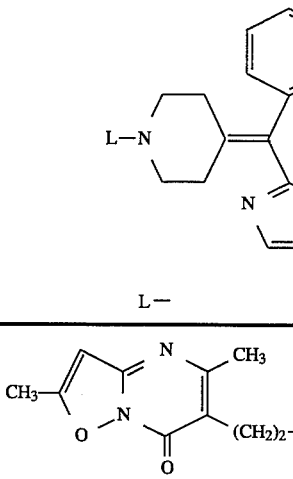
| Co. No. | Ex. No. | L— | Physical data |
|---|---|---|---|
| 1.53 | 25 | 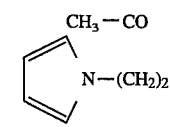 | mp. 202.9° C. |
| 1.54 | 24 | CH₃—CO | mp. 182.1° C. |
| 1.55 | 55a | 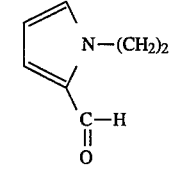 | mp. 165.5° C. |
| 1.56 | 55b | 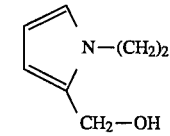 | mp. 158.5° C. |
| 1.57 | 55c | 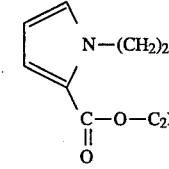 | mp. 147.4° C. |
| 1.58 | 56a | 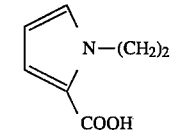 | mp. 158.5° C. |
| 1.59 | 56b | | ½H₂O/mp. 166.2° C. |
| 1.60 | 57 | HOOC—(CH₂)₂— | 2 H₂O/mp. 154.9° C. |
| 1.61 | 57 | 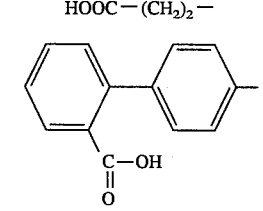 | ethanolate(1:1) mp. 208.6° C. |
\*: 2-butenedioate
\*\*: cyclohexanesulfamate TABLE 2
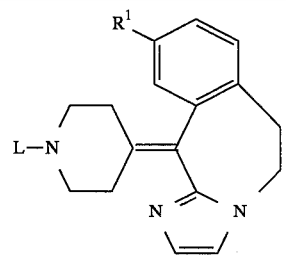
| Co. No. | Ex. No. | L— | $R^1$ | Physical data |
|---|---|---|---|---|
| 2.01 | 13 | $CH_3-$ | F | mp. 195.7° C./2(E)* |
| 2.02 | 19 | $H_5C_2OOC-$ | F | mp. 175.2° C. |
| 2.03 | 21 | H— | F | mp. 180.1° C. |
| 2.04 | 31 | $CH_3-C(CH_3)=CH-CH_2-$ | F | mp. 203.4° C./2(Z)* |
| 2.05 | 25 | 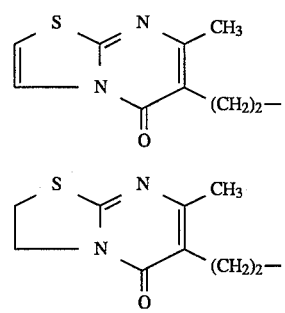 | F | mp. 168.9° C./½H$_2$O.⅝(E)* |
| 2.06 | 25 | 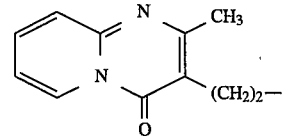 | F | mp. 162.2° C./½H$_2$O.⅝(E)* |
| 2.07 | 25 | 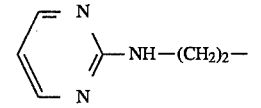 | F | mp. 201.9° C./3(E)* |
| 2.08 | 30 | $NC-CH_2-$ | F | mp. 198.3° C. |
| 2.09 | 39 | $H_2N-(CH_2)_2-$ | F | — |
| 2.10 | 42 | 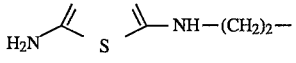 | F | mp. 165.1° C./3(Z)* |
| 2.11 | 43 | 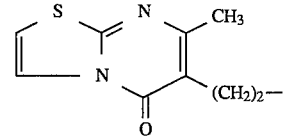 | F | mp. 238.6° C. |
| 2.12 | 13 | H— | $CH_3-$ | mp. 203.1° C. |
| 2.13 | 24 | $H_5C_2OOC-$ | $CH_3-$ | mp. 156.5° C. |
| 2.14 | 33 | $CH_3-$ | $CH_3-$ | mp. 214.3° C. |
| 2.15 | 26 | 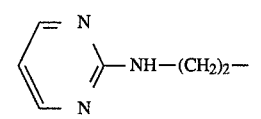 | $CH_3-$ | mp. 202.2° C. |
| 2.16 | 30 | $NC-CH_2-$ | $CH_3-$ | — |
| 2.17 | 39 | $H_2N-(CH_2)_2-$ | $CH_3-$ | mp. 219.3° C./3(E)* |
| 2.18 | 42 | 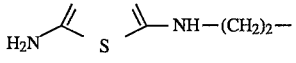 | $CH_3-$ | mp. 131.1° C. |

TABLE 2-continued

[Structure: L-N-piperidine connected via =C to benzene ring bearing R¹, fused to N-containing bicyclic imidazole system]

| Co. No. | Ex. No. | L— | R¹ | Physical data |
|---|---|---|---|---|
| 2.19 | 26 | CH₃O-C₆H₄-(CH₂)₂— | CH₃— | mp. 192.6° C./½(COOH)₂ |
| 2.20 | 44 | furan-C(O)-NH-(CH₂)₂— | CH₃— | mp. 214.2° C./2(Z)* |
| 2.21 | 13 | CH₃— | Br | mp. 213.4° C. |
| 2.22 | 25 | [1,3-dimethyl-6-methyl-pyrimidin-4(1H)-one-5-yl]-(CH₂)₂— | F | mp. 187.2° C./H₂O |

*: 2-butenedioate

TABLE 3

[Structure: L-N-piperidine connected via =C to benzene ring bearing R², fused to N-containing bicyclic imidazole system]

| Co. No. | Ex. No. | L— | R² | Physical data |
|---|---|---|---|---|
| 3.01 | 14 | CH₃— | CH₃O— | mp. 190.3° C./2(Z)* |
| 3.02 | 19 | H₅C₂OOC— | CH₃O— | mp. 104.4° C. |
| 3.03 | 21 | H— | CH₃O— | mp. 184.4° C. |
| 3.04 | 13 | H— | CH₃— | mp. 221.9° C./2(E)* |
| 3.05 | 33 | CH₃— | CH₃— | mp. 211.0° C./2(E)* |
| 3.06 | 25 | [thiazine-fused pyrimidinone with CH₃]-(CH₂)₂— | CH₃— | mp. 199.8° C. |
| 3.07 | 25 | [thiazole-fused pyrimidinone with CH₃]-(CH₂)₂— | CH₃— | mp. 214.2° C. |

TABLE 3-continued

[Structure: piperidinylidene linked to benzene ring bearing R² (para) and ethylene bridge to imidazo fused system, with L-N on piperidine]

| Co. No. | Ex. No. | L— | R² | Physical data |
|---|---|---|---|---|
| 3.08 | 25 | [3-methyl-2-(pyridin-2-yl)-4-oxo-pyrimidine with (CH₂)₂—] | CH₃— | mp. 162.3° C./H₂O.3(E)* |
| 3.09 | 25 | [3-methyl-4-oxo-thiazino-pyrimidine with (CH₂)₂—] | CH₃— | mp. 235.1° C./2H₂O.3HCl |
| 3.10 | 13 | CH₃— | Cl | mp. 186.6° C. |
| 3.11 | 19 | H₅C₂OOC— | Cl | mp. 140.3° C. |
| 3.12 | 23 | H— | Cl | mp. 197.1° C. |
| 3.13 | 26 | [3-methyl-4-oxo-thiazolo-pyrimidine with (CH₂)₂—] | Cl | mp. 217.6° C. |
| 3.14 | 30 | NC—CH₂— | Cl | — |
| 3.15 | 15 | CH₃— | F | mp. 152.4° C. |
| 3.16 | 19 | H₅C₂OOC— | F | mp. 149.4° C. |
| 3.17 | 21 | H— | F | — |
| 3.18 | 26 | [3-methyl-4-oxo-thiazolo-pyrimidine with (CH₂)₂—] | F | mp. 192.2° C./H₂O.½(E)* |
| 3.19 | 29 | H₃CO—C₆H₄—(CH₂)₂— | OCH₃ | 3/2(E)*.ethanolate/ mp. 150.3° C. |
| 3.20 | 32 | [pyrimidin-2-yl-NH—(CH₂)₂—] | Cl | ethanedioate(1:2)/mp. 206.7° C. |
| 3.21 | 37 | [pyridin-2-yl—(CH₂)₂—] | Cl | mp. 171.3° C. |
| 3.22 | 39 | H₂N—(CH₂)₂— | Cl | — |
| 3.23 | 28 | H₅C₂—O—CO—(CH₂)₂— | F | mp. 114.6° C. |
| 3.24 | 27 | NC—CH₂— | F | mp. 204.7° C. |

TABLE 3-continued

[Structure: piperidine with L—N substituent, double bond to carbon connected to phenyl (bearing R² at para position and propyl at ortho position) and to an imidazole ring]

| Co. No. | Ex. No. | L— | R² | Physical data |
|---|---|---|---|---|
| 3.25 | 27 | [2-pyridinyl-N=C(CH₃)-C(=...)(CH₂)₂— with C=O] | F | mp. 211.6° C. |
| 3.26 | 27 | H₃CO-C₆H₄-(CH₂)₂— | F | mp. 149.1° C. |
| 3.27 | 25 | [2-pyridinyl-N=C(CH₃)-C(=...)(CH₂)₂— with C=O] | Cl | ethanedioate(2:5), ½ ethanolate/mp. 170.7° C. |
| 3.28 | 25 | H₃CO-C₆H₄-(CH₂)₂— | CH₃ | cyclohexylsulfamate(1:2), H₂O/mp. 149.8° C. |
| 3.29 | 25 | [2-(2-oxo-2,3-dihydro-1H-benzimidazol-1-yl)]-N—(CH₂)₃— | CH₃ | (E)-2-butenedioate(1:2), ½H₂O/mp. 200.3° C. |
| 3.30 | 58 | HO-C₆H₄-(CH₂)₂— | CH₃ | (E)-2-butenedioate(2:3). ½ethanolate.½H₂O/ mp. 176.0° C. |
| 3.31 | 57 | HOOC—(CH₂)₂— | F | 2H₂O/mp. 136.1° C. |
| 3.32 | 42 | 2-pyrimidinyl-NH—(CH₂)₂— | F | mp. 191.2° C. |
| 3.33 | 44 | furan-2-yl-C(=O)—NH—(CH₂)₂— | F | mp. 173.5° C. |
| 3.34 | 37 | 2-pyridinyl-(CH₂)₂— | F | mp. 177.2° C. |

TABLE 3-continued

[Structure: piperidine with L-N substituent connected via exocyclic double bond to a fused bicyclic system containing imidazole and phenyl ring with R² substituent]

| Co. No. | Ex. No. | L— | R² | Physical data |
|---|---|---|---|---|
| 3.35 | 58 | HO—⌬—(CH₂)₂— (4-hydroxyphenyl-ethyl) | F | — |
| 3.36 | 39 | H₂N—(CH₂)₂— | F | mp. 141.5° C. |

TABLE 4

[Structure: benzazepine fused system with piperidine (L-N substituent) connected via exocyclic double bond, with R² on phenyl ring and R³, R⁴ on the imidazole-type ring]

| Co. No. | Ex. No. | L— | R² | R³ | R⁴ | Physical data |
|---|---|---|---|---|---|---|
| 4.01 | 17 | CH₃— | H | H | C₆H₅ | mp. 171.5° C. |
| 4.02 | 13 | H | H | —CH₃ | H | mp. 167.0° C. |
| 4.03 | 33 | CH₃— | H | —CH₃ | H | mp. 172.2° C. |
| 4.04 | 25 | [thiazolo-pyrimidinone with CH₃ and (CH₂)₂— linker] | H | —CH₃ | H | mp. 212.4° C. |
| 4.05 | 25 | [pyrido-pyridinone with CH₃ and (CH₂)₂— linker] | H | —CH₃ | H | mp. 186.3° C./ 3(E)*.H₂O |
| 4.06 | 25 | CH₃O—⌬—(CH₂)₂— | H | —CH₃ | H | mp. 150.6° C./ 5/2(COOH)₂, H₂O |
| 4.07 | 37 | 2-pyridyl—(CH₂)₂— | H | —CH₃ | H | mp. 180.2° C./ 7/2(COOH)₂ |
| 4.08 | 30 | NC—CH₂— | H | —CH₃ | H | mp. 226.5° C. |
| 4.09 | 39 | H₂N—(CH₂)₂— | H | —CH₃ | H | — |

TABLE 4-continued

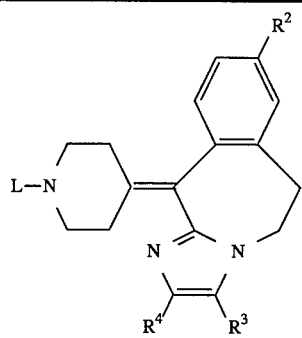

| Co. No. | Ex. No. | L— | R² | R³ | R⁴ | Physical data |
|---|---|---|---|---|---|---|
| 4.10 | 42 | ![pyrimidine]-NH-(CH₂)₂- | H | —CH₃ | H | mp. 171.3° C. |
| 4.11 | 20 | C₂H₅OOC— | H | —CH₂OH | H | mp. 191.9° C. |
| 4.12 | 21 | H | H | —CH₂OH | H | mp.>200° C. dec./⁵/₂(E)* |
| 4.13 | 33 | CH₃— | H | —CH₂OH | H | mp. 228.3° C. |
| 4.14 | 26 | [thiazolopyrimidinone group]-(CH₂)₂- | H | —CH₂OH | H | — |
| 4.15 | 51 | C₂H₅OOC— | H | —CHO | H | mp. 138.2° C. |
| 4.16 | 51 | CH₃— | H | —CHO | H | mp. 171.6° C. |
| 4.17 | 52 | C₂H₅OOC— | H | —COOH | H | mp. 182.2° C. |
| 4.18 | 20 | C₂H₅OOC— | H | —CH₂OH | —CH₂OH | — |
| 4.19 | 21 | H— | H | —CH₂OH | —CH₂OH | — |
| 4.20 | 33 | CH₃— | H | —CH₂OH | —CH₂OH | mp. 206.3° C. |
| 4.21 | 36 | CH₃— | H | —CH₃ | —CH₂OH | mp. 166.8° C. |
| 4.22 | 53 | CH₃— | H | —CH₃ | —Br | mp. 116.0° C. |
| 4.23 | 52 | CH₃— | H | —COOH | H | mp. 241.3° C. |
| 4.24 | 51 | CH₃— | F | —CHO | H | mp. 176.5° C. |
| 4.25 | 36 | CH₃— | F | —CH₂OH | H | mp. 181.5° C. |
| 4.26 | 36 | CH₃— | F | —CH₂OH | —CH₂OH | mp. 220.0° C. |
| 4.27 | 54a | CH₃— | H | —CH=CH—COOC₂H₅ | H | — |
| 4.28 | 54b | CH₃— | H | —CH=CH—COOH | H | (E)/½H₂O mp. 207.3° C. |
| 4.29 | 52 | CH₃— | F | —COOH | H | ½H₂O mp. 261.6° C. |
| 4.30 | 59a | CH₃— | H | —CH₂—COOCH₃ | H | — |
| 4.31 | 59b | CH₃— | H | —CH₂—COOH | H | — |

* = 2-butenedioate

TABLE 5
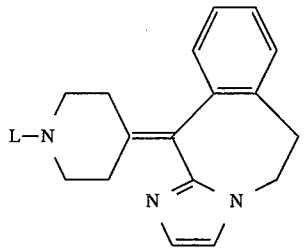
| Co. No. | Ex. No. | L— | Physical data |
|---|---|---|---|
| 5.01 | 16 | H— | mp. 220.2° C./2(E)* |
| 5.02 | 34 | CH₃— | mp. 117.8° C./½H₂O |
| 5.03 | 25 | 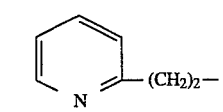 | mp. 221.6° C./2(COOH)₂/½H₂O |
| 5.04 | 37 | 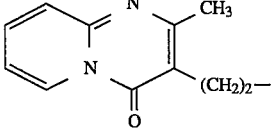 | mp. 170.3° C. |
| 5.05 | 25 | 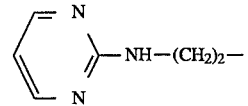 | mp. 193.3° C. |
| 5.06 | 27 | NC—CH₂— | mp. 194.7° C./½(E)* |
| 5.07 | 40 | H₂N—CH₂—CH₂— | — |
| 5.08 | 42 | 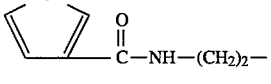 | mp. 175.1° C./7/2(E)* |
| 5.09 | 44 | 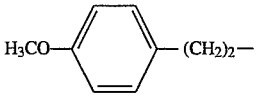 | mp. 203.5° C. |
| 5.10 | 25 | 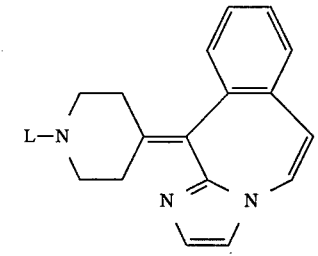 | cyclohexylsulfamate(1:2) ½H₂O/ mp. 125.4° C. |
| 5.11 | 24 | CH₃—CO— | mp. 153.8° C. |
* = 2-butenedioate
TABLE 6
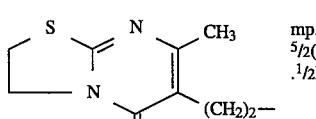
| Co. No. | Ex. No. | L— | Physical data |
|---|---|---|---|
| 6.01 | 18 | CH₃— | mp. 135.8° C. |
| 6.02 | 19 | C₂H₅OOC— | — |
| 6.03 | 22 | H— | mp. 246.9° C./2HBr ½H₂O |
| 6.04 | 27 | (thiazinyl-methyl-acyl-(CH₂)₂—) | mp. 206.4° C./2(COOH)₂ ½H₂O |
| 6.05 | 26 | (thiazinyl-methyl-acyl-(CH₂)₂—) | mp. 158.9° C./5/2(COOH)₂ .½H₂O |

TABLE 7

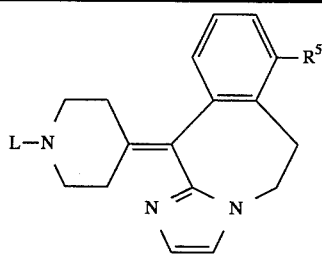

| Co. No. | Ex. No. | $R^5$ | L— | Physical data |
|---|---|---|---|---|
| 7.01 | 15 | —Cl | $CH_3$— | mp. 181.9° C. |
| 7.02 | 33 | —$CH_3$ | $CH_3$— | mp. 184.2° C. |
| 7.03 | 42 | —$CH_3$ | ![pyrimidinyl]NH—$(CH_2)_2$— | ethanedioate (2:7) $^1/_2H_2O$/ mp. 171.2° C. |
| 7.04 | 37 | —$CH_3$ | ![pyridinyl]$(CH_2)_2$— | (E)-2-butenedioate(2:3) $^1/_2H_2O$/162.2° C. |
| 7.05 | 39 | —$CH_3$ | $H_2N$—$(CH_2)_2$— | (Z)-2-butenedioate(1:3)/ mp. 192.0° C. |
| 7.06 | 13 | —$CH_3$ | H | — |
| 7.07 | 13 | —$CH_3$ | H | 2 HCl |
| 7.08 | 13 | —F | $CH_3$— | mp. 164.6° C. |
| 7.09 | 27 | —$CH_3$ | NC—$CH_2$— | mp. 194.1° C. |
| 7.10 | 25 | —$CH_3$ | ![thiazolyl-pyridinone]$(CH_2)_2$— | mp. 224.3° C. |

C. Composition Examples

The following formulations exemplify typical pharmaceutical compositions in dosage unit form suitable for systemic or topical administration to warm-blooded animals in accordance with the present invention.

"Active ingredient" (A.I.) as used throughout these examples relates to a compound of formula (I) or a compound of formula (VII) wherein Q represents ($C_{1-6}$alkyl or phenyl)oxycarbonyl, $C_{1-4}$alkylcarbonyl or $C_{1-6}$alkyl substituted with cyano or amino, a pharmaceutically acceptable acid addition salt or a stereochemically isomeric form thereof.

Example 60: Oral drops 500 g of the A.I. is dissolved in 0.5 l of 2-hydroxypropanoic acid and 1.5 l of the polyethylene glycol at 60°–80° C. After cooling to 30°–40° C. there are added 35 l of polyethylene glycol and the mixture is stirred well. Then there is added a solution of 1750 g of sodium saccharin in 2.5 l of purified water and while stirring there are added 2.5 l of cocoa flavor and polyethylene glycol q.s. to a volume of 50, l providing an oral drop solution comprising 10 mg/ml of the A.I. The resulting solution is filled into suitable containers.

Example 61: Oral solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

Example 62: Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

Example 63: Film-coated tablets

Preparation of tablet core

A mixture of 100 g of the A.I., 570 g lactose and 200 g starch is mixed well and thereafter humidified with a solution of 5 g sodium dodecyl sulfate and 10 g polyvinylpyrrolidone (Kollidon-K 90®) in about 200 ml of water. The wet powder mixture is sieved, dried and sieved again. Then there are added 100 g microcrystalline cellulose (Avicel®) and 15 g hydrogenated vegetable oil (Sterotex®). The whole is mixed well and compressed into tablets, giving 10.000 tablets, each comprising 10 mg of the active ingredient.

Coating

To a solution of 10 g methyl cellulose (Methocel 60

HG®) in 75 ml of denaturated ethanol there is added a solution of 5 g of ethyl cellulose (Ethocel 22 cps®) in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concentrated colour suspension (Opaspray K-1-2109®) and the whole is homogenated. The tablet cores are coated with the thus obtained mixture in a coating apparatus.

Example 64: Injectable Solutions 1.8 g methyl 4-hydroxybenzoate and 0.2 g propyl 4-hydroxybenzoate are dissolved in about 0.5 l of boiling water for injection. After cooling to about 50° C. there are added while stirring 4 g lactic acid, 0.05 g propylene glycol and 4 g of the A.I. The solution is cooled to room temperature and supplemented with water for injection q.s. ad 1 l volume, giving a solution of 4 mg A.I. per ml. The solution is sterilized by filtration (U.S.P. XVII p. 811) and filled in sterile containers.

Example 65: Suppositories 3 g A.I. is dissolved in a solution of 3 g 2,3-dihydroxybutanedioic acid in 25 ml polyethylene glycol 400. 12 g surfactant (SPAN®) and triglycerides (Witepsol 555®) q.s. ad 300 g are molten together. The latter mixture is mixed well with the former solution. The thus obtained mixture is poured into moulds at a temperature of 37°–38° C. to form 100 suppositories each containing 30 mg of the A.I.

We claim:

1. A compound of the formula:

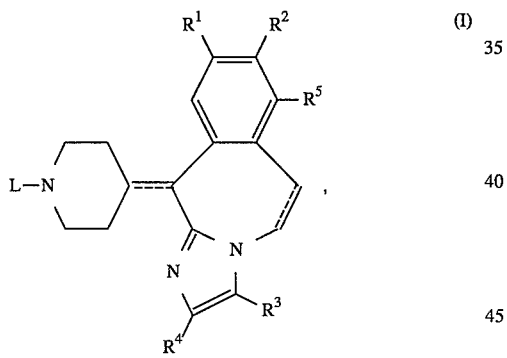

a pharmaceutically acceptable addition salt or a stereochemically isomeric form thereof, wherein:

each of the dotted lines independently represents an optional bond;

$R^1$ represents hydrogen, halo, $C_{1-4}$alkyl, or $C_{1-4}$alkyloxy;

$R^2$ represents hydrogen, halo, $C_{1-4}$alkyl, or $C_{1-4}$alkyloxy;

$R^3$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^4$ represents hydrogen, $C_{1-4}$alkyl, hydroxy$C_{1-4}$alkyl, phenyl or halo;

$R^5$ represents hydrogen, $C_{1-4}$alkyl or halo;

L represents $C_{1-6}$alkyl; $C_{1-6}$alkyl substituted with one substituent selected from the group consisting of hydroxy, halo, $C_{1-4}$alkyloxy, hydroxycarbonyl, $C_{1-4}$alkyloxycarbonyl, $C_{1-4}$alkyloxycarbonyl$C_{1-4}$alkyloxy, hydroxycarbonyl$C_{1-4}$alkyloxy, $C_{1-4}$alkyloxycarbonylamino, $C_{1-4}$alkylaminocarbonyl, $C_{1-4}$alkylaminocarbonylamino, $C_{1-4}$alkylaminothiocarbonylamino, aryl, aryloxy and arylcarbonyl; $C_{1-6}$alkyl substituted with both hydroxy and aryloxy; $C_{3-6}$alkenyl; $C_{3-6}$alkenyl substituted with aryl;

wherein each aryl is phenyl or phenyl substituted with halo, cyano, hydroxy, $C_{1-4}$alkyl, $C_{1-4}$alkyloxy, aminocarbonyl or phenyl substituted with $C_{1-4}$alkyloxycarbonyl or hydroxycarbonyl; or L represents a radical of the formula:

—Alk—Y—Het$^1$ (a-1),

—Alk—NH—CO—Het$^2$ (a-2), or

—Alk—Y—Het$^3$ (a-3); wherein

Alk represents $C_{1-4}$alkanediyl;

Y represents O, S or NH;

Het$^1$, Het$^2$ and Het$^3$ each represent:

furanyl, thienyl, oxazolyl, thiazolyl or imidazolyl each optionally substituted with one or two $C_{1-4}$alkyl substituents;

pyrrolyl or pyrazolyl optionally substituted with formyl, hydroxy$C_{1-4}$alkyl, hydroxycarbonyl, $C_{1-4}$alkyloxycarbonyl or with one or two $C_{1-4}$alkyl substituents;

thiadiazolyl or oxadiazolyl optionally substituted with amino or $C_{1-4}$alkyl;

pyridinyl, pyrimidinyl, pyrazinyl or pyridazinyl each optionally substituted with $C_{1-4}$alkyl, $C_{1-4}$alkyloxy, amino, hydroxy or halo; or imidazo[4,5-c]pyridin-2-yl;

and Het$^3$ may also represent a member selected from the group consisting of:

(a) 4,5-dihydro-5-oxo-1H-tetrazolyl substituted with $C_{1-4}$alkyl;

(b) 2-oxo-3-oxazolidinyl;

(c) 2,3-dihydro-2-oxo-1H-benzimidazol1-yl; and (d) a radical of the formula:

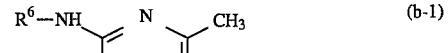

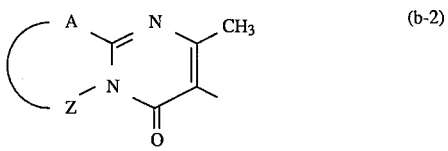

wherein:

$R^6$ represents hydrogen or $C_{1-4}$alkyl; and

A-Z represents —S—CH=CH—, —S—CH$_2$—CH$_2$—, —S—CH$_2$—CH$_2$—CH$_2$—, —CH=CH—CH=CH—, —CH$_2$—CH$_2$—CH$_2$—CH$_2$—, —N(CH$_3$)—C(CH$_3$)=CH— or —CH=C (CH$_3$)—O—.

2. A compound according to claim 1 wherein L is $C_{1-4}$alkyl or $C_{1-4}$alkyl substituted with hydroxycarbonyl or $C_{1-4}$alkyloxycarbonyl.

3. A compound according to claim 1 wherein:

$R^3$ represents hydrogen, $C_{1-4}$alkyl, formyl, hydroxy$C_{1-4}$alkyl or hydroxycarbonyl;

$R^4$ represents hydrogen, halo or hydroxy$C_{1-4}$alkyl; and

L represents $C_{1-4}$alkyl, halo$C_{1-4}$alkyl, hydroxycarbonyl$C_{1-4}$alkyl, $C_{1-4}$alkyloxycarbonyl$C_{1-4}$alkyl, $C_{1-4}$alkyloxycarbonylamino$C_{1-4}$alkyl, aryl$C_{1-4}$alkyl, propenyl, or L is a radical of the formula:

—Alk—Y—Het$^1$     (a-1),

—Alk—NH—CO—Het$^2$     (a-2), or

—Alk—Y—Het$^3$     (a-3); wherein

Het$^1$, Het$^2$ and Het$^3$ each represent furanyl oxazolyl, or thiazolyl each optionally substituted with $C_{1-4}$alkyl; thiadiazolyl optionally substituted with amino; pyridinyl; pyrimidinyl optionally substituted with hydroxy; or imidazo[4,5-c]pyridin-2-yl;

or Het$^3$ may also represent a radical of the formula (b-2):

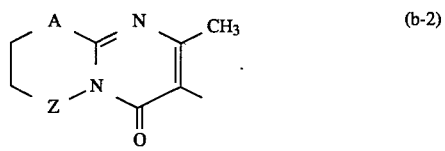

4. A compound according to claim 3 wherein $R^1$ represents hydrogen or halo;

$R^2$ represents hydrogen, halo or $C_{1-4}$alkyloxy; and

L represents hydrogen, $C_{1-4}$alkyl, halo$C_{1-4}$alkyl, hydroxycarbonyl$C_{1-4}$alkyl, $C_{1-4}$alkyloxycarbonyl$C_{1-4}$alkyl, or a radical of formula (a-1), wherein Y represents NH.

5. A compound according to claim 1 wherein said compound is selected from the group consisting of 5,6-dihydro-11-(1-methyl-4-piperidinylidene)-11H-imidazo[2,1-b][3]benzazepine;

9-fluoro-6,11-dihydro-11-(1-methyl-4-piperidinylidene)-5H-imidazo[2,1-b][3]benzazepine;

11-(1-methyl-4-piperidinylidene)-11H-imidazo[2,1-b][3]benzazepine;

6,11-dihydro-11-(1-methyl-4-piperidinylidene)-5H-imidazo[2,1-b][3]benzazepine-3-methanol;

8-fluoro-6,11-dihydro-11-(1-methyl-4-piperidinylidene)-5H-imidazo[2,1-b][3]benzazepine;

6,11-dihydro-11-(1-methyl-4-piperidinylidene)-5H-imidazo[2,1-b][3]benzazepine-3-carboxaldehyde;

6,11-dihydro-11-(1-methyl-4-piperidinylidene)-5H-imidazo[2,1-b][3]benzazepine-3carboxylic acid;

7-fluoro-6,11-dihydro-11-(1-methyl-4-piperidinylidene)-5H-imidazo[2,1-b][3]benzazepine; and 4-(8-fluoro-5,6-dihydro-11H-imidazo[2,1-b][3]benzazepin-11-ylidene)-1-piperidinepropanoic acid dihydrate.

6. A pharmaceutical composition comprising as an active ingredient a therapeutically effective amount of a compound as defined in claim 1 and a pharmaceutically acceptable carrier.

7. A pharmaceutical composition comprising as an active ingredient a therapeutically effective amount of a compound as defined in claim 2 and a pharmaceutically acceptable carrier.

8. A pharmaceutical composition comprising as an active ingredient a therapeutically effective amount of a compound as defined in claim 3 and a pharmaceutically acceptable carrier.

9. A pharmaceutical composition comprising as an active ingredient a therapeutically effective amount of a compound as defined in claim 4 and a pharmaceutically acceptable carrier.

10. A pharmaceutical composition comprising as an active ingredient a therapeutically effective amount of a compound as defined in claim 5 and a pharmaceutically acceptable carrier.

11. A method of treating allergic conditions in warm blooded animals which comprises administering to warm blooded animals suffering from allergic conditions an effective anti-allergic amount of a compound as defined in claim 1.

12. A method of treating allergic conditions in warm blooded animals which comprises administering to warm blooded animals suffering from allergic conditions an effective anti-allergic amount of a compound as defined in claim 2.

13. A method of treating allergic conditions in warm blooded animals which comprises administering to warm blooded animals suffering from allergic conditions an effective anti-allergic amount of a compound as defined in claim 3.

14. A method of treating allergic conditions in warm blooded animals which comprises administering to warm blooded animals suffering from allergic conditions an effective anti-allergic amount of a compound as defined in claim 4.

15. A method of treating allergic conditions in warm blooded animals which comprises administering to warm blooded animals suffering from allergic conditions an effective anti-allergic amount of a compound as defined in claim 5.

16. A compound of the formula:

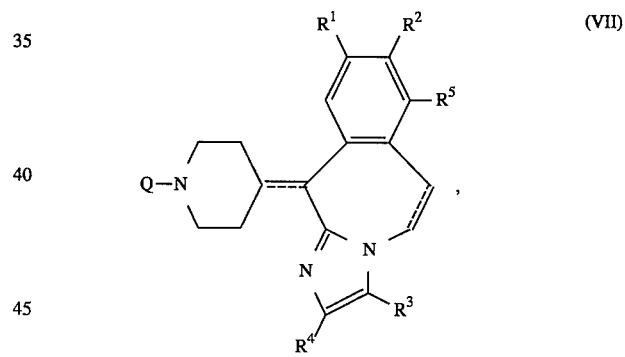

an acid addition salt thereof or a stereochemically isomeric form thereof, wherein each of the dotted lines independently represents an optional bond, and wherein:

$R^1$ represents hydrogen, halo, $C_{1-4}$alkyl or $C_{1-4}$alkyloxy;

$R^2$ represents hydrogen, halo, $C_{1-4}$alkyl or $C_{1-4}$alkyloxy;

$R^3$ represents hydrogen, $C_{1-4}$alkyl, ethenyl substituted with hydroxycarbonyl or $C_{1-4}$alkyloxycarbonyl, $C_{1-4}$alkyl substituted with hydroxycarbonyl or $C_{1-4}$alkyloxycarbonyl, hydroxy$C_{1-4}$alkyl, formyl or hydroxycarbonyl;

$R^4$ represents hydrogen, $C_{1-4}$alkyl, hydroxy$C_{1-4}$alkyl, phenyl or halo;

$R^5$ represents hydrogen, $C_{1-4}$alkyl or halo; and

Q represents phenyloxycarbonyl, or $C_{1-6}$alkyl substituted with a member selected from the group consisting of halo, cyano, amino, isothiocyanato, (4-amino-3-pyridinyl)aminothiocarbonylamino, $(CH_3O)_2CH-CH_2-NH-C(=NCH_3)-NH-$, and methylsulfonyloxy.

* * * * *

UNITED STATES PATENT AND TRADEMARK OFFICE
CERTIFICATE OF CORRECTION

| | | |
|---|---|---|
| PATENT NO. | : 5,468,743 | Page 1 of 1 |
| APPLICATION NO. | : 08/142474 | |
| DATED | : November 21, 1995 | |
| INVENTOR(S) | : Frans E. Janssens, Gaston S. M. Diels and Joseph E. Leenaerts | |

It is certified that error appears in the above-identified patent and that said Letters Patent is hereby corrected as shown below:

The title on the cover page, item [54] Col. 1 should be:

IMIDAZO[2,1-B][3]BENZAZEPINE DERIVATIVES, COMPOSITIONS AND METHOD OF USE

Signed and Sealed this
Fifth Day of July, 2011

David J. Kappos
*Director of the United States Patent and Trademark Office*